US011007283B2

(12) United States Patent
Lattuada et al.

(10) Patent No.: US 11,007,283 B2
(45) Date of Patent: May 18, 2021

(54) CONTRAST AGENTS

(71) Applicant: BRACCO IMAGING S.P.A., Milan (IT)

(72) Inventors: Luciano Lattuada, Cassina de' Pecchi (IT); Roberta Napolitano, Albiano d'Ivrea (IT); Valeria Boi, Strambino (IT); Massimo Visigalli, Settala (IT); Silvio Aime, Carignano (IT); Giovanni Battista Giovenzana, Novara (IT); Alberto Fringuello Mingo, Envie (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

(21) Appl. No.: 16/092,905

(22) PCT Filed: Apr. 5, 2017

(86) PCT No.: PCT/EP2017/058104
§ 371 (c)(1),
(2) Date: Oct. 11, 2018

(87) PCT Pub. No.: WO2017/178301
PCT Pub. Date: Oct. 19, 2017

(65) Prior Publication Data
US 2019/0167819 A1    Jun. 6, 2019

(30) Foreign Application Priority Data

Apr. 13, 2016    (EP) .................................. 16165016

(51) Int. Cl.
| A61K 49/10 | (2006.01) |
| A61B 5/055 | (2006.01) |
| C07F 9/6524 | (2006.01) |
| C07D 257/02 | (2006.01) |
| G01R 33/56 | (2006.01) |

(52) U.S. Cl.
CPC ............ A61K 49/106 (2013.01); A61B 5/055 (2013.01); C07D 257/02 (2013.01); C07F 9/6524 (2013.01); G01R 33/5601 (2013.01)

(58) Field of Classification Search
CPC .. A61K 49/106; A61B 5/055; G01R 33/5601; C07F 9/6524
See application file for complete search history.

(56) References Cited

U.S. PATENT DOCUMENTS

| 4,647,447 A | 3/1987 | Gries et al. |
| 4,885,363 A | 12/1989 | Tweedle et al. |
| 4,916,246 A | 4/1990 | Felder et al. |
| 5,132,409 A | 7/1992 | Felder et al. |
| 5,277,895 A | 1/1994 | Platzek et al. |
| 5,316,757 A | 5/1994 | Dean et al. |
| 5,374,416 A | 12/1994 | Rousseaux et al. |
| 5,876,698 A | 3/1999 | Schmitt-Willich et al. |
| 5,919,431 A * | 7/1999 | Higler .................... A61K 49/06 424/9.363 |
| 5,980,864 A | 11/1999 | Platzek et al. |
| 6,149,890 A | 11/2000 | Uggeri et al. |
| 2005/0175543 A1* | 8/2005 | Aime ................... C07C 237/12 424/9.365 |

FOREIGN PATENT DOCUMENTS

| DE | 19849465 A1 | 4/2000 |
| EP | 0230893 B1 | 8/1987 |
| EP | 0468634 A1 | 1/1992 |
| EP | 0485045 A2 | 5/1992 |
| EP | 0499501 B1 | 8/1992 |
| EP | 0512661 A1 | 11/1992 |
| EP | 1155023 B1 | 11/2001 |
| WO | 9009388 A1 | 8/1990 |
| WO | 9505118 A1 | 2/1995 |
| WO | 2005062828 A2 | 7/2005 |
| WO | 2008126034 A2 | 10/2008 |

OTHER PUBLICATIONS

Bischofberger, N. et al. "Synthesis of Analogues of 1,3-Dihydroxyacetone Phosphate and Glyceraldehyde 3-Phosphate for Use in Studies of Fructose-1,6-diphosphate Aldolase," J. Org. Chem., vol. 53: 3457-3465 (1988).
Caravan, P. et al. "Gadolinium(III) Chelates as MRI Contrast Agents: Structure, Dynamics, and Applications," Chem. Rev. vol. 99: 2293-2352 (1999).
Cassel, S. "Original Synthesis of Linear, Branched and Cyclic Oligoglycerol Standards," Eur. J. Org. Chem. 875-896 (2001).
Li, C. et al. "A Simple, Regioselective Synthesis of 1,4-Bis(tert-butoxycarbonylmethyl)-tetraazacyclododecane" J. Org. Chem. 68:2956-2959 (2003).
Ermelindo, A. et al. "Synthesis of a mixed carboxylate-phosphinate AAZTA-like ligand and relaxometric characterization of its GdIII complex," Tetrahedron Letters 54:6378-6380 (2013).
Greene et al. (Eds.), Protective Groups in Organic Synthesis, John Wiley & Sons, Inc., Chapter 5, pp. 152-179 (1981).
Jana, S. et al. "Synthesis of Novel C-Pivot Lariat 18-Crown-6 Ethers and Their Efficient Purification," Synlett 26:1977-1980 (2015).
Kholod, I. et al. "Preparation of precursors for the synthesis of analogues of rhazinilam" ARKIVOC (iii) 256-273 (2014).
Koide, Y. et al. "Pharmacophore-Based Design of Sphingosine 1-phosphate-3 Receptor Antagonists That Include a 3,4-Dialkoxybenzophenone Scaffold," J. Med. Chem. 50:442-454 (2007).
(Continued)

*Primary Examiner* — Michael G. Hartley
*Assistant Examiner* — Leah H Schlientz
(74) *Attorney, Agent, or Firm* — Vivicar Law, PLLC

(57) ABSTRACT

The present invention relates to new class of functionalized polyazamacrocycles including at least one phosphonic or phosphinic group linked to a nitrogen atom of the macrocyclic cage, and capable of chelating paramagnetic metal ions, their chelated complexes with metal ions and the use thereof as contrast agents, particularly suitable for Magnetic Resonance Imaging (MRI) analysis.

15 Claims, No Drawings

(56) References Cited

OTHER PUBLICATIONS

Kovacs, Z. et al. "pH-Controlled Selective Protection of Polyaza Macrocycles," Synthesis, 759-763 1997.
Li, C. et al. "A selective one-step synthesis of tris N-alkylated cyclens," 60:5595-5601 (2004).
Li, J. et al. "Synthesis and Anticancer Activities of Novel 1,4-Disubstituted Phthalazines" Molecules 11:574-582 (2006).
Manning, H.C. et al. "Expeditious synthesis of 'P'-protected macrocycles en routeto lanthanide chelate metal complexes," Tetrahedron Letters, 46:4707-4710 (2005).
Murata, T. "Synthesis and structure-activity relationships of novel IKK-β inhibitors. Part 2: Improvement of in vitro activity," Bioorg. Med. Chem. Lett. 14:4013-4017 (2004).
Shin, J. et al. "1-Arylsulfonyl-2-(Pyridylmethylsulfinyl) Benzimidazoles as New Proton Pump Inhibitor Prodrugs," Molecules 14:5247-5280 (2009).
Skwierawska, A. "Selective monoprotection of 1,4,7,10-tetraazacyclododecane via direct reaction with 4-nitrophenyl active esters," Tetrahedron Letters 49:6308-6310 (2008).
Yadav, J. et al. "Stereoselective synthesis of C19-C27 fragment of bryostatin 11," Tetrahedron Letters 55:4054-4056 (2014).
PCT Search Report and Written Opinion for PCT/EP2017/058104, dated Jun. 20, 2017.
Greene et al. (Eds.), Protective Groups in Organic Synthesis, Third Edition, John Wiley & Sons, Inc., Chapter 7, pp. 494-653 (1999).

\* cited by examiner

CONTRAST AGENTS

CROSS REFERENCE TO RELATED APPLICATIONS

This application is the national stage application of corresponding international application number PCT/EP2017/058104, filed Apr. 5, 2017, which claims priority to and the benefit of European application no. 16165016.3, filed Apr. 13, 2016, all of which are hereby incorporated by reference in their entirety.

FIELD OF THE INVENTION

The present invention relates to the field of diagnostic imaging and to novel contrast agents possessing improved relaxivity. More in particular, it relates to functionalized macrocycles capable of chelating paramagnetic metal ions, their chelated complexes with metal ions and the use thereof as contrast agents in Magnetic Resonance Imaging (MRI).

STATE OF THE ART

Magnetic Resonance Imaging (MRI) is a renowned diagnostic imaging technique increasingly used in clinical diagnostics for growing number of indications.

The undisputed success of this technique is determined by the advantages it offers, including a superb temporal and spatial resolution, the outstanding capacity of differentiating soft tissues and its safety, due to its non-invasiveness and the absence of any ionizing radiation, in contrast to, for instance, X-ray, PET and SPECT.

In MRI imaging the contrast is basically due to differences existing in the longitudinal T1 and the transverse T2 relaxation times of the water protons in the different body organs and tissues, which allows the in-vivo acquisition of high-resolution, three-dimensional images of the distribution of water.

The intensity of the signal recorded in MRI imaging stems, essentially, from the local value of the longitudinal relaxation rate 1/T1, and the transverse rate, 1/T2 of water protons, and increases with increasing of the 1/T1 value (of the longitudinal relaxation rate of water protons) while decreases with the increase of 1/T2. In other words, the shorter is T1, the higher is the intensity of the recorded signal in MRI, the better is the diagnostic image.

The strong expansion of medical MRI has further benefited from the development of a class of compounds, the MRI contrast agents, that act by causing a dramatic variation of nearby water proton relaxation rates in the tissues/organs/fluids wherein they distributes, thus adding relevant physiological information to the impressive anatomical resolution commonly obtained in the uncontrasted MRI images.

Contrast agents for use in the MRI imaging technique typically include a paramagnetic metal ion which is complexed with a cyclic or acyclic chelating ligand, more typically a polyaminopolycarboxylic chelator. The most important class of MRI contrast agents is represented by the Gd(III) chelates which are currently used in about ⅓ of the clinical tests. Indeed, Gd(III) is highly paramagnetic with seven unpaired electron and a long electronic relaxation time, making it an excellent candidate as a relaxation agent. By contrast, the free metal ion $[Gd(H_2O)_8]^{3+}$ is extremely toxic for living organism even at low doses (10-20 micromol/Kg). Thus, in order for it to be considered as a potentially valuable MRI contrast agent, a Gd(III) complex shall display a high thermodynamic (and possibly kinetic) stability ensuring against the release of toxic metal ion.

Preferred MRI contrast agent should furthermore display optimal relaxivity. Relaxivity ($r_{1p}$, $r_{2p}$), expressed in $mM^{-1}s^{-1}$ and usually measured at 298K and 20 MHz (approx. 0.5 T), is the intrinsic property of a paramagnetic complex which characterizes its capability to increase the nuclear magnetic relaxation rate, longitudinal ($1/T_1$) and transverse ($1/T_2$) respectively, of vicinal water protons and, thus, its efficacy as MRI contrast enhancing agent. In general terms, the higher the relaxivity of an MRI contrast agent, the greater its contrast enhancing capability and the stronger the contrast provided in recorded MRI images.

A number of complexes of paramagnetic metal ions are known in the art (see for instance: Caravan P. et al. Chem. Rev. 1999, 99, 2293-2352 and U.S. Pat. Nos. 4,647,447, 4,885,363; 4,916,246; 5,132,409; 6,149,890; and 5,980,864).

The majority of them is represented by stable complexes of Gd (III) ions with octadentate polyaminopolycarboxylic ligands ensuring both high thermodynamic complex stability and a residual coordination site, available to coordinate one water molecule in the inner coordination sphere of the Gd(III) ion, which in fact has coordination number of nine.

Additional complex compounds moreover exist with chelating ligands having phosphinic or phosphonic residue(s) in place of the metal chelating carboxylic group(s), for instance disclosed in EP 1155023, EP0468634, EP0499501, WO90/09388, WO2005/062828 and WO95/05118.

Polymeric compounds, potentially having up to 400 carboxylated and/or phosphonated macrocyclic ligands appended to a polymeric backbone molecule are e.g. disclosed in EP 512661.

Examples of commercially available MRI contrast agents comprise the complexes of the $Gd^{3+}$ ion with polyaminopolycarboxylic ligands, e.g. including the $Gd^{3+}$ complex of the DTPA ligand, marketed as MAGNEVIST®; the $Gd^{3+}$ complex of the DTPA-BMA ligand, marketed as OMNISCAN®; the $Gd^{3+}$ complex of BOPTA, known as gadobenate Dimeglumine and marketed as MultiHance™; the $Gd^{3+}$ complex of the DOTA ligand, marketed as DOTAREM®; the $Gd^{3+}$ complex of the hydroxylated tetraaza macrocyclic ligand known as HPDO3A, long time marketed as ProHance® and that of the corresponding butyl-triol derivative, known as Gadobutrol and marketed as Gadavist®. All the above contrast agents are Non-Specific Agents (NSA), designed for a general use.

While these compounds generally provide a quality of the imaging capable of meeting and satisfying the present needs of radiologists resulting in accurate and detailed diagnostic information, there is nevertheless still the need for new compounds with improved contrast imaging features, such as increased relaxivity.

In particular, compounds with improved relaxivity could reduce the required dose of the paramagnetic contrast agent and possibly shorten the acquisition time of the imaging process.

SUMMARY OF THE INVENTION

The present invention generally relates to novel macrocyclic chelating ligands useful for the preparation of the paramagnetic complexes having particularly favorable characteristics, above all in terms of relaxivity.

In general terms, one aspect of the present invention relates to novel tetraaza macrocyclic ligands having at least one phosphonated or phosphinated residue linked to a nitrogen atom of the macrocycle, and a pendant arm on another nitrogen atom of the chelating cage comprising a hydroxyl residue and suitable substituent group(s). In particular, the combination of phosphonated or phosphinated residue(s) on the macrocyclic chelating cage and suitable substituents on the pendant arm provides chelated complexes having improved relaxivity.

The invention further relates to respective chelated complexes of said chelating ligands with a paramagnetic metal ion and, especially, with $Gd^{3+}$, or of a physiologically acceptable salt thereof.

A further aspect of the invention relates to the use of such chelated complexes as contrast agents, in particular for the diagnostic imaging of a human or animal body organ or tissue by use of the MRI technique.

In an additional aspect the invention relates to a manufacturing process for the preparation of the provided ligands, their complex compounds with a paramagnetic metal ion, and the pharmaceutical acceptable salt thereof and their use in the preparation of a diagnostic agent.

According to another aspect, the invention relates to a pharmaceutically acceptable composition comprising at least one paramagnetic complex compound of the invention, or a pharmaceutical salt thereof, in admixture with one or more physiologically acceptable carriers or excipients. Said compositions are useful in particular as MRI contrast media, to provide diagnostically useful images of human or animal body organs or tissues.

Therefore, in another aspect, the present invention refers to a method for the diagnostic imaging of a body organ, tissue or region by use of MRI technique that comprises the use of an effective dose of a compound of the invention.

DETAILED DESCRIPTION OF THE INVENTION

The present invention relates to chelating ligands of formula (I),

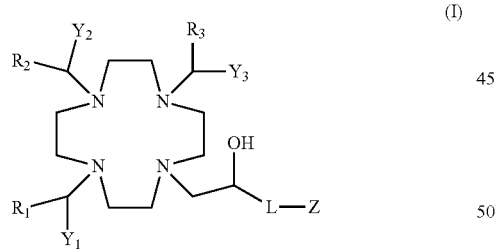

where:
$R_1$, $R_2$ and $R_3$ independently of one another are H or a $C_1$-$C_3$ alkyl optionally substituted by a $C_1$-$C_3$ alkoxy or $C_1$-$C_3$ hydroxyalkoxy group, or by a phenyl ring;

$Y_1$, $Y_2$ and $Y_3$ independently of one another are a group of formula —PO(OR')$_2$, —PO($R_4$)(OR'), or —COOR', with the proviso that at least one of them is —PO(OR')$_2$ or —PO($R_4$)(OR');

in which:
R' independently of one another is H or $C_1$-$C_5$ alkyl;
$R_4$ is an aryl or a cycloalkyl ring, or a $C_1$-$C_5$ alkyl which is optionally substituted by an aryl or cycloalkyl ring;

L is a direct bond or a —(CH$_2$)$_n$— chain;
where:
n is 1, 2 or 3;
Z is selected from the group consisting of: a substituted phenyl; a $C_1$-$C_6$ alkyl chain, that is optionally interrupted by one or more groups selected from —O—, —NH— and —CO—, and is substituted by one or more, equal or different, substituent group(s) selected from hydroxyl, carboxyl, halogen atom, or by a group of formula —O—(CH$_2$)$_m$—Ar, —NHSO$_2$R$_5$, —NHC(O)NHR$_6$, —NHC(O)OR$_7$, or —NR$_8$R$_9$; and a macrocyclic residue —W—G—W'—T;
where:
Ar is an aryl;
m is 0, 1 or 2;
$R_5$ is a $C_1$-$C_3$ alkyl optionally substituted by one or more halogen atoms, or an aryl or cycloalkyl ring;
$R_6$ is $C_1$-$C_5$ alkyl, optionally substituted with an aryl or a cycloalkyl ring; or an aryl or cycloalkyl ring;
$R_7$ is $C_1$-$C_5$ alkyl, optionally interrupted by one or more oxygen atoms and optionally substituted by an aryl or a cycloalkyl ring; or an aryl or cycloalkyl ring;
$R_8$ is an aryl or cycloalkyl ring; or a $C_1$-$C_5$ alkyl optionally substituted by one or more groups selected from hydroxyl, $C_1$-$C_3$ alkoxy, $C_1$-$C_3$ hydroxyalkoxy, an aryl or cycloalkyl ring, and a macrocyclic residue T;
$R_9$ is H, or a group of formula —(CH$_2$)$_n$PO(OR')$_2$, —(CH$_2$)$_n$PO(R$_4$)(OR') or —(CH$_2$)$_n$COOR';
W and W' the same or different from one another, are a bifunctional group selected from —O—, —S(O)$_2$NH—, —NHS(O)$_2$—, —CONH—, and —NHCO—;
G is a phenylene —C$_6$H$_4$—, or a linear or branched $C_1$-$C_5$ alkylene optionally interrupted by one or more oxygen atoms and optionally substituted by one or more groups selected from hydroxyl, carboxyl, $C_1$-$C_3$ alkoxy, and an aryl ring; and
T is a macrocyclic residue of formula (II)

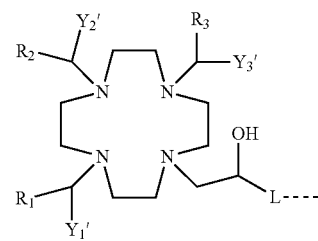

where:
$Y_1'$, $Y_2'$ and $Y_3'$ independently of one another are a group of formula —COOR', —PO(OR')$_2$, or —POR$_4$(OR'); and the dashed line represents the linking bond with the rest of the molecule.

In the present description, and unless otherwise provided, the expression alkyl comprises within its meaning any linear or branched hydrocarbon chain derived from the corresponding hydrocarbon by removal of one hydrogen atom, preferably comprising up to 12 carbon atoms.

In particular, the expression "$C_1$-$C_6$ alkyl" or "$C_1$-$C_6$ alkyl chain" as herein used interchangeably, comprises within its meanings a linear or branched hydrocarbon chain comprising from 1 to 6 carbon atoms such as: methyl, ethyl, propyl, iso-propyl, butyl, iso-butyl, tert-butyl, n-pentyl, iso-pentyl, n-hexyl, iso-hexyland the like.

Similarly, the term "$C_1$-$C_5$ alkyl" comprises within its meanings a linear or branched hydrocarbon chain comprising from 1 to 5 carbon atoms such as, for instance, methyl, ethyl, propyl, iso-propyl, butyl, iso-butyl, tert-butyl, n-pentyl, iso-pentyl, and the expression "$C_1$-$C_3$ alkyl" comprises a linear or branched hydrocarbon chain comprising from 1 to 3 carbon atoms such as, for instance, methyl, ethyl, propyl and iso-propyl.

By analogy, the expression "$C_1$-$C_5$ alkylene" comprises within its meanings a bivalent straight or branched hydrocarbon chain derived from any of the corresponding $C_1$-$C_5$ hydrocarbon chains by removal of two hydrogen atoms from different carbon atoms, including $C_1$-$C_5$ alkylene such as for instance a methylene, ethylene, propylene, iso-butylene, iso-propylene and so on.

Likewise, the term "alkoxy" comprises within its meanings any of the corresponding alkyl-oxy (or —Oalkyl) groups such as methoxy, ethoxy, n-propoxy, isopropoxy and the like;

the term "hydroxyalkyl" comprises within its meanings any of the corresponding alkyl moiety wherein one or more hydrogen atoms are replaced by hydroxyl (—OH) groups such as, preferably, hydroxymethyl (—$CH_2OH$), hydroxyethyl (—$CH_2CH_2OH$), hydroxypropyl (—$CH_2CH_2CH_2OH$), dihydroxypropyl,(—$CH_2CH(OH)CH_2OH$ and —$CH(CH_2OH)_2$) and the likeand the term "hydroxyalkoxy" comprises within its meanings any of the corresponding $C_1$-$C_5$ or $C_1$-$C_3$ alkyl-oxy groups comprising one or more hydroxyls (—OH) in the alkyl chain. In the present description, and unless otherwise specifically provided, the term "carboxyl" comprises within its meanings a residue of formula —COOR', or that comprises said —COOR' residue, e.g. of formula —$(CH_2)_m$—COOR', —$O(CH_2)_n$—COOR', or —$(OCH_2)_m$—COOR', where n, m and R' are as above defined.

With "halogens" or "halogen atoms" we intend iodine, chlorine, bromine, or fluorine atoms; while with "halogen" or "halogen atom" we refer to an atom selected from the above listed halogens.

The expression "halogenated alkyl" comprises within its meanings an alkyl group wherein one or more hydrogen atoms are replaced by halogen atom(s), preferably chlorine or fluorine and, more preferably, fluorine atom(s).

The expression "perfluorinated $C_1$-$C_3$ alkyl" comprises within its meanings a $C_1$-$C_3$ alkyl group wherein all the hydrogen atoms are replaced by fluorine atoms, like the —$CF_3$, —$C_2F_5$, and —$C_3F_7$ alkyl groups, where —$CF_3$ (i.e. trifluoromethyl) is preferred.

In the present description the term "aryl" or "aryl ring" refers to an aromatic hydrocarbon which may be either heterocyclic or, preferably, carbocyclic, and, more preferably, is a phenyl ring. Unless otherwise specifically provided, aryls according to the invention can be either unsubstituted or substituted with one or more, equal or different, substituent groups, for instance selected from hydroxyl (OH), halogen, $C_1$-$C_3$ alkyl, $C_1$-$C_3$ alkoxy, $C_1$-$C_3$ hydroxyalkyl, —$NH_2$, nitro, carboxyl, carbamoyl, or $C_1$-$C_3$ alkyl- or dialkylamino; preferably selected from hydroxyl, halogen, $C_1$-$C_3$ alkyl, $C_1$-$C_3$ alkoxy, —$NH_2$, or carboxyl and, more preferably, from hydroxyl, $C_1$-$C_3$ alkyl or alkoxy, —$NH_2$, —$OCH_2COOH$, —$CH_2COOH$, and —COOH.

Likewise, with the term "arylene" we intend a divalent aryl radical, for instance a phenylene —$C_6H_4$—.

The term "cycloalkyl ring" comprises within its meanings a cycloaliphatic ring, and, preferably, a $C_5$-$C_7$ carbocyclic ring e.g. a cyclohexyl ring. Unless otherwise specifically provided, cycloalkyl rings according to the invention can be either unsubstituted or substituted with one or more, equal or different, substituent groups for instance selected from hydroxyl (OH), halogen, $C_1$-$C_3$ alkyl, $C_1$-$C_3$ alkoxy, $C_1$-$C_3$ hydroxyalkyl, carboxyl, carbamoyl, nitro, —$NH_2$, or $C_1$-$C_3$ alkyl- or dialkylamino, and preferably from $C_1$-$C_3$ alkyl or alkoxy, —$CH_2COOH$, and —COOH.

From all the above, having defined the meanings for alkyl and aryl, any composite-name such as alkyl-aryl, aryl-alkyl, cycloalkyl-alkyl and the like should be clear to a skilled person.

Just as an example, and unless otherwise provided, the term alkylaryl (or alkyl-aryl, as herein used interchangeably) comprises within its meanings an aryl group further substituted by an alkyl, (e.g. p-ethyl-phenyl; $pC_2H_5$—$C_6H_5$—) while the term arylalkyl (or aryl-alkyl) or cycloalkyl-alkyl comprises within its meanings an alkyl further substituted by an aryl (e.g. phenyl-ethyl=$C_6H_5$—$C_2H_4$—) or a cycloalkyl (e.g. cyclohexyl-ethyl=$C_6H_{11}$—$C_2H_4$—); and the like.

In the present description the term "protecting group" designates a protective group adapted for preserving the function of the group to which it is bound. Specifically, protective groups are used to preserve amino, hydroxyl or carboxyl functions. Appropriate carboxyl protecting groups may thus include, for example, benzyl, alkyl e.g. tert-butyl or benzyl esters, or other substituents commonly used for the protection of such functions, which are all well known to those skilled in the art. [see, for a general reference, T. W. Green and P. G. M. Wuts; *Protective Groups in Organic Synthesis*, Wiley, N.Y. 1999, third edition].

Moreover, the terms "moiety" or "moieties", "residue" or "residues" are herewith intended to define the residual portion of a given molecule, once properly attached or conjugated, either directly or through any suitable linker, to the rest of the molecule.

The compounds of the above formula (I) may have one or more asymmetric carbon atom, otherwise referred to as a chiral carbon atom, and may thus give rise to diastereoisomers and optical isomers. Unless otherwise provided, the present invention further includes all such possible diastereoisomers as well as their racemic mixtures, their substantially pure resolved enantiomers, all possible geometric isomers, and pharmaceutical acceptable salts thereof.

In one embodiment, the invention relates to compounds of formula (I) in which L is an alkylene chain (—$(CH_2)_n$—) including 1, 2 or 3 and, preferably, 1 carbon atom.

In an alternative embodiment, in the above formula (I) L is a direct bond, and Z is directly linked to the carbon atom bearing the hydroxyl group through a direct covalent link.

In one embodiment the invention relates to compounds of formula (I) in which Z is a substituted phenyl, which is linked to the hydroxylated carbon atom through a —$(CH_2)_n$— alkylene chain L or, preferably, through a direct bond.

Substituted phenyls according to the invention comprise a substituent group Q which can be bound to each of the free positions of the aromatic ring. Preferably, the substituent group is in ortho with respect to the bond between the phenyl ring and the hydroxylated carbon atom of the macrocyclic molecule.

In one preferred embodiment the invention relates to phenyl derivative of formula (III)

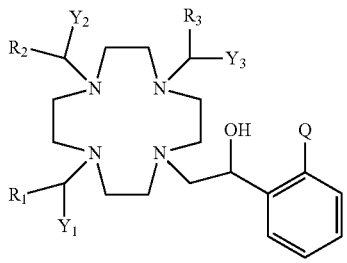

(III)

in which Q is a substituent group selected from hydroxyl, —NH$_2$, C$_1$-C$_3$ alkoxy, C$_1$-C$_3$ hydroxyalkyl, and carboxyl e.g. of formula —(CH$_2$)$_m$COOH, where m is as above defined and, preferably is 0 or 1; and R$_1$, R$_2$, R$_3$, Y$_1$, Y$_2$ and Y$_3$ are as above defined for the compounds of formula (I). More preferably, Q is selected from the group consisting of hydroxyl, —NH$_2$, —OCH$_3$ and —COOH and, most preferably, is —OH or —COOH.

In another embodiment the invention relates to compounds of formula (I) in which Z is a C$_1$-C$_6$ alkyl chain that is optionally interrupted by one or more groups selected from —O—, —NH— and —CO—, and is substituted by one or more groups selected from hydroxyl, carboxyl, halogen atoms, or by a group of formula —O—(CH$_2$)$_m$—Ar, —NHSO$_2$R$_5$, —NHC(O)NHR$_6$, —NHC(O)OR$_7$ or —NR$_8$R$_9$.

Preferably, in these compounds L is a direct bond, and the Z-chain is directly linked to the hydroxylated carbon atom of the macrocyclic molecule by means of a direct covalent bond.

More preferably, in these compounds Z is a C$_1$-C$_6$ alkyl chain that is optionally interrupted by one or more oxygen atoms (—O—), and is substituted by one or more groups selected from hydroxyl, carboxyl, halogen atoms, or by a group of formula —O—(CH$_2$)$_m$—Ar, —NHSO$_2$R$_5$, —NHC(O)NHR$_6$, and —NHC(O)OR$_7$.

Suitable examples, for instance, include compounds of the above formula (I) in which Z is a C$_1$-C$_6$ and, preferably, a C$_1$-C$_3$ alkyl that is substituted by one or more hydroxyl group(s), or halogen atom(s) and, preferably, fluorine atoms, e.g. a perfluorinated C$_1$-C$_3$ alkyl such as —C$_2$F$_5$ and, more preferably, —CF$_3$.

Additional examples comprise compounds of formula (I) in which L is a direct bond and Z is a C$_1$-C$_6$ alkyl chain interrupted by one or more oxygen —O— atom(s), and/or substituted by group of formula —O—(CH$_2$)$_m$Ar, where m and Ar are as defined for compounds of formula (I).

In particular, in one preferred embodiment the invention relates to aryl ethers of formula (IV)

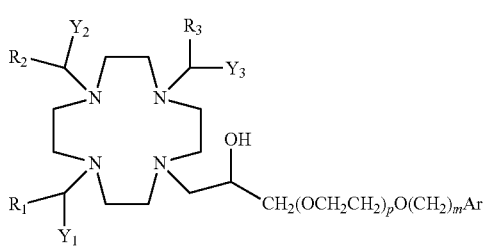

(IV)

in which p is 0 or 1; and m, Ar, R$_1$, R$_2$, R$_3$, Y$_1$, Y$_2$ and Y$_3$ are as above defined for the compounds of formula (I).

Preferably in the above compounds of formula (IV) p is 0; m is 0 or 1; and Ar is an aromatic ring, e.g. a phenyl ring, which can be either unsubstituted, or substituted by a group for instance selected from hydroxyl, C$_1$-C$_3$ alkoxy and a carboxyl, e.g. of formula —(OCH$_2$)$_m$COOH or —(CH$_2$)$_m$COOH, where m is as above defined. More preferably, Ar is an unsubstituted phenyl, or a phenyl ring substituted by a group selected from —OH, —OCH$_3$, —COOH, —OCH$_2$COOH and —CH$_2$COOH.

In an alternative embodiment the invention relates to compounds according to the formula (I) where L is a direct bond and Z is a C$_1$-C$_6$ and, preferably, a C$_1$-C$_3$ alkyl which comprises a substituent group selected from the groups of formula —NHSO$_2$R$_5$, —NHC(O)OR$_7$, —NHC(O)NHR$_6$, in which R$_5$, R$_6$ and R$_7$ are as above defined.

Suitable examples, for instance, comprise macrocyclic compounds according to the above formula (I) in which Z is a C$_1$-C$_3$ alkyl substituted by a sulphonamide group of formula —NHSO$_2$R$_5$ where R$_5$ is as above defined.

In particular, according to another preferred embodiment the invention relates to sulfonamide derivative of formula (V)

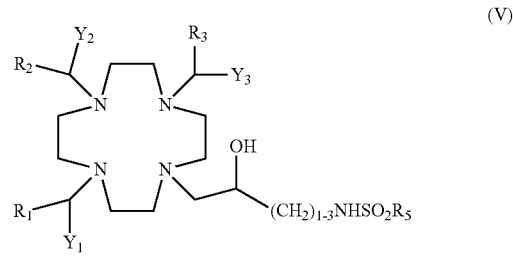

(V)

in which R$_5$ is an optionally perfluorinated C$_1$-C$_3$ alkyl, such as methyl, ethyl or propyl or the corresponding perfluorinated derivatives; or is an aryl or cycloalkyl ring, e.g. an optionally substituted cyclohexyl or, preferably, phenyl ring; and R$_1$, R$_2$, R$_3$, Y$_1$, Y$_2$ and Y$_3$ are as above defined for the compounds of formula (I).

Preferably, R$_5$ is a perfluorinated alkyl e.g. —C$_2$F$_5$ and, preferably, CF$_3$; or a cyclohexyl or, preferably, a phenyl ring which is optionally substituted by one or more halogen atoms, e.g. fluorine atoms, or by a carboxyl group, e.g. of formula —(CH$_2$)$_m$COOH or —(OCH$_2$)$_m$COOH where m is 0 or 1.

In a further embodiment the invention relates to compounds according to the formula (I) in which L is a direct bond and Z is a C$_1$-C$_6$ or, more preferably, a C$_1$-C$_3$ alkyl which is substituted by an urea derivative of formula —NHC(O)NHR$_6$, or by a carbamate derivative of formula —NHC(O)OR$_7$ in which R$_6$ and R$_7$ are as above defined.

Suitable examples include urea derivatives of formula (VI)

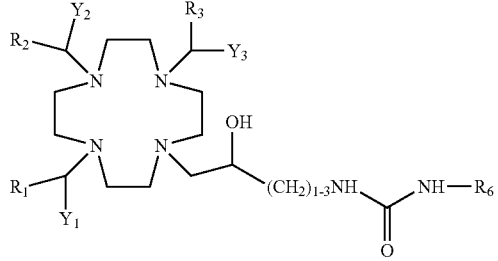

or carbamate derivatives of formula (VII)

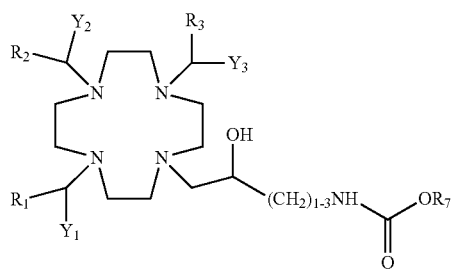

in which $R_6$ is a $C_1$-$C_3$ alkyl such as methyl, ethyl or propyl, which is optionally substituted by a phenyl or a cyclohexyl ring e.g. a benzyl, phenyl-ethyl, cyclohexyl-methyl or cyclohexyl-ethyl group; or is an aryl or cycloalkyl ring; and $R_7$ is $C_1$-$C_5$ alkyl such as methyl, ethyl, propyl or butyl, optionally interrupted by one or more oxygen atom(s) and optionally substituted by a phenyl or a cyclohexyl ring, or is an aryl or cycloalkyl ring e.g. an optionally substituted phenyl or a cyclohexyl ring.

Preferred urea derivatives include compounds of the formula (VI) where $R_6$ is selected from the group consisting of phenyl, cyclohexyl, benzyl, phenyl-ethyl, cyclohexyl-methyl and cyclohexyl-ethyl and, most preferably from phenyl, cyclohexyl and benzyl.

Preferred carbamate derivatives include compounds of the above formula (VII) where $R_7$ is selected from the group consisting of phenyl, cyclohexyl, benzyl, cyclohexyl-methyl, methoxy-($C_1$-$C_3$)alkyl, benzyloxy-($C_1$-$C_3$)alkyl, and, most preferably, from phenyl, cyclohexyl, benzyl, methoxyethyl and benzyloxyethyl.

In a still additional embodiment the invention relates to compounds according to the formula (I) in which Z is a $C_1$-$C_6$ and, preferably, $C_1$-$C_3$ alkyl substituted by an amine group of formula —$NR_8R_9$ where $R_8$ and $R_9$ are as above defined for the compounds of formula (I), which is directly linked to the hydroxylated carbon atom of the macrocycle.

Suitable examples include amine derivatives of formula (VIII)

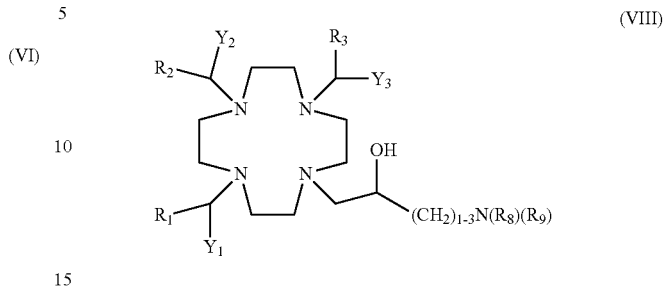

in which:

$R_8$ is an aryl or cycloalkyl ring which can be either unsubstituted or substituted as above said; or a $C_1$-$C_5$ alkyl optionally comprising one or more substituent groups selected from hydroxyl, $C_1$-$C_3$ alkoxy, $C_1$-$C_3$ hydroxyalkoxy, an optionally substituted phenyl or cyclohexyl ring, and a macrocyclic residue T;

$R_9$ is a hydrogen atom, or a group selected from the groups of formula —$(CH_2)_nPO(OR')_2$, —$(CH_2)_nPO(R_4)(OR')$ and —$(CH_2)_nCOOR'$ in which n is an integer from 1 to 3 and, preferably, is 1 or 2;

R' is a H or a $C_1$-$C_5$ alkyl e.g. ethyl or tert-butyl; and $R_4$ is an aryl or a cycloalkyl ring, e.g. an optionally substituted phenyl or a cyclohexyl ring, or is a $C_1$-$C_5$ alkyl such as, preferably a methyl, ethyl or propyl substituted or not by an aryl or cycloalkyl ring; and $Y_1$, $Y_2$, $Y_3$, R, and $R_1$, are as above defined for the compounds of formula (I).

In one embodiment, in the above compounds of formula (VIII) $R_8$ is a phenyl or a cyclohexyl ring, or is a $C_1$-$C_3$ alkyl such as methyl, ethyl or propyl, substituted by a phenyl or a cyclohexyl ring e.g. a benzyl, phenyl-ethylene, cyclohexyl-methylene or cyclohexyl-ethylene group, and $R_9$ is as above said for compounds of formula (VIII), and, preferably is H, or a group of formula —$(CH_2)_nPO(OR')_2$ or of formula —$(CH_2)_nCOOR'$ in which n is 1 or 2 and R' is as above said.

In an alternative embodiment $R_8$ is a $C_1$-$C_5$ alkyl which is optionally substituted by one or more groups selected from hydroxyl, $C_1$-$C_3$ alkoxy or hydroxyalkoxy, such as, for instance, a methyl, ethyl, propyl or isopropyl chain substituted or not by one or more hydroxyl groups, e.g. including hydroxymethyl, hydroxyethyl, hydroxypropyl and 1,3- and 2,3-dihydroxypropyl, or by one or two $C_1$-$C_3$ alkoxy or $C_1$-$C_3$ hydroxyalkoxy groups; and $R_9$ is H, or a group of formula —$(CH_2)_nPO(OR')_2$ or, preferably, of formula —$(CH_2)_nCOOR'$ in which n is 1 or 2 and R' is as above said.

In an additional embodiment the invention relates to dimeric compounds.

Suitable examples include dimeric compounds of formula (I) in which L is a direct bond or, preferably, an alkylene chain —$(CH_2)_n$—, and Z is a —W-G-W'-T residue, in which a macrocyclic molecule T of the above formula (II) is attached to the linker L through the bridging moiety —W-G-W'-.

Preferred among them are dimeric compounds of formula (IX)

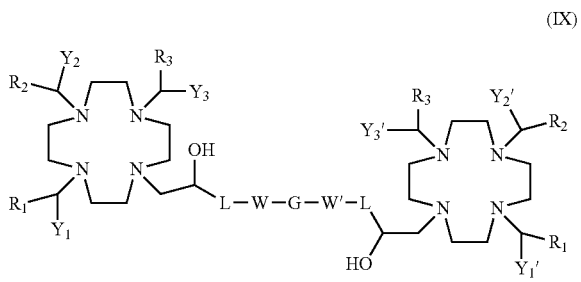

in which:

L is an alkylene chain —$(CH_2)_n$— where n is an integer from 1 to 3 and, preferably, is 1; W and W' represent, the same or different from each other, a divalent group selected from —O—, —$SO_2NH$—, —$NHSO_2$—, —CONH— and —NHCO— and, more preferably from —O— and —$NHSO_2$—; G is a bifunctional residue e.g. selected from a phenylene (—$C_6H_4$—) or a $C_1$-$C_5$ linear or branched alkylene that is, in its turn, optionally interrupted by one or more oxygen atoms, and optionally substituted by one or more groups e.g. selected from hydroxyl, phenyl and carboxyl; and $R_1$, $R_2$, $R_3$, $Y_1$, $Y_2$, $Y_3$, $Y_1'$, $Y_2'$ and $Y_3'$ are as above defined for the compounds of formula (I).

More preferably in the above compounds of formula (IX) W and W' are equal to each other and represent an oxygen atom —O— or a —$SO_2NH$— group.

Dimers according to the invention further comprise compounds of the above formula (VIII) in which $R_8$ is a $C_1$-$C_5$ and, preferably, a $C_1$-$C_3$ alkyl chain substituted by a macrocyclic residue T as well as, optionally, by one or more additional substituents groups e.g. selected from hydroxyl and $C_1$-$C_3$ alkoxy or hydroxyalkoxy.

Suitable examples for instance comprise dimeric compounds of formula (X)

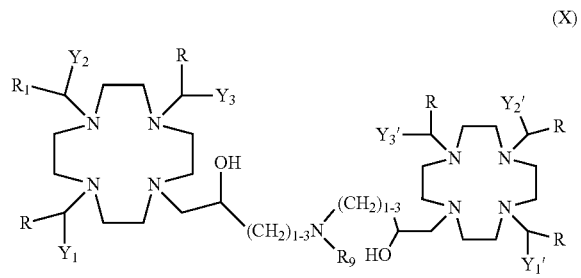

in which $R_9$ is as above said for the compounds of formula (VIII) and, preferably, is H or a group of formula —$(CH_2)_n PO(OR')_2$ or —$(CH_2)_n COOR'$ and, more preferably, is H; while R', $R_1$, $Y_1$, $Y_2$, $Y_3$, $Y_1'$, $Y_2'$ and $Y_3'$ are as defined for the compounds of formula (I).

In the dimeric compounds of the invention the groups $Y_1'$, $Y_2'$ and $Y_3'$ are, independently of one another, selected from —$PO(R_4)(OR')$, —$PO(OR')_2$, or —COOR' where $R_4$ and R' are as above defined.

In one embodiment the invention relates to dimeric compounds according to the formula (I) in which all $Y_1'$, $Y_2'$ and $Y_3'$ are a —COOR' group or, in another embodiment, where all of them comprise a phosphorus group selected from —$PO(OR')_2$ and —$POR_2(OR')$.

Preferably, in the dimers of the invention each $Y_1'$, $Y_2'$ and $Y_3'$ of the appended macrocycle is equal to the corresponding group $Y_1$, $Y_2$ and $Y_3$ of the first macrocycle to give, in a particularly preferred embodiment, symmetrical dimers of formula (IX) in which $Y_1$ is the same as $Y_1'$, $Y_2$ is the same as $Y_2'$, and $Y_3$ is the same as $Y_3'$.

In one embodiment, in the compounds of the above formula (I), and hence of encompassed formulae from (III) to (X), each of the $Y_1$, $Y_2$ and $Y_3$ groups is phosphorus-containing groups independently selected from —$PO(OR')_2$ and —$PO(R_4)(OR')$. In these compounds Z is as above discussed for compounds of formula (I) and, preferably, as defined for the compounds of the formulae from (III) to (X).

In a preferred embodiment, in the compounds of the formula (I), and encompassed compounds of formulae from (III) to (X), one or two of the $Y_1$, $Y_2$ and $Y_3$ groups is (are) a carboxyl of formula —COOR' where R' is as above said.

Suitable examples include compounds according to the above formula (I) in which $Y_1$ is a carboxyl of formula —COOR', and $Y_2$ and $Y_3$ represent, independently the one another, a group selected from —$PO(R_4)(OR')$ or —$PO(OR')_2$ or, more preferably, are both —$PO(OR')_2$; or compounds of formula (I) in in which, alternatively, $Y_2$ is a carboxyl of formula —COOR', while $Y_1$ and $Y_3$ represent, independently the one another, a phosphonic group —$PO(OR')_2$ or a phosphinic group —$PO(R_4)(OR')$ or, more preferably, are two phosphonic residues.

In a more preferred embodiment the invention relates to compounds according to the formula (I), hence encompassing those of formulae from (III) to (X), in which only one of $Y_1$, $Y_2$ and $Y_3$ is a group selected from —$PO(OR')_2$ and —$PO(R_4)(OR')$ while the remaining groups are carboxyls of formula —COOR'.

Suitable examples, for instance, include compounds of the above formula (I) in which $Y_3$ represent a phosphonic group of formula —$PO(OR')_2$ or a phosphinic group of formula —$POR_4(OR')$ while $Y_1$ and $Y_2$ are carboxyl groups of formula —COOR'; or, alternatively, macrocyclic compounds according to the formula (I) in which $Y_1$ is a —$PO(R_4)(OR')$ or, preferably, a —$PO(OR')_2$ group, and both $Y_2$ and $Y_3$ are carboxyl groups of formula —COOR'. Particularly preferred are the compounds according to the formula (I), and, hence, of encompassed compounds of formulae from (III) to (X), in which $Y_2$ is a —$PO(R_4)(OR')$ or, preferably, a —$PO(OR')_2$ group, and both $Y_1$ and $Y_3$ are carboxyl groups of formula —COOR'.

Especially preferred are macrocyclic compounds according to the formula (I), having the following formula (XI)

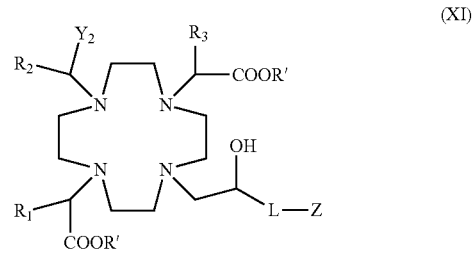

in which:
Y$_2$ is —PO(OR')$_2$ or —PO(R$_4$)(OR'); where
R' is H or a C$_1$-C$_5$ alkyl e.g. ethyl or tert-butyl; and
R$_4$ is an aryl or a cycloalkyl ring, or a C$_1$-C$_5$ alkyl which is optionally substituted by an aryl or cycloalkyl ring e.g. a phenyl, cyclohexyl, benzyl, phenyl-ethyl, cyclohexyl-methyl, cyclohexyl-ethyl;
R$_1$, R$_2$ and R$_3$ are, independently of one another, H or a C$_1$-C$_3$ alkyl optionally substituted by a C$_1$-C$_3$ alkoxy or C$_1$-C$_3$ hydroxyalkoxy group, or by a phenyl ring, and preferably are all H;
L is a direct bond or an alkylene chain —(CH$_2$)$_n$—, in which
n is an integer from 1 to 3 and, preferably, is 1
Z is a substituted phenyl; or a C$_1$-C$_6$ alkyl chain interrupted by one or more oxygen —O— atom(s) or —NH— group(s), and/or substituted by one or more, equal or different, substituent group(s) selected from hydroxyl, carboxyl, halogen, or by a group of formula —O—(CH$_2$)$_m$—Ar, —NHSO$_2$R$_5$, —NHC(O)NHR$_6$ or —NHC(O)OR$_2$; or is a macrocyclic residue —W-G-W'-T; where:
m, Ar, R$_5$, R$_6$, R$_7$ W, G, W' and T are as above defined for the compounds of formula (I).

In the compounds of the formula (I) according to the invention, hence encompassing those of formulae from (III) to (XI), each acidic group, either belonging to Y$_1$-Y$_3$ and, optionally, Y'$_1$-Y'$_3$ residues or to any other optional group e.g. belonging to the hydroxylated pendant arm can be, independently the one another, in a suitable protected form with an appropriate protecting group as above defined, e.g., preferably, in the form of a C$_1$-C$_5$ alkyl ester and, more preferably, of a tert-butyl ester, as is the case in which in the formula (I) R' is C$_1$-C$_5$ alkyl, or may be in the protonated, acid form, when R' is H.

In one preferred aspect, the invention relates to compounds of the formula (I), hence encompassing those of formulas from (III) to (XI), in which the acidic groups are in the protonated form, namely as —COOH, —PO(OH)$_2$, or —PO(R$_4$)(OH) or in the form of a physiologically acceptable salt thereof, or as a derivative of formula —COO$^-$M$^+$, PO$_3^{2-}$2M$^+$, —PR$_4$O$_2^-$M$^+$ in which M$^+$ is a suitable counterion, e.g. a metal ion.

In an alternative embodiment, in the formula (I) one or more R' is C$_1$-C$_5$ alkyl, and the invention relates to compounds according to the above formula (I), and hence encompassing those of formulae from (III) to (X), in which some or even all the acidic groups of the molecule are in the form of a C$_1$-C$_5$ alkyl ester, e.g., methyl, ethyl or tert-butyl ester, finding for instance application as such, or as suitable precursors or intermediate compounds in the preparation of a desired compound of formula (I) or of a suitable paramagnetic complex or salt thereof.

Especially preferred are the compounds of formula (I) selected from the group consisting of:

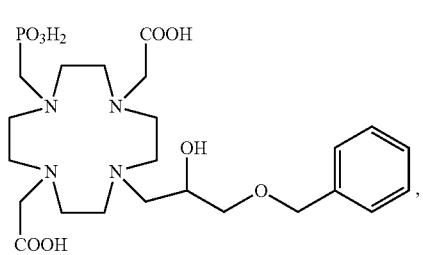

Compound 1

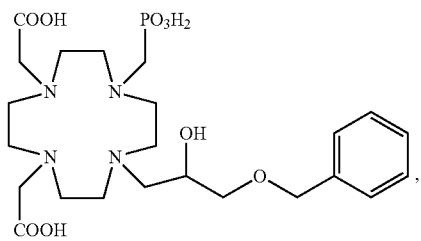

Compound 2

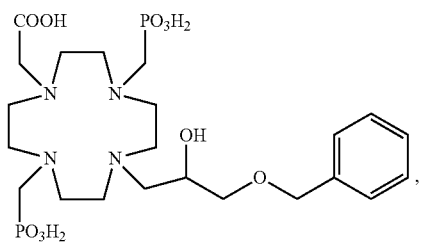

Compound 3

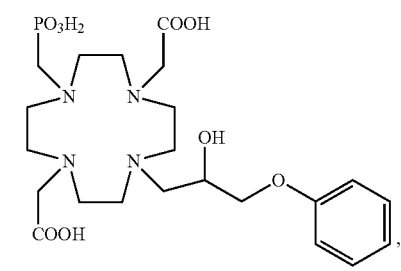

Compound 4

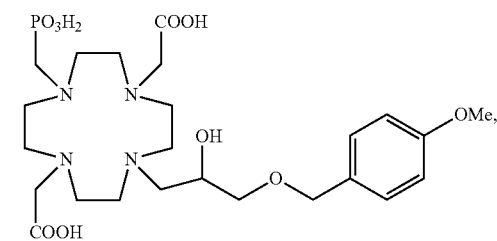

Compound 5

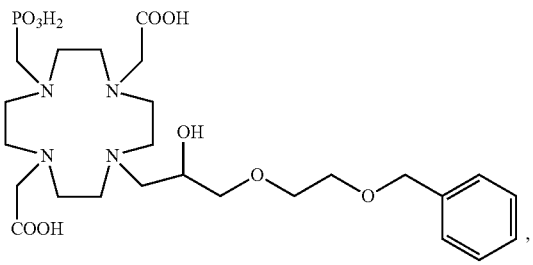

Compound 6

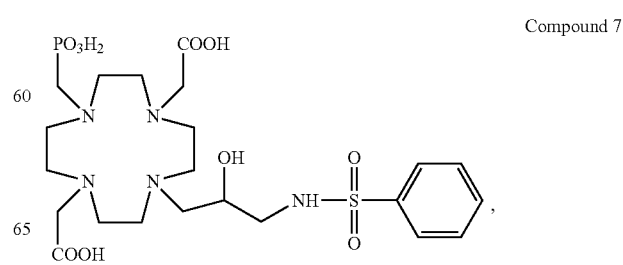

Compound 7

Compound 8
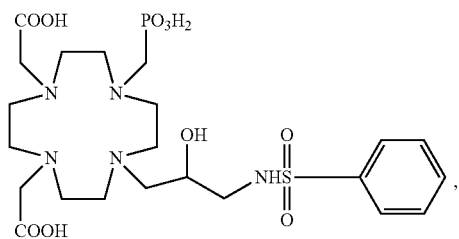
Compound 9
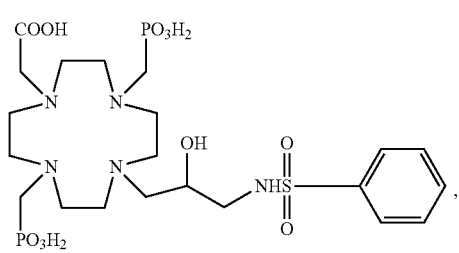
Compound 10
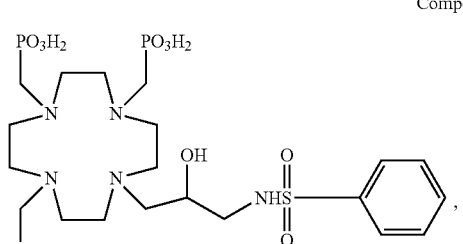
Compound 11
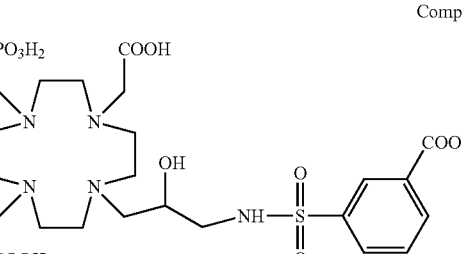
Compound 12
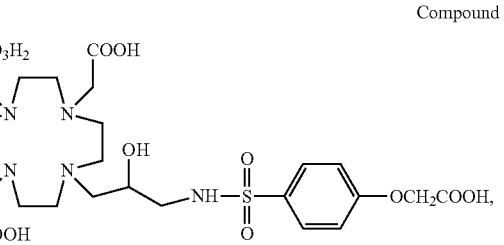
Compound 13
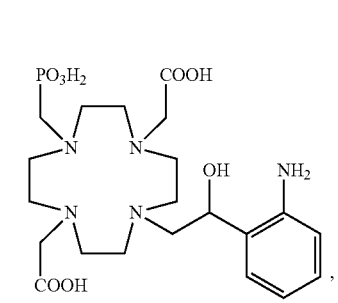
Compound 14
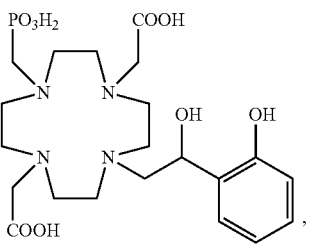
Compound 15
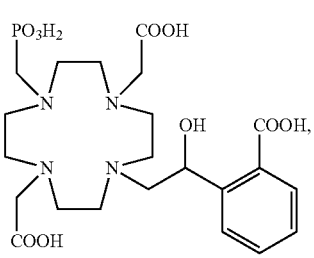
Compound 16
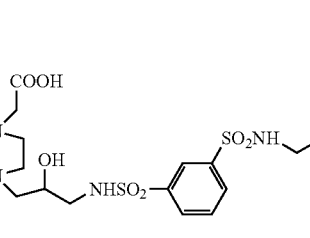
Compound 17
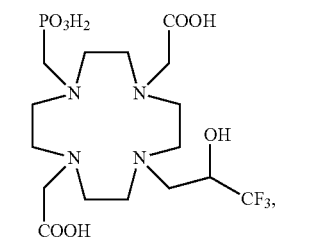
Compound 18
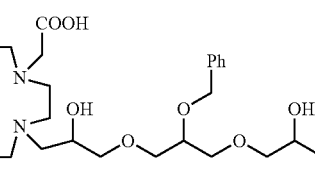
Compound 19
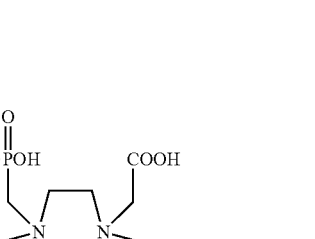

Compound 20
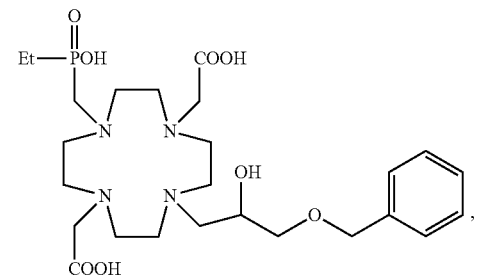

Compound 21
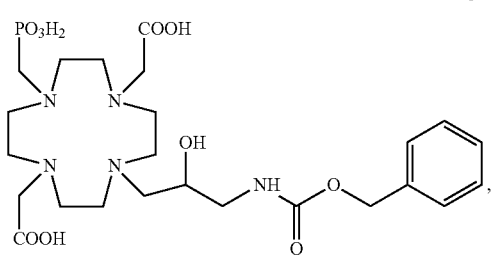

Compound 22
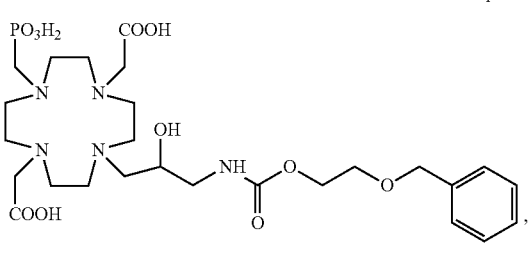

Compound 23
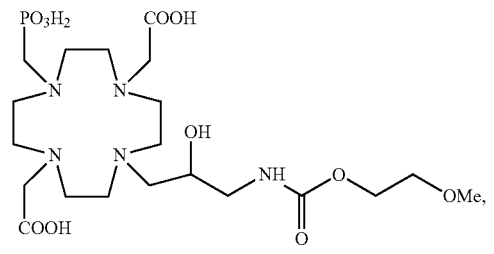

Compound 24
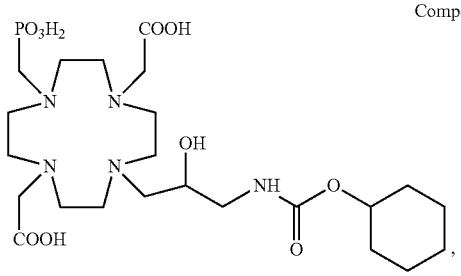

Compound 25
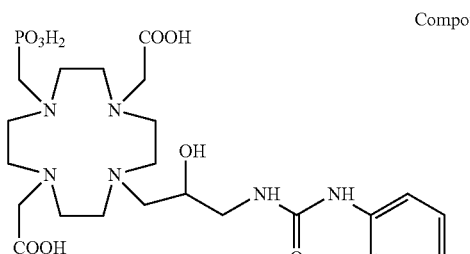

Compound 26
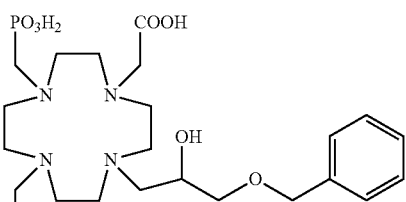

Compound 27
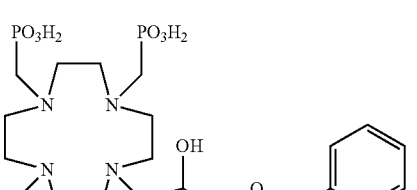

Compound 28
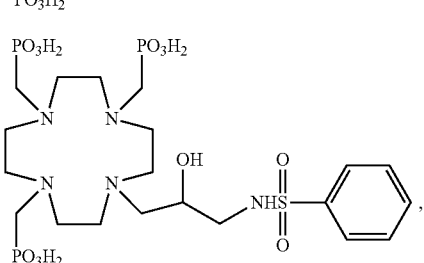

Compound 29
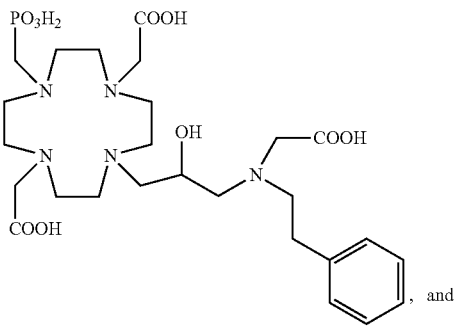

, and

Compound 30
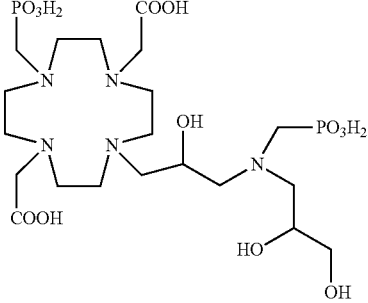

or a physiologically acceptable salt thereof.

In another aspect, the invention relates to the compounds of formula (I) hence encompassing those of formulae from (III) to (XI), in the form of a complex with a paramagnetic metal ion or a radionuclide, or of a suitable salt thereof.

Preferably, the paramagnetic metal ion is selected in the group consisting of Fe(2+), Fe(3+), Cu(2+), Cr(3+), Gd(3+), Eu(3+), Dy(3+), La(3+), Yb(3+) or Mn(2+). More preferably, the paramagnetic metal ion is Gd(3+).

On the other hand, preferred radionuclides providing complexes for use in radiotherapy or radiodiagnostics include $^{105}$Rh, $^{117m}$Sn, $^{44}$Sc, $^{47}$Sc, $^{99m}$Tc, $^{94m}$Tc, $^{203}$Pb, $^{67}$Ga, $^{68}$Ga, $^{72}$As, $^{110}$In, $^{111}$In, $^{113}$In, $^{90}$Y, $^{97}$Ru, $^{60}$Cu, $^{62}$Cu, $^{64}$Cu, $^{52}$Fe, $^{51}$Mn, $^{140}$La, $^{175}$Yb, $^{153}$Sm, $^{166}$Ho, $^{149}$Pm, $^{177}$Lu, $^{186/188}$Re, $^{165}$Dy, $^{166}$Dy, $^{142}$Pr, $^{159}$Gd, $^{211}$Bi, $^{212}$Bi, $^{213}$Bi, $^{214}$Bi, $^{149}$Pm, $^{67}$Cu, $^{198}$Au, $^{199}$Au, $^{82}$Rb, $^{161}$Tb, $^{167}$Tm, and $^{51}$Cr.

As formerly reported, both the compounds of formula (I) of the invention and the paramagnetic chelates thereof can also be in the form of a pharmaceutically acceptable salt, particularly as an addition salt with a physiologically compatible base or acid.

The term "pharmaceutically acceptable salt", as used herein, refers to derivatives of the compounds of the invention wherein the parent compound is suitably modified by converting any of the free acid or basic groups, if present, into the corresponding addition salt with any base or acid conventionally intended as being pharmaceutically acceptable.

Preferred cations of inorganic bases which can be suitably used to prepare a salt of the complexes or the ligands of the invention comprise, for instance, ions of alkali or alkaline-earth metals such as potassium, sodium, calcium or magnesium.

Preferred cations of organic bases comprise, for instance, those of primary, secondary and tertiary amines such as, for instance, ethanolamine, diethanolamine, morpholine, glucamine, N-methylglucamine, N,N-dimethylglucamine.

Preferred anions of inorganic acids which can be suitably used to prepare salts of the complexes of the invention comprise the ions of halo acids, for instance chlorides, bromides or iodides, as well as of other suitable ions such as sulfate.

Preferred anions of organic acids comprise those routinely used in pharmaceutical techniques for the salification preparation of salts of basic substances such as, for instance, acetate, succinate, citrate, fumarate, maleate or oxalate.

Preferred cations and anions of amino acids comprise, for instance, those of taurine, glycine, lysine, arginine, ornithine or of aspartic and glutamic acids.

The preparation of the compounds of formula (I), and of the chelate complexes thereof, either as such or in the form of physiologically acceptable salts, represent a further object of the invention.

Monomeric compounds of formula (I), and the chelated complexes thereof, may be prepared through a general synthetic process comprising the following main steps:
a) Obtaining a macrocyclic substrate 1 in a suitable protected form, e.g. in which the acidic groups of the substrate are protected as tert-butyl esters;
b) Obtaining an alkylating molecule 2, in which any optional functional group(s) not involved with the coupling reaction with the substrate 1 is suitably protected;
c) Coupling the protected substrate 1 with the alkylating molecule 2, to give the desired compound of formula (I) in a suitably protected form or, alternatively, an intermediate thereof 3;
d) Optionally converting the obtained intermediate in the suitably protected compound of formula (I);
e) Removing any protecting group and isolating the chelating ligand of formula (I); and
f) Complexing the obtained ligand with a suitable paramagnetic metal ion and isolating the chelate complex, or the salt thereof.

The single steps of the above general processes, comprehensive of any variant thereof, particularly when referring to the steps of protection/deprotection and activation of known functional groups, may be carried out according to conventional methods known in the art.

Macrocyclic substrates according to the step a) of the process of the invention for instance include the following compounds

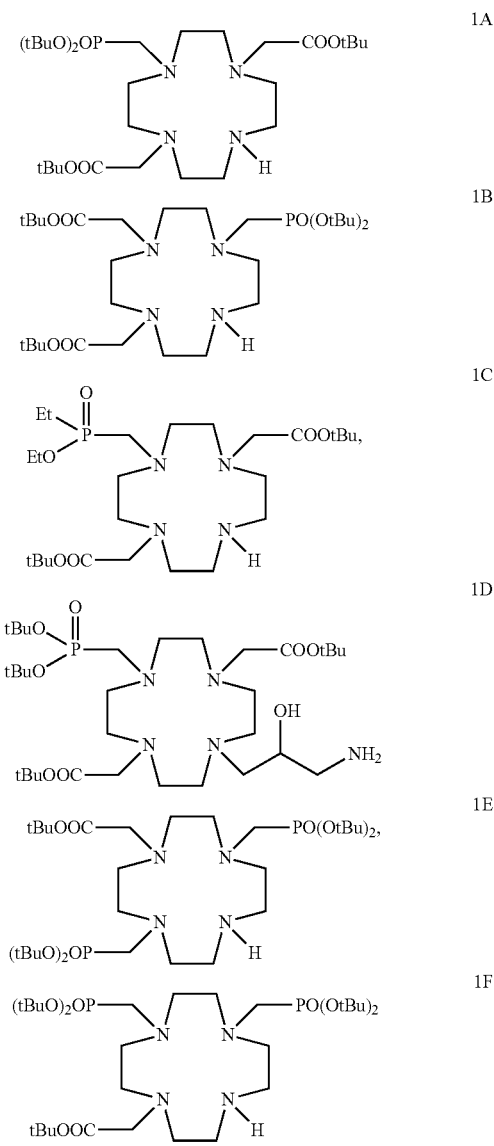

in which all carboxyl, phosphonic or phosphinic groups are suitably protected as tert-butyl esters. These compounds may be obtained for instance as disclosed in WO2005/062828 or may be prepared according to known procedures, for instance as provided in the experimental section.

On the other side, appropriate alkylating molecule 2 for the use of the invention are commercially available, or may easily be prepared according to procedures known to those skilled in the relevant art. Examples of specific procedure for the preparation of protected macrocyclic substrates according to the invention, and of alkylating molecules 2, their coupling, and optional conversion of the obtained intermediates to the desired compounds of formula (I) are moreover provided in the experimental section, together with relevant operational details.

As a general reference on possible protecting groups, and cleavage conditions, e.g. to implement the step e) of the above general synthetic procedure, see the above cited "Greene's protective groups in organic synthesis" Wiley 3$^{rd}$ Ed. Chapters 5 and 7.

The complexation of the compounds of formula (I) e.g. obtained from step f) of former general preparation scheme with a paramagnetic ion and, particularly, with gadolinium, may be performed e.g. by stoichiometric addition of a suitable Gd(III) derivative, particularly a Gd(III) salt or oxide, to a solution of the ligand, e.g. by working according to well-known experimental methods, for instance as reported in EP 230893.

Finally, optional salification of the compounds of the invention may be carried out by properly converting any of the free acidic groups (e.g. carboxylic, phosphonic or phosphinic) or free amino groups into the corresponding pharmaceutically acceptable salts. In this case too, the operative conditions being employed for the optional salification of the compounds of the invention are all within the ordinary knowledge of the skilled person.

Exemplificative implementation of the above general procedure leading to the compounds of the formula (I) and of the chelate complexes thereof, are schematized herein below.

For instance, compounds of the formula (I) may be prepared by using the synthetic procedure schematized in the following Scheme 1

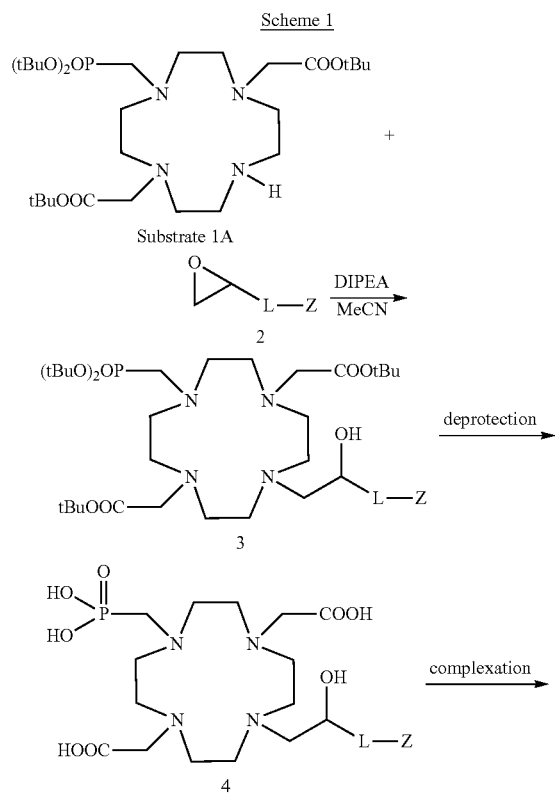

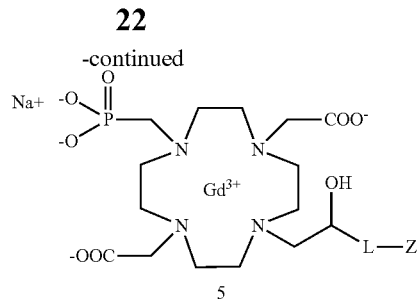

in which a suitable epoxidic derivative of the substituent group Z is reacted with the suitably protected substrate 1A to give the protected ligand of formula (I) that, after cleavage of protecting groups is complexed with the gadolinium metal ion to give the desired Gd complex of formula (I).

Compounds of the formula (I) comprising a phosphinic acid residue on the same nitrogen atom in the position 7 of the macrocycle, or a phosphonic or phosphinic acid residue linked to the nitrogen atom in the position 4 can be obtained in a similar way, respectively by starting from the corresponding substrates 1C and 1B, for instance as schematized in the following Scheme 2

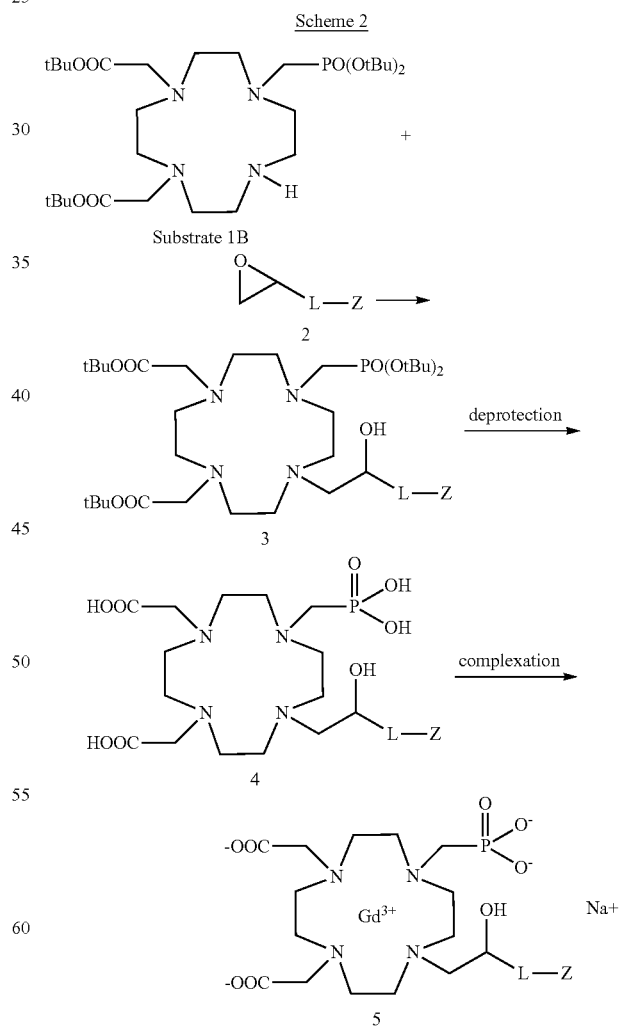

At the same way, compounds of the formula (I) comprising two phosphonic residues appended to two nitrogen atoms of the macrocycle can suitably be obtained by using the same synthetic approach e.g. with substrate compounds 1E and 1F.

Compounds of formula (I) where Z is a suitably substituted aromatic ring such as, for instance, a substituted phenyl group according to the invention directly linked to the hydroxylated carbon atom of the of the macrocycle may, alternatively, be obtained by using the procedure of the following general Scheme 3, where Q represents a substituent group on the ring.

in which an intermediate 3 is obtained by coupling the substrate 1A with the alkylating molecule 2 which is converted by reduction to the protected ligand 4 that, after cleavage of protecting groups is complexed with the gadolinium metal ion to give the desired Gd complex of formula (I) as above discussed.

Compounds according to the invention of formula (VIII) where Z is an alkyl e.g. a methyl substituted by a —N(R$_8$) (R$_9$) group (in which R$_8$ and R$_9$ are as above defined) may suitably be prepared e.g. by following the procedure schematized in the following general Scheme 4, in which —CH$_2$R$_x$ is a group within R$_8$ meanings.

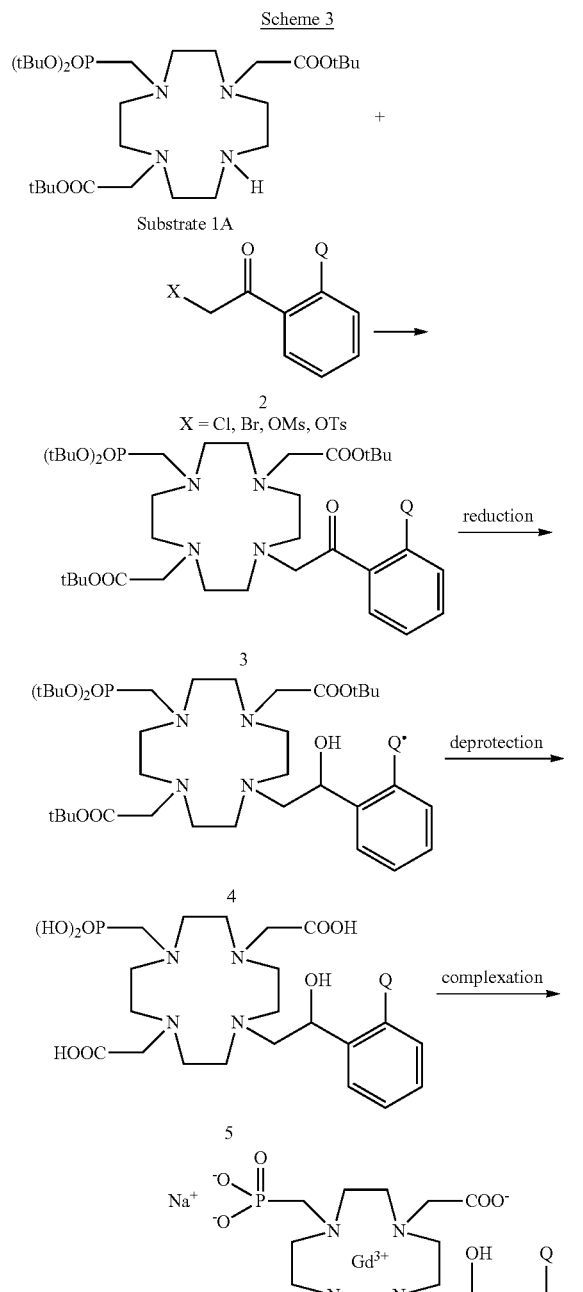

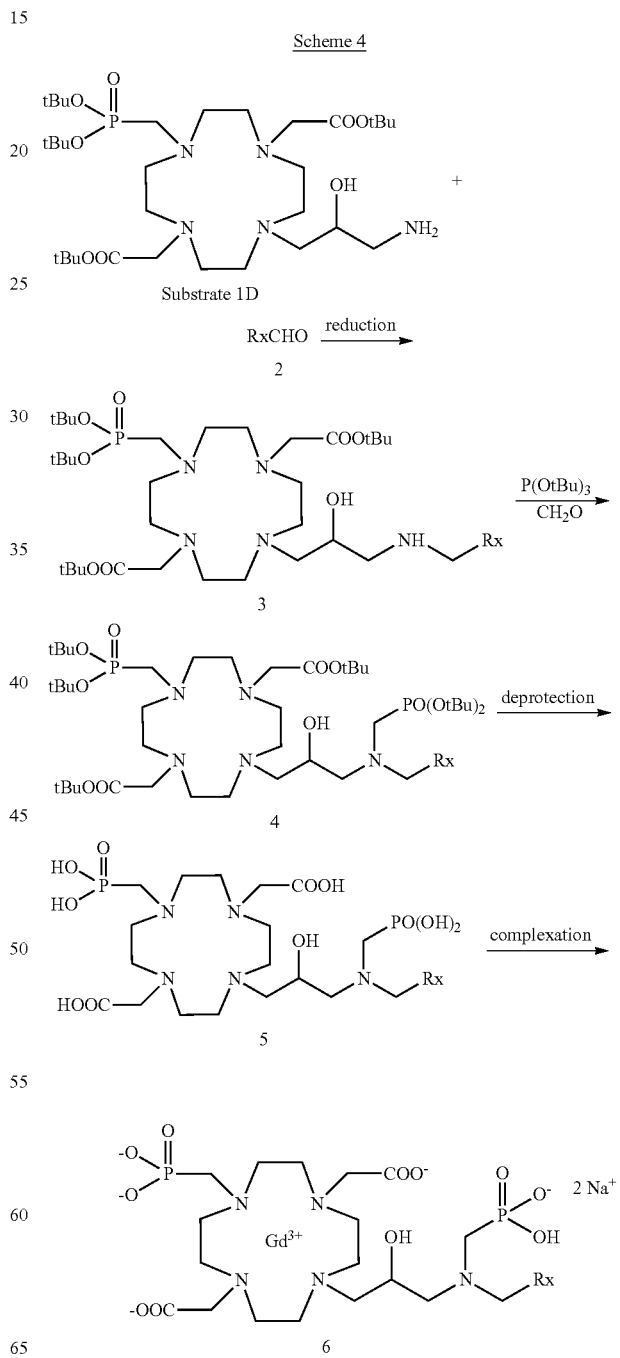

According to this synthetic approach, a suitably protected aminic Substrate 1D

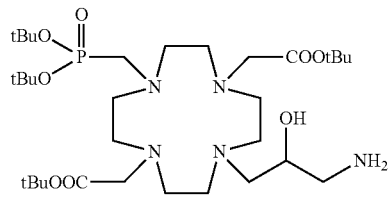

1D is first obtained e.g. as described in better details in the following experimental section, which is then converted to the desired mono- or bis-alkylated derivatives of formula (VIII) by alkylation. For instance, as schematized in the above synthetic Scheme 4, the suitably protected aminic Substrate 1D is first reacted with a $R_8$CHO aldehyde to give a corresponding imino-derivative that, upon reduction, leads to the mono-alkylated derivative 3 having a $R_8$ group appended to the aminic residue of the Substrate 1D. This latter may be suitably deprotected and complexed with the Gadolinium ($Gd^{3+}$) metal ion to give the desired compound of formula (VIII) in which $R_9$ is H, or may be further reacted, for instance with a suitable phosphite, e.g. tri(tert-butyl)phosphite, to give the corresponding bis-alkylated compound 4 in the protected form. By deprotection of all protecting groups the bis-alkylated compound of formula (VIII) is then obtained which may be complexed with the Gadolinium ($Gd^{3+}$) metal ion as above briefly discussed, and isolated as a salt, as provided in better details in the following experimental section.

Still moreover, dimeric compounds according to the invention can suitably be prepared e.g. by using the general procedure of Scheme 5, where X stems for a bridging moiety of formula —W-G-W'-.

Scheme 5

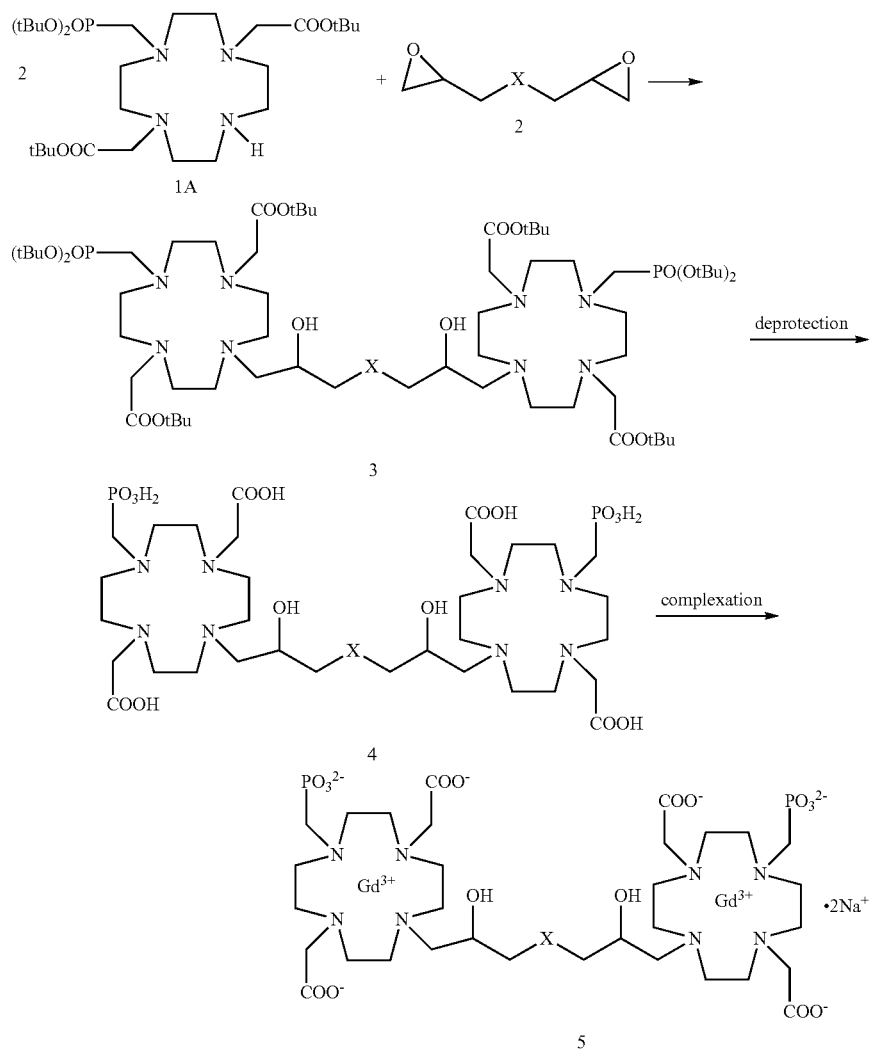

Specific examples of preparation of preferred compounds of formula (I) according to the invention are moreover provided in the following experimental section, constituting a general reference to the operative conditions being employed in the above processes.

The macrocyclic compounds of formula (I) according to the present invention are characterized by comprising a suitable substituent group Z on a hydroxylated pendant arm and one or more phosphonic or phosphinic residue(s) appended to the nitrogen atom(s) of the macrocyclic cage.

The paramagnetic complexes of the identified compounds of the formula (I) of the invention unexpectedly show an improved relaxivity.

In particular, the paramagnetic complex compounds of the invention unexpectedly show a relaxivity $r_{1p}$ value measured in human plasma, at 37° C. and approximatively 1.4 T, which is of at least about 5.5, preferably higher than 6.5, and more preferably, higher than 7.5 $mm^{-1}s^{-1}$.

Although not willing to be bound by any particular theory, the Applicant considers that the relaxivity of the paramagnetic complexes of the compounds of formula (I) may be significantly improved as a result of the combined effect promoted by the peculiar structural components they comprise.

The measured relaxivity is, in particular, significantly increased with respect the relaxivity displayed, under same conditions, by the known MRI contrast agent currently used in the diagnostic daily practice e.g. including the Gd-DOTA, marketed as DOTAREM® and Gd-HPDO3A marketed as ProHance® having analogous macrocyclic chelating cages and comparable molecular weight.

In particular, as shown in Table A of the experimental section, the paramagnetic complex compounds of the invention show relaxivity $r_{1p}$ values which are about 1.5 and up to 2 times higher than corresponding $r_{1p}$ values displayed in human plasma by analogous macrocyclic contrast agents of the market (such as above mentioned DOTAREM® and ProHance®), and will also compare favorably with the analogous compound comprising a phosphonic residue linked to a nitrogen atom of the macrocycle (e.g. the unsubstituted compound disclosed in U.S. Pat. No. 5,316, 757 herein used as Comparative Compound 1) that is, however, devoid of the combined structural components characterizing the compounds of formula (I) of the present invention.

Indeed, a relaxivity $r_{1p}$ value of 4.5 $mM^{-1}s^{-1}$ is obtained for the Comparative 1 in human serum at 37° C. and 1.41 T, that increases, e.g. up to 8.2 and 8.8 $mM^{-1}s^{-1}$, under same conditions, respectively for the Chelate Complex 7, comprising a sulfonamide residue appended to the hydroxylated carbon atom, and Chelate Complex 21 having a carbamate residue in the same position.

Advantageously, the high relaxivity displayed by the agents of the invention may allow reducing their diagnostically effective dose, as compared to current contrast agents in diagnostic daily practice.

The Applicant has further observed that the phosphonic or phosphinic residue(s) appended to the nitrogen atom(s) of the macrocyclic compounds of the invention may also contribute to increase the solubility in water of corresponding paramagnetic complexes, thus allowing to obtain physiologically acceptable aqueous formulations of the same, suitable for use in diagnostic imaging of human patients, that may be otherwise be hardly obtainable with corresponding carboxylic complexes.

Paramagnetic complexes and, especially, gadolinium complexes of the compounds of formula (I), or the pharmaceutical acceptable salt thereof, thus find advantageous use in the preparation of pharmaceutical formulations intended for a general use in the diagnostic imaging of a human or animal body organ, tissue or region either in vivo or in vitro, ex vivo.

When referring hereinafter to the various uses and applications of the compounds of formula (I) it is intended that such uses and applications may well apply to any specific embodiments of such compounds illustrated herein.

According to an additional aspect, the invention relates to the use of the compounds of formula (I) in the form of complexes with a paramagnetic metal ion and, especially, gadolinium, or of a pharmaceutical acceptable salt thereof, for the preparation of a pharmaceutical formulation for use in the diagnostic imaging, either in vivo or in vitro, ex vivo, of a human or animal body organ, tissue or region or of a biological sample, including cells, biological fluids and biological tissues originating from a live mammal patient, and preferably, human patient, by use of the MRI technique.

A further aspect of the invention concerns a pharmaceutical composition for diagnostic use comprising a compound of formula (I) in the form of a paramagnetic metal complex or of a pharmaceutical salt thereof, in admixture with one or more physiologically acceptable excipients, diluents or solvents. Preferably, the pharmaceutical composition is a contrast-producing composition and, more preferably, a MRI contrast producing composition comprising at least one Gd-complex according to the invention.

In an additional aspect the invention relates to a MRI contrast medium comprising n effective amount of at least one chelated compound according to the invention and, especially, of a gadolinium complex of the formula (I), or of a pharmaceutical acceptable salt thereof, in combination with one or more pharmaceutically acceptable excipients, diluents or solvents.

To this extent, and unless otherwise provided, the term "effective amount" or "effective dose", as used herein, refers to any amount of a paramagnetic chelated complex of the formula (I) according to the invention or pharmaceutical composition thereof, that is sufficient to fulfil its intended diagnostic purpose(s): i.e., for example, to visualize a biological element including cells, biological fluids and biological tissues as well as body organs, tissues or regions of a patient.

Unless otherwise indicated, with "individual patient" or "patient" as used herein we refer to a living human or animal patient, and, preferably a human being undergoing MR diagnostic assessment.

On the other side, details concerning dosages, dosage forms, modes of administration, pharmaceutical acceptable carriers, diluent, excipients, adjuvants and the like are known in the art.

Advantageously, due to the increased relaxivity, the paramagnetic complexes according to the invention may be administered at a generally lower dosage with respect to commercial MRI contrast agents.

For instance, satisfactory diagnostic MRI images, providing a physician with adequate diagnostic support, may be obtained with doses of the gadolinium complex compounds identified by the present invention of about 90%, more preferably 80%, and up to 60% of the dose of MRI contrast agent used in the daily practice, which for adult patients is of about 0.2 mL/kg of body weight.

Suitable pharmaceutical composition according to the invention may be prepared in accordance with routine procedures as a pharmaceutical composition adapted for administration to human being.

From all the foregoing it can be easily envisaged that the selection of paramagnetic complex compounds of formula (I) identified by the present invention have a wide range of applications as they can be used for intravasal, (for instance intravenous, intraarterial, intracoronaric, intraventricular administration and the like), intrathecal, intraperitoneal, intralymphatic and intracavital administrations. Furthermore, they are suitable for the oral or parenteral administration and, therefore, specifically for the imaging of the gastrointestinal tract.

For instance, for parenteral administration they can be preferably formulated as sterile aqueous solutions or suspensions, whose pH can range from 6.0 to 8.5.

These formulations can be lyophilized and supplied as they are, to be reconstituted before use.

For the gastrointestinal use or for injection in the body cavities, these agents can be formulated as a solution or suspension optionally containing suitable excipients in order, for example, to control viscosity.

The solutions or suspensions of the compounds of this invention can also be formulated as aerosol to be used in aerosol-bronchography and instillation. For example, they can be also encapsulated into liposomes or even constitute the liposomes themselves, as set forth above, and thus can be used as uni- or multi-lamellar vesicles.

In a preferred aspect, pharmaceutical compositions according to the invention are properly formulated in isotonic sterile aqueous, optionally buffered, solutions for parenteral administration, and most preferably for intravenous or intra-arterial administration.

More preferably, the said diagnostic composition has a concentration of the paramagnetic complex of the formula (I) of from 0.002 and 1.0 M and is supplied, for instance as a bolus, or as two or more doses separated in time, or as a constant or non-linear flow infusion.

In a further aspect, the invention relates to the use of a pharmaceutical composition including a paramagnetic chelated complex of the formula (I) according to the invention or pharmaceutical acceptable salt thereof for the diagnostic imaging, both in vitro (ex vivo) and in vivo, of pathological systems, including cells, biological fluids and biological tissues originating from a live mammal patient, and preferably, human patient, as well as of human body organ, regions or tissues, as well as for monitoring the progress and results of therapeutic treatment of the said pathologies.

In an additional aspect, the present invention concerns a method for the in vivo imaging a body organ, tissue or region by use of the MRI technique, said method comprising using a pharmaceutical composition comprising a paramagnetic chelated complex of the formula (I) according to the invention, or a physiological acceptable salt thereof.

In one embodiment, said MRI imaging method comprises administering to a human or animal patient in need of the diagnostic assessment a diagnostically effective amount of a composition of the invention comprising a compound of formula (I) in the form of complex with a paramagnetic metal ion, and, preferably, with the $Gd^{3+}$ metal ion and then subjecting the administered or pre-administered patient to a diagnostic imaging by use of the MRI technique.

According to a particularly preferred embodiment, the above MRI method is performed on human or animal bodies suitably pre-administered with a diagnostically effective amount of a composition of the invention as above defined.

More particularly, according to a preferred embodiment the present invention refers to a method for the in vivo imaging a human or animal body organ or tissue by use of the MRI technique that comprises the steps of:

a) submitting a human or animal pre-administered with a composition of the invention comprising a compound of formula (I) in the form of a paramagnetic complex, or of a pharmaceutically acceptable salt thereof, and positioned in a MRI imaging system, to a radiation frequency selected to excite the non-zero proton spin nuclei of the active paramagnetic substrate; and b) recording a MR signal from said excited nuclei.

In yet another aspect the invention provides a method for the in vitro (ex vivo) imaging of biological samples, including cells, biological fluids and biological tissues originating from a live mammal patient, and preferably, human patient, by use of the MRI technique, that comprises contacting an effective amount of a paramagnetic complex compound of formula (I), or of a physiologically acceptable salt thereof, with the biological sample of interest and then obtaining MRI signals from said samples r by use of the MRI technique.

Non-limiting examples of preferred compounds of the invention and intermediates for their preparation is reported in the following section, aimed to illustrate the invention in greater detail without limiting its scope.

Experimental Part

Example 1: Preparation of Substrate Compound 1A

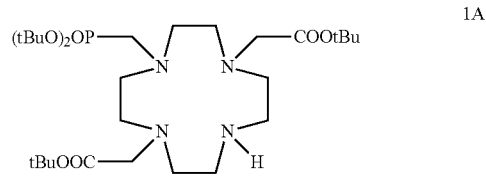

1A

The preparation of the starting compound 1A was obtained by using the procedure reported in WO2005/062828, according to the following synthetic Scheme 6.

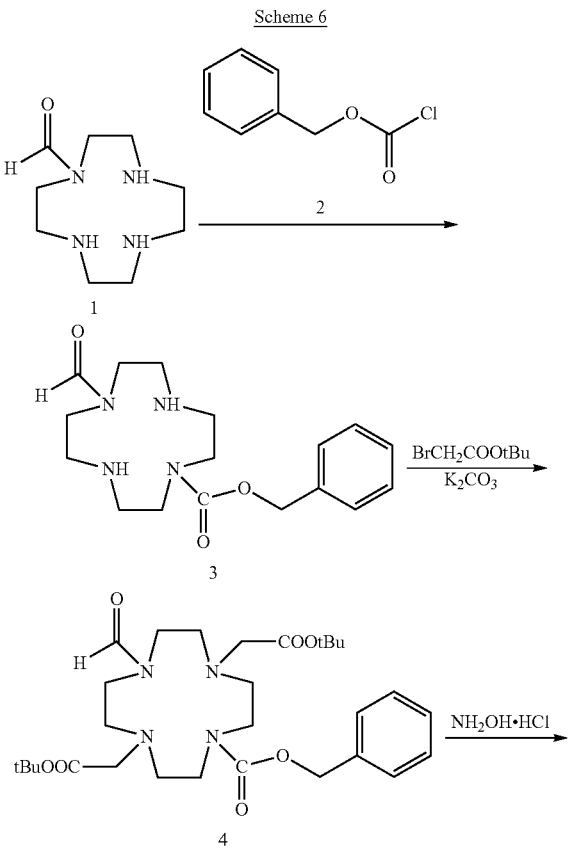

Scheme 6

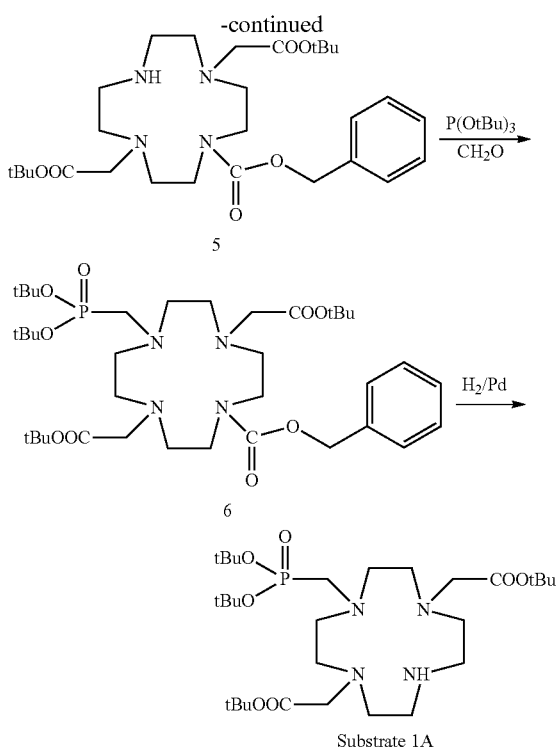

Substrate 1A

Example 2: Preparation of the Substrate Compound 1B

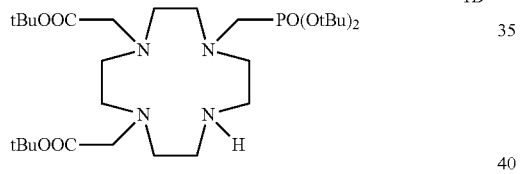

The preparation of the starting compound 1B was obtained using the procedure reported in the following synthetic Scheme 7.

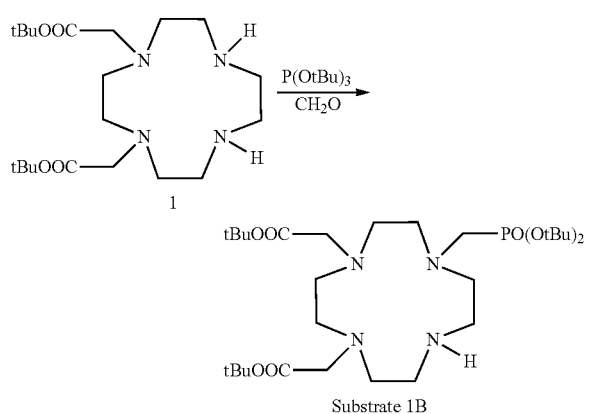

Substrate 1B

A mixture of compound 1 (prepared as reported in *J. Org. Chem.* 2003, 68, 2956-2959) (20 g; 50 mmol), paraformaldehyde (1.5 g; 50 mmol) and tris(t-butyl) phosphite (12.5 g; 50 mmol) (prepared as reported in *Tetrahedron Lett.* 2005, 46, 4707-4710) was heated at 70° C. for 16 h. After this time more paraformaldehyde (0.3 g; 10 mmol) and tris(t-butyl) phosphite (2.5 g; 10 mmol) were added and the mixture was heated for additional 16 h. The mixture was evaporated under vacuum to a residue that was purified by flash-chromatography (eluent: gradient of $CH_2Cl_2$/MeOH) to obtain Substrate 1B (10.6 g). Yield 35%. 1H-NMR, 13C-NMR, 31P-NMR and mass spectrum were consistent with the expected structure.

Example 3: Preparation of the Substrate Compound 1C

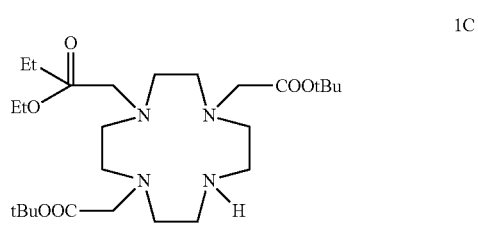

The preparation of the starting compound 1C was obtained using the procedure reported in the following synthetic Scheme 8.

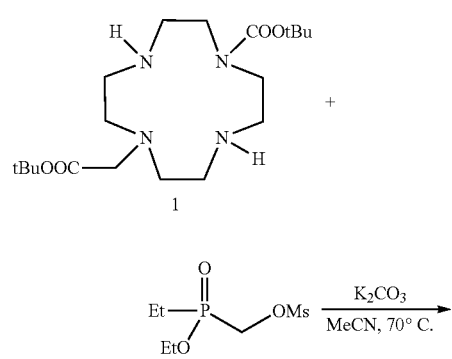

Substrate 1C

A mixture of compound 1 (prepared as reported in *Synthesis* 1997, 759-763) (20 g; 50 mmol), compound 2 (prepared as reported in *Tetrahedron Lett.* 2013, 54, 6378-6380) (11.5 g; 50 mmol) and $K_2CO_3$ (13.8 g; 100 mmol) in acetonitrile (250 mL) was stirred and heated at 70° C. for 16 h. The mixture was filtered then evaporated under vacuum to a residue that was purified by flash-chromatography (eluent: gradient of $CH_2Cl_2$/MeOH) to obtain Substrate 1C (8.55 g). Yield 32%.

1H-NMR, 13C-NMR, 31P-NMR and mass spectrum were consistent with the expected structure.

Example 4: Preparation of the Substrate Compound 1D

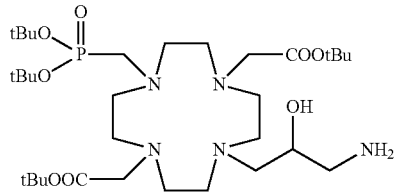

1D

The preparation of the starting compound was obtained by using the following synthetic Scheme 9.

(200 mL), washed with water (4×50 mL), brine (4×50 mL) and evaporated. The residue was purified by flash-chromatography on silica gel (eluent $CH_2Cl_2/MeOH=25:1$ then 9:1) to give intermediate 3 (40.8 g). Yield: 74%.

1H-NMR, 13C-NMR, 31P-NMR and mass spectrum were consistent with the expected structure.

c) Deprotection

Intermediate 3 (55.17 g; 0.0764 mol) was dissolved in MeOH (200 mL) and 5% palladium on carbon (2.2 g) was added. The mixture was hydrogenated at ambient temperature and pressure for 4 h then was filtered and the solution evaporated to give the substrate compound 1D (45 g). Yield: 100%.

1H-NMR, 13C-NMR, 31P-NMR and mass spectrum were consistent with the expected structure.

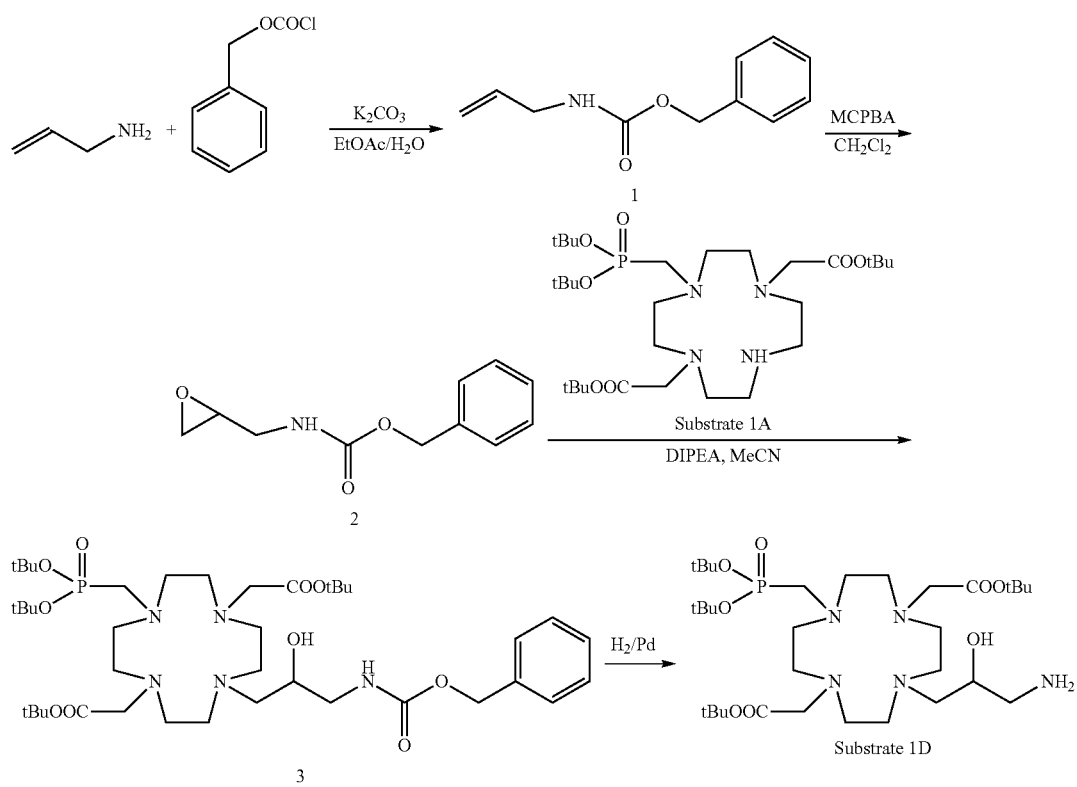

Scheme 9 a) Preparation of the compound 2

Compound 1 has been synthesized as reported in *J. Org. Chem.* 1988, 53, 3457-3465.

Compound 2 has been synthesized as reported in WO2008/126034.

b) Preparation of the intermediate 3

Epoxide 2 (20.7 g; 0.10 mol) was added to a solution of the substrate 1A (obtained as described in WO2005/062828) (41.4 g; 0.034 mol) in acetonitrile (300 mL) and N,N-diisopropylethylamine (DIPEA) (35.4 ml; 2.10 mol). The reaction mixture was heated at 60° C. for 48 h and then evaporated. The obtained residue was dissolved in EtOAc Example 5: Preparation of the Substrate Compound 1E

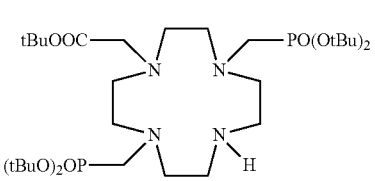

1E

The preparation of the starting compound was obtained by using the following synthetic Scheme 10.

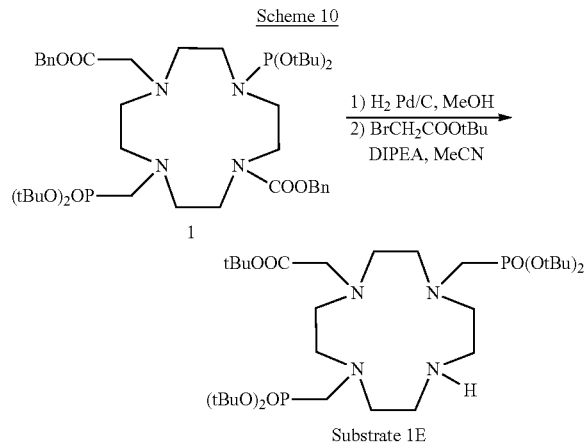

Scheme 10

A solution of compound 1 (prepared as reported in *Tetrahedron Lett.* 2005, 46, 4707-4710) (26 g; 30.5 mmol) in MeOH (250 mL) was added with 5% palladium on carbon (5 g) and hydrogenated at room pressure and temperature for 8 h. The catalyst was filtered and the solution evaporated to a residue. This latter was then dissolved in acetonitrile (250 mL) and to this solution t-butyl bromoacetate (5.85 g; 30 mmol) and N,N-diisopropylethylamine (DIPEA) (3.88 g; 30 mmol) were added. The reaction mixture was stirred for 48 h and then evaporated. The residue was purified by flash-chromatography on silica gel (eluent: gradient CH$_2$Cl$_2$/MeOH) to give Substrate 1E (5.76 g). Yield: 27%.

1H-NMR, 13C-NMR, 31P-NMR and mass spectrum were consistent with the expected structure.

Example 6: Preparation of the Substrate Compound 1F

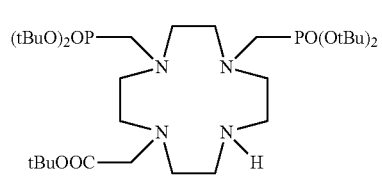

1F

The preparation of the starting compound was obtained by using the following synthetic Scheme 11.

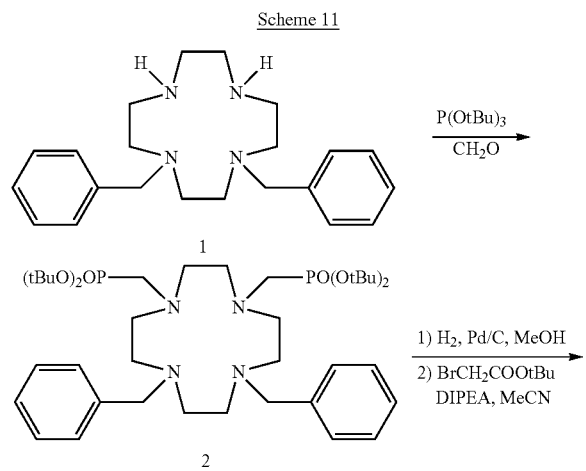

Scheme 11 a) Preparation of Compound 2

A mixture of compound 1 (prepared as reported in Tetrahedron 2004, 60, 5595-5601) (17.6 g; 50 mmol), paraformaldehyde (3 g; 100 mmol) and tris(t-butyl) phosphite (25 g; 100 mmol) (prepared as reported in *Tetrahedron Lett.* 2005, 46, 4707-4710) was heated at 60° C. for 24 h. After this time more paraformaldehyde (0.6 g; 20 mmol) and tris(t-butyl) phosphite (5 g; 20 mmol) were added and the mixture was heated for 24 h. The mixture was evaporated under vacuum to a residue that was purified by flash-chromatography (eluent: gradient of CH$_2$Cl$_2$/MeOH) to obtain compound 2 (16.4 g). Yield 43%.

1H-NMR, 13C-NMR, 31P-NMR and mass spectrum were consistent with the expected structure.

b) Preparation of Substrate 1F

A solution of intermediate 2 (15 g; 19.6 mmol) in EtOH (200 mL) was added with 10% palladium on carbon (1.5 g) and hydrogenated at room pressure and temperature for 16 h. The catalyst was filtered and the solution evaporated to a residue. This latter was then dissolved in acetonitrile (250 mL) and to this solution t-butyl bromoacetate (3.7 g; 19 mmol) and N,N-diisopropylethylamine (DIPEA) (5.2 g; 40 mmol) were added. The reaction mixture was stirred for 48 h and then evaporated. The residue was purified by flash-chromatography on silica gel (eluent: gradient CH$_2$Cl$_2$/MeOH) to give Substrate 1F (5.2 g). Yield: 38%.

1H-NMR, 13C-NMR, 31P-NMR and mass spectrum were consistent with the expected structure.

Example 7: Preparation of the Comparative Compound 1

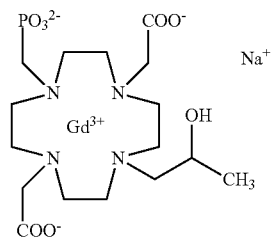

The preparation of the Comparative Compound 1 is obtained by using the following synthetic scheme 12

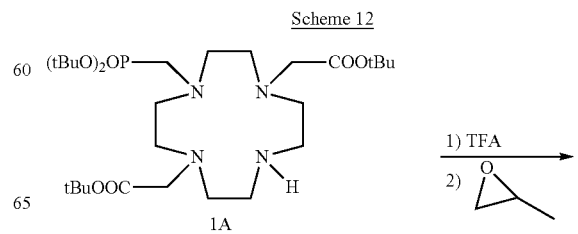

Scheme 12

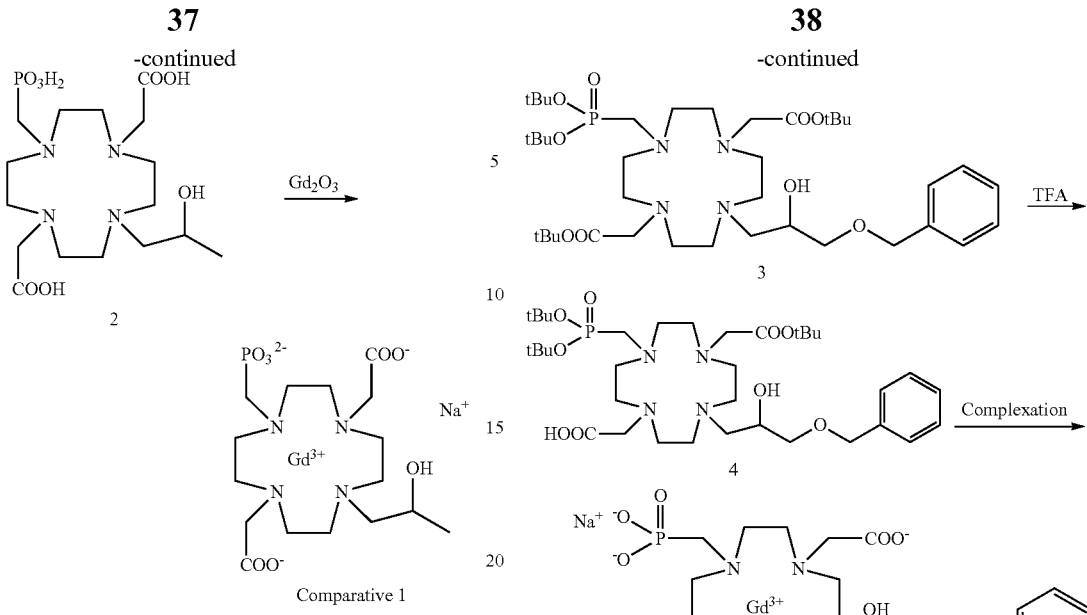

Comparative 1 a) Preparation of Compound 2

Trifluoroacetic acid (10 mL) was added to a solution of substrate 1A (2.76 g; 4.5 mmol) in dichloromethane (20 mL) at 0° C. The mixture was stirred for 6 h at room temperature then evaporated; the residue was dissolved in TFA (20 mL) and the mixture was stirred at room temperature for 16 h, then evaporated. The residue was dissolved in water (30 mL) and propylene oxide (0.38 g; 6.5 mmol) was added then 1M NaOH was added until pH 11. The mixture was heated at 40° C. for 8 h then at room temperature for 16 h. The mixture was evaporated and the residue purified by elution first on a Sephadex G10 column (eluent: water) then on an Amberchrom CG161M column (eluent: gradient water/acetonitrile) obtaining the chelating ligand 2 as a solid (1.12 g). Yield 57%.

1H-NMR, 13C-NMR, 31P-NMR and mass spectrum were consistent with the expected structure.

b) Complexation

Gadolinium oxide (0.87 g; 2.4 mol) was added to a solution of ligand 2 (2.1 g; 4.77 mol) in water (50 mL) and the obtained mixture was stirred and heated at 55° C. for 24 h and at 70° C. for 12 h. The cloudy solution was filtered on Millipore HA 0.45 μm and the filtrate was purified on a Sephadex G10 column (eluent: water) obtaining the Comparative Compound 1 as a solid (2.88 g). Yield 98%.

Mass spectrum and elemental analysis were consistent with the expected structure.

Example 8: preparation of the Chelate Complex 1

The preparation of the Chelate Complex 1 was obtained by using the following synthetic Scheme 13.

Scheme 13

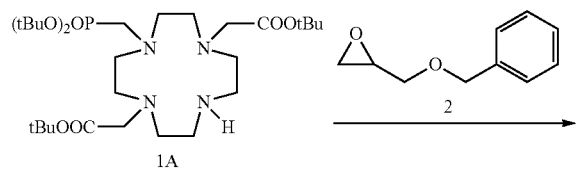

a) Preparation of Intermediate 3

Commercially available benzyl glycidyl ether 2 (5.8 g; 0.035 mol) was added to a solution of the substrate 1A, obtained as reported in Example 1, (18.5 g; 0.03 mol) in MeCN (150 mL) and N,N-diisopropylethylamine (DIPEA) (16 mL). The mixture was heated to 60° C. for 72 h, then evaporated. The residue was dissolved in EtOAc (200 mL) and the solution was washed with water (4×50 mL), brine (4×50 ml), then evaporated. The crude was purified by flash-chromatography on silica gel (eluent: gradient $CH_2Cl_2$/MeOH) to give intermediate 3 (11.7 g). Yield: 51%.

1H-NMR, 13C-NMR, 31P-NMR and mass spectrum were consistent with the expected structure.

b) Deprotection

Trifluoroacetic acid (10 mL) was added to a solution of the intermediate 3 (11.7 g; 0.015 mol) in dichloromethane (50 mL). The solution was then evaporated and the residue dissolved in trifluoroacetic acid (30 mL) and tris-isopropylsilane (0.1 mL). The mixture was stirred at room temperature for 24 h then was diluted with ethyl ether (400 mL) to give a solid that was filtered, washed with ethyl ether and dried. The obtained crude product was dissolved in water (30 mL) and purified by chromatography on Amberchrome CG161M column (eluent: gradient water/MeCN), to give the desired compound 4 (4.2 g).Yield: 51%.

1H-NMR, 13C-NMR, 31P-NMR and mass spectrum were consistent with the expected structure.

c) Complexation

Gadolinium oxide (296 mg; 0.85 mmol) was added to a solution of compound 4 (962 mg; 1.7 mmol) dissolved in water (20 mL) and the mixture was stirred and heated to 90° C. After one hour, the cloudy solution was filtered on Millipore HA 0.45 μm, concentrated and purified by chromatography on Amberchrome CG161M column (eluent: gradient water/MeCN) to give the complex compound 1 as a solid (1.05 g). Yield: 89%.

Title 99.3% (HPLC, area %)

Mass spectrum and elemental analysis were consistent with the expected structure.

The Chelate Complex 2 was analogously prepared following the same synthetic strategy and employing substrate compound 1B (synthesized as reported in Example 2).

The Chelate Complex 3 was analogously prepared following the same synthetic strategy and employing substrate compound 1E (synthesized as reported in Example 5).

The Chelate Complex 4 was analogously prepared by using the substrate compound 1A and 1,2-epoxy-3-phenoxypropane (commercially available e.g. from Sigma-Aldrich catalogue) and following the same synthetic strategy.

The Chelate Complex 5 was analogously prepared by using the substrate compound 1A and 4-methoxybenzyl glycidol ether (prepared as reported in *Tetrahedron Lett.* 2014, 55, 4054-4056) and following the same synthetic strategy.

The Chelate Complex 6 was analogously prepared following the same synthetic strategy and employing substrate compound 1A with 2-((2-(benzyloxy)ethoxy)methyl)oxirane (prepared as reported in *Synlett* 2015, 26, 1977-1980).

The Chelate Complex 17 was analogously prepared following the same synthetic strategy and employing substrate compound 1A and 3,3,3-trifluoro-1,2-epoxypropane (commercially available).

The Chelate Complex 20 was analogously prepared following the same synthetic strategy and employing substrate compound 1C (synthesized as reported in Example 3).

The Chelate Complex 26 was analogously prepared following the same synthetic strategy and employing substrate compound 1F (synthesized as reported in Example 6).

Example 9: Preparation of the Chelate Complex 7

The preparation of the starting compound was obtained by using the following synthetic Scheme 14.

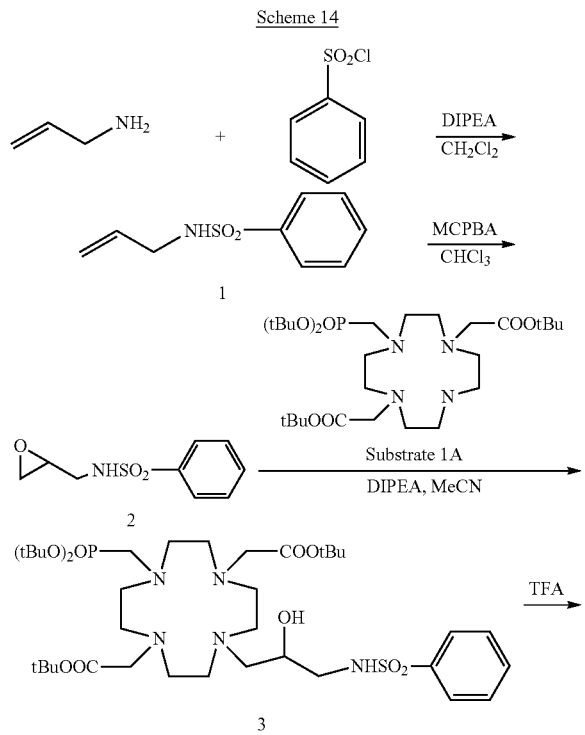

Scheme 14

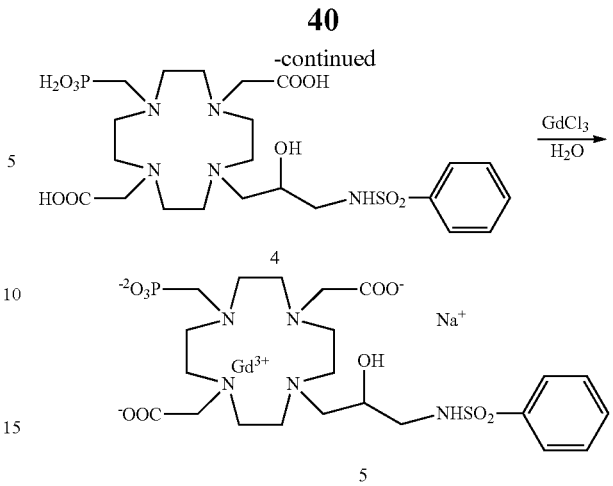

a) Preparation of Intermediate 1

A solution of benzenesulfonyl chloride (35.3 g; 0.20 mol) in dichloromethane (100 mL) was slowly added to a stirred solution of allylamine (12.5 g; 0.22 mol) and DIPEA (42.5 g; 0.33 mol) in dichloromethane (250 mL) at 0° C. The solution was stirred at 20° C. for 2 h then washed with water (100 mL), 1N HCl until acidic pH, water (100 mL) and brine (100 mL). The solution was evaporated to give compound 1 (40.2 g) as residue. Yield: 93%. 1H-NMR, 13C-NMR, and mass spectrum were consistent with the expected structure.

b) Preparation of Intermediate 2

A solution of 3-chloroperbenzoic acid (29.5 g; 0.120 mol) in chloroform (150 mL) was added dropwise to a solution of compound 1 (20.0 g; 0.10 mol) in chloroform (150 mL) and the mixture was stirred for 18 h. Then the solution was washed with 5% aq. NaHCO$_3$ until basic pH, with water (200 mL), with brine (100 mL), dried with Na$_2$SO$_4$ and concentrated to an oily residue. The crude product was purified by chromatography on silica gel (eluent: gradient CH$_2$Cl$_2$/EtOAc) to give compound 2 (19.0 g). Yield: 89%. 1H-NMR, 13C-NMR, and mass spectrum were consistent with the expected structure.

c) Preparation of the intermediate 3

A mixture of substrate 1A, obtained as described in Example 1, (23.9 g; 0.039 mol), compound 2 (9.8 g; 0.046 mol) and N,N-diisopropylethylamine (DIPEA) (21 mL) in MeCN (200 mL) was stirred at 60° C. for 72 h. The solution was concentrated to a residue which was dissolved in EtOAc (200 mL). The solution was washed with water (4×50 mL), brine (4×50 mL) and evaporated to a residue which was purified by flash-chromatography on silica gel (eluent: gradient CH$_2$Cl$_2$/MeOH) to give compound 3 (23.5 g). Yield: 73%.

1H-NMR, 13C-NMR, 31P-NMR and mass spectrum were consistent with the expected structure.

d) Deprotection

Trifluoroacetic acid (30 mL) was added to a solution of the intermediate 3 (23.5 g; 0.029 mol) in dichloromethane (150 mL) at 0° C. The solution was then evaporated and the residue dissolved in trifluoroacetic acid (90 mL) and tris-isopropylsilane (0.2 mL). The mixture was stirred at room temperature for 48 h then was diluted with ethyl ether (600 mL) to give a solid that was filtered, washed with ethyl ether and dried. The obtained crude product was dissolved in water (30 mL) and purified by chromatography on Amberchrome CG161M column (eluent: gradient water/MeCN), to give compound 4 (8.8 g).Yield: 51%.

1H-NMR, 13C-NMR, 31P-NMR and mass spectrum were consistent with the expected structure.

e) Complexation

A solution of gadolinium chloride hexahydrate (1.486 g; 4.0 mmol) in water (20 mL) was added to a solution of compound 4 (2.53 g; 4.0 mmol) in water (50 mL). The pH was raised to 8 with 2N NaOH; the stirred solution was heated to 50° C. then neutralized to pH 7 with 1N HCl and finally purified by chromatography on Amberchrome CG 161M column (eluent: water/MeCN =9:1) to give the gadolinium complex 5 (3.0 g). Yield: 97%. HPLC purity: 99.7%.

Mass spectrum and elemental analysis were consistent with the expected structure.

The Chelate Complex 8 was analogously prepared following the same synthetic strategy and employing substrate compound 1B (synthesized as reported in Example 2).

The Chelate Complex 9 was analogously prepared following the same synthetic strategy and employing substrate compound 1E (synthesized as reported in Example 5).

The Chelate Complex 10 was analogously prepared following the same synthetic strategy and employing substrate compound 1F (synthesized as reported in Example 6).

Example 10: Preparation of the Chelate Complex 11

The preparation of the starting compound was obtained by using the following synthetic Scheme 15.

Scheme 15

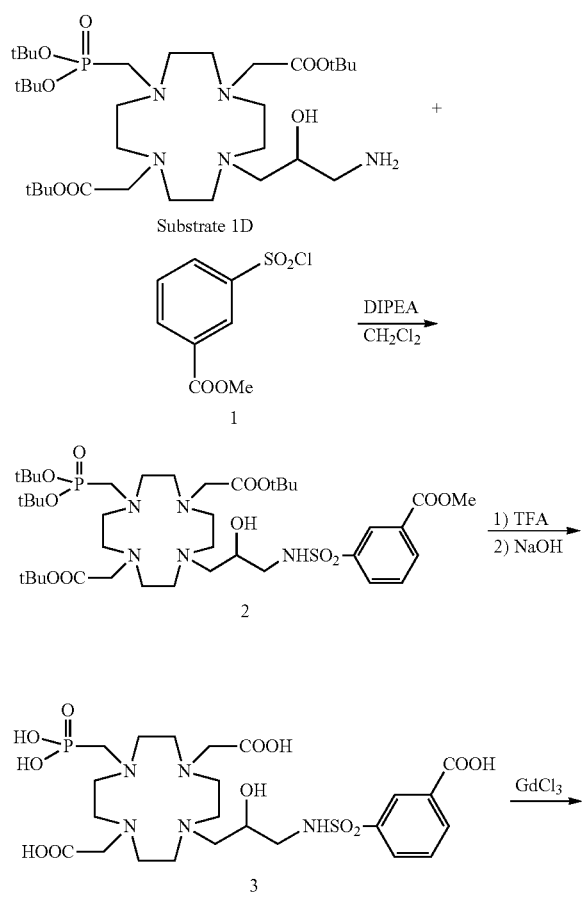

-continued

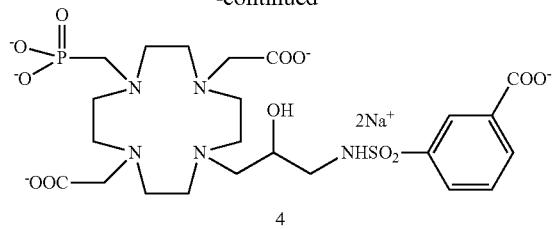

4 a) Preparation of compound 2

A solution of methyl 3-(chlorosulphonyl)benzoate 1 (obtained as reported in *J. Med. Chem.* 2007, 50, 442-454) (4.12 g; 17.6 mmol) in $CH_2Cl_2$ (20 mL) was slowly added to a solution of Substrate 1D (obtained as described in Example 4) (10 g; 14.7 mmol) and N,N-diisopropylethylamine (DIPEA) (5 mL) in $CH_2Cl_2$ (150 mL) at −8° C. At the end of the addition the temperature was raised to 20° C. and the mixture was stirred for 16 h. The solution was washed with water (3×50 mL), brine (2×50 mL) then the organic phase was dried ($Na_2SO_4$) and evaporated to residue. The crude was purified by flash chromatography on silica gel (eluent: gradient of $CH_2Cl_2$/MeOH) to give compound 2 (12 g). Yield: 93%.

1H-NMR, 13C-NMR, 31P-NMR and mass spectrum were consistent with the expected structure.

b) Deprotection

Trifluoroacetic acid (5 mL) was added to a solution of the intermediate 2 (10 g; 11.4 mmol) in dichloromethane (50 mL) at 0° C. The solution was then evaporated and the residue dissolved in trifluoroacetic acid (50 mL) and tris-isopropylsilane (0.2 mL). The mixture was stirred at room temperature for 24 h then was evaporated. The residue was dissolved in water (50 mL) and 2M aq. NaOH was added until pH=10. The solution was heated to 40° C. and stirred for 8 h, keeping the pH constant at 10. The solution was cooled and 2M aq. HCl was added until pH=1.

The crude product was then purified by chromatography on Amberlite XE 750 column (eluent: gradient water/MeCN), to give compound 3 (4.16 g). Yield: 57%.

1H-NMR, 13C-NMR, 31P-NMR and mass spectrum were consistent with the expected structure.

c) Complexation

A solution of gadolinium chloride hexahydrate (2.03 g; 5.5 mmol) in water (50 mL) was added to a solution of compound 3 (3.5 g; 5.5 mmol) in water (70 mL). The pH was raised to 8 with 2N NaOH and the stirred solution was heated to 50° C. then neutralized to pH 7 with 1N HCl and finally purified by chromatography on Amberchrome CG 161M column (eluent: water/MeCN=9:1) to give the gadolinium complex 4 (4.24 g). Yield: 92%. Mass spectrum and elemental analysis were consistent with the expected structure.

Example 11: Preparation of the Chelate Complex 12

The preparation of the starting compound was obtained by using the following synthetic Scheme 16.

Scheme 16

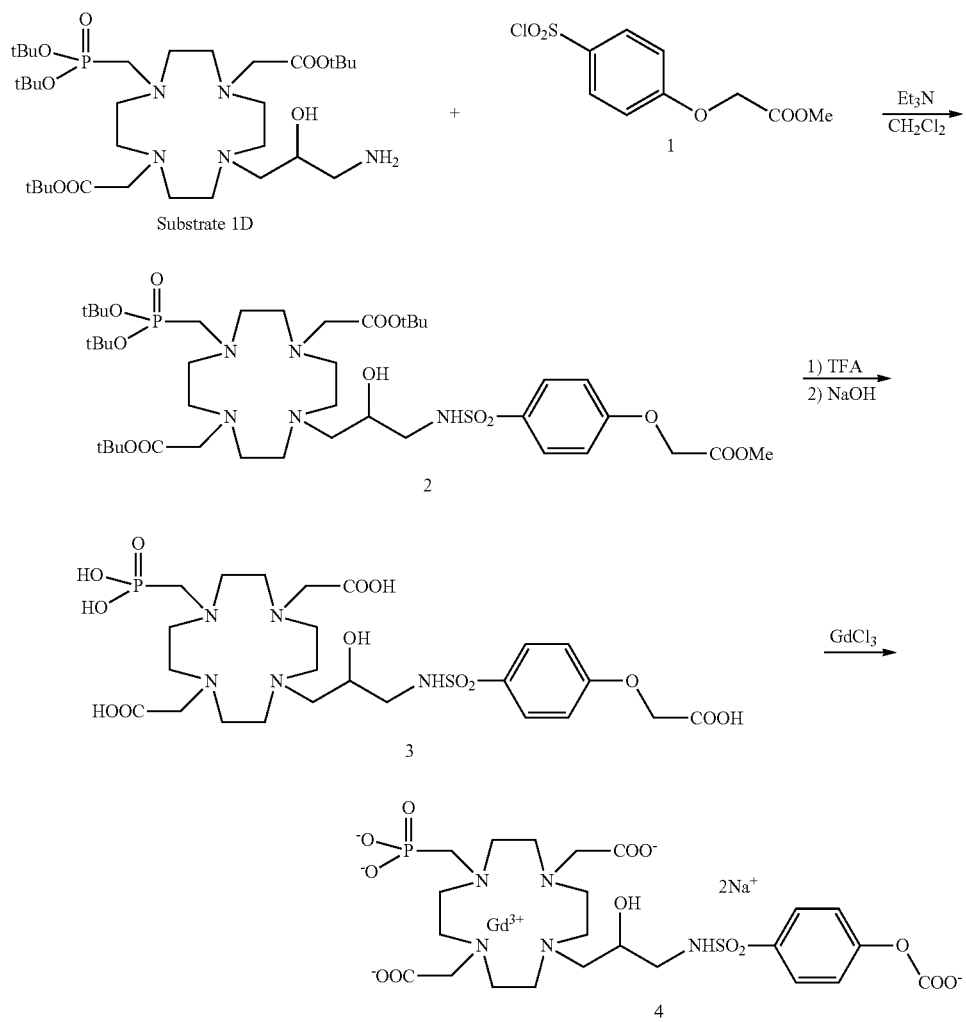

a) Preparation of Compound 2

A solution of methyl 2-[4-(chlorosulphonyl)phenoxy]acetate 1 (obtained as reported in *Molecules* 2009, 14, 5247-5280) (2.63 g; 9.8 mmol) in $CH_2Cl_2$ (20 mL) was slowly added drop by drop to a solution of Substrate 1D (obtained as described in Example 4) (4.5 g; 6.6 mmol) and triethylamine (3 mL) in $CH_2Cl_2$ (20 mL) at 0° C. At the end of the addition the temperature was raised to 20° C. and the mixture was stirred for 48 h. The solution was evaporated to a residue which was dissolved in EtOAc (80 mL), washed with water (4×50 mL) and brine (4×50 mL) then the organic phase was dried ($Na_2SO_4$) and evaporated to residue. The crude was purified by flash chromatography on silica gel (eluent: gradient of $CH_2Cl_2$/MeOH) to give compound 2 (5.6 g). Yield: 94%.

1H-NMR, 13C-NMR, 31P-NMR and mass spectrum were consistent with the expected structure.

b) Deprotection

Trifluoroacetic acid (5 mL) was added to a solution of compound 2 (5 g; 5.5 mmol) in dichloromethane (20 mL) at 0° C. The solution was then evaporated and the residue dissolved in trifluoroacetic acid (20 mL) and tris-isopropylsilane (0.1 mL). The mixture was stirred at room temperature for 24 h then was evaporated. The residue was suspended in water (50 mL) and 2M aq. NaOH was added until pH=12. The solution was stirred for 16 h. The solution was cooled and 2M aq. HCl was added until pH=1. The crude product was then purified by chromatography on Amberlite XE 750 column (eluent: gradient water/MeCN), to give compound 3 (1.48 g).Yield: 39%.

1H-NMR, 13C-NMR, 31P-NMR and mass spectrum were consistent with the expected structure.

c) Complexation

A solution of gadolinium chloride hexahydrate (2.23 g; 6 mmol) in water (50 mL) was added to a solution of compound 3 (4.1 g; 6 mmol) in water (100 mL). The pH was raised to 8 with 2N NaOH and the stirred solution was heated to 50° C. then neutralized to pH 7 with 1N HCl and finally purified by chromatography on Amberchrome CG 161M column (eluent: water/MeCN =9:1) to give the gadolinium complex 4 (4.63 g). Yield: 89%. Mass spectrum and elemental analysis were consistent with the expected structure.

Example 12: Preparation of the Chelate Complex 13

The preparation of the starting compound was obtained by using the following synthetic Scheme 17.

Scheme 17

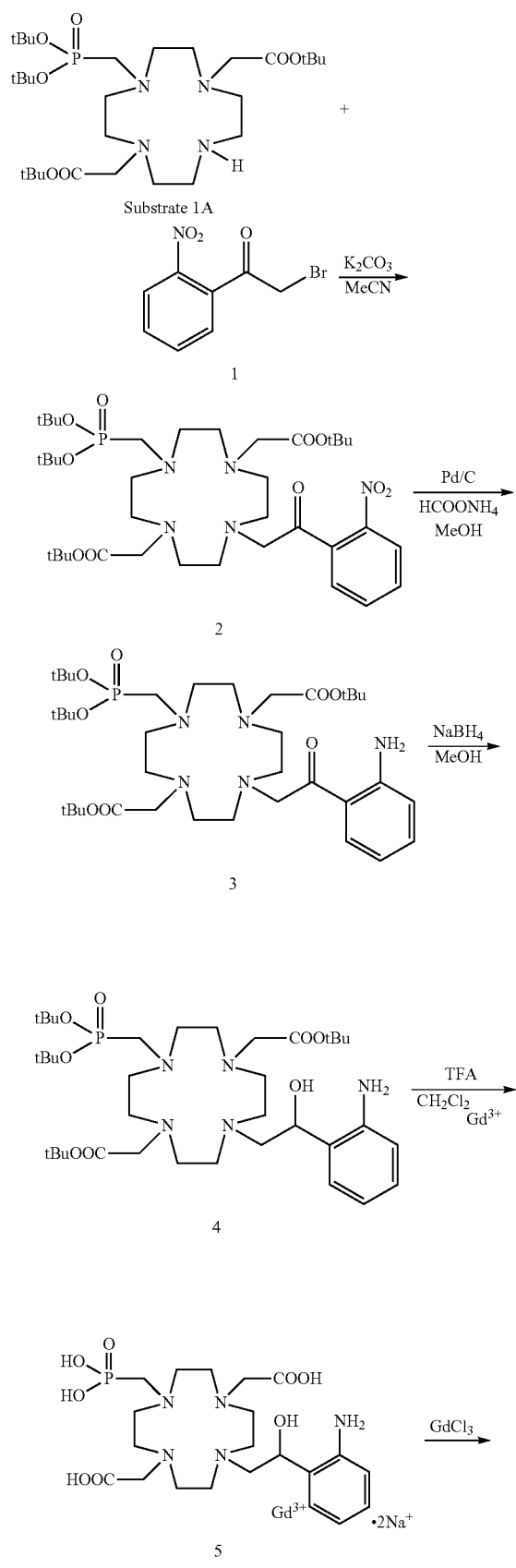

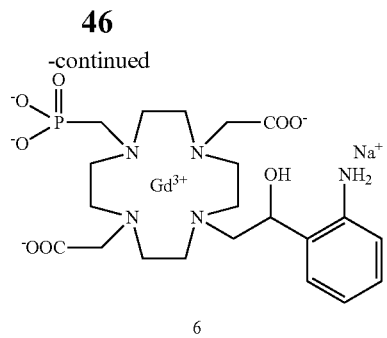

a) Preparation of Compound 2

A solution of 2-bromo-1-(2-nitrophenyl)ethanone (obtained as reported in *ARKIVOC* 2014, (iii), 256-273) (21 g; 86 mmol) in acetonitrile (100 mL) was added to a mixture of Substrate 1A (obtained as reported in Example 1) (52.2 g; 86 mmol) and $K_2CO_3$ (13.8 g; 100 mmol) in acetonitrile (200 mL). The mixture was stirred at room temperature for 24 h. The mixture was filtered and evaporated to a residue which was dissolved in $CH_2Cl_2$ (200 mL), washed with brine (2×200 mL), dried ($Na_2SO_4$) and evaporated to residue. The crude was purified by flash chromatography on silica gel (eluent: gradient of $CH_2Cl_2$/MeOH) to give compound 2 (36.4 g). Yield: 55%.

1H-NMR, 13C-NMR, 31P-NMR and mass spectrum were consistent with the expected structure.

b) Preparation of Compound 3

Palladium 5% on carbon (5 g) was added to a solution of compound 2 (30.8 g; 40 mmol) and ammonium formate (37.8 g; 600 mmol) in MeOH (300 mL). The mixture was stirred at room temperature for 16 h then filtered and evaporated. The residue was taken up with $CH_2Cl_2$ (400 mL) and brine (300 mL). The organic phase was separated, washed with brine (3×150 mL), dried ($Na_2SO_4$) and evaporated to residue. The crude was purified by flash chromatography on silica gel (eluent: gradient of $CH_2Cl_2$/MeOH) to give compound 3 (20.7 g). Yield: 70%.

1H-NMR, 13C-NMR, 31P-NMR and mass spectrum were consistent with the expected structure.

c) Preparation of Compound 4

Sodium borohydride (16.7 g; 441 mmol) was added in portions to a solution of compound 3 (14.8 g; 20 mmol) in dried MeOH (100 mL) kept at 0° C. The solution was stirred at room temperature for 6 h then was evaporated and the residue was taken up in $CH_2Cl_2$ (300 mL) and a saturated aqueous solution of $NH_4Cl$ (400 mL). The organic phase was separated, washed with aq. $NH_4Cl$ (2×200 mL), brine (2×200 mL), dried ($Na_2SO_4$) and evaporated to residue. The crude was purified by flash chromatography on silica gel (eluent: gradient of $CH_2Cl_2$/MeOH) to give compound 4 (9.94 g). Yield: 67%.

1H-NMR, 13C-NMR, 31P-NMR and mass spectrum were consistent with the expected structure.

d) Deprotection

Trifluoroacetic acid (10 mL) was added to a solution of compound 4 (9 g; 12 mmol) in dichloromethane (40 mL) at 0° C. The solution was then evaporated and the residue dissolved in trifluoroacetic acid (40 mL) and tris-isopropylsilane (0.2 mL). The mixture was stirred at room temperature for 24 h then was evaporated. The crude product was purified by chromatography on Amberlite XE 750 column (eluent: gradient water/MeCN), to give compound 5 (4.4 g).Yield: 71%.

1H-NMR, 13C-NMR, 31P-NMR and mass spectrum were consistent with the expected structure.

e) Complexation

A solution of gadolinium chloride hexahydrate (2.86 g; 7.7 mmol) in water (50 mL) was added to a solution of compound 5 (4.0 g; 7.7 mmol) in water (100 mL). The pH was raised to 8 with 2N NaOH and the stirred solution was heated to 50° C. then neutralized to pH 7 with 1N HCl and finally purified by chromatography on Amberchrome CG 161M column (eluent: water/MeCN =9:1) to give the gadolinium complex 6 (4.8 g). Yield: 90%. Mass spectrum and elemental analysis were consistent with the expected structure.

Example 13: Preparation of the Chelate Complex 14

The preparation of the starting compound was obtained by using the following synthetic Scheme 18.

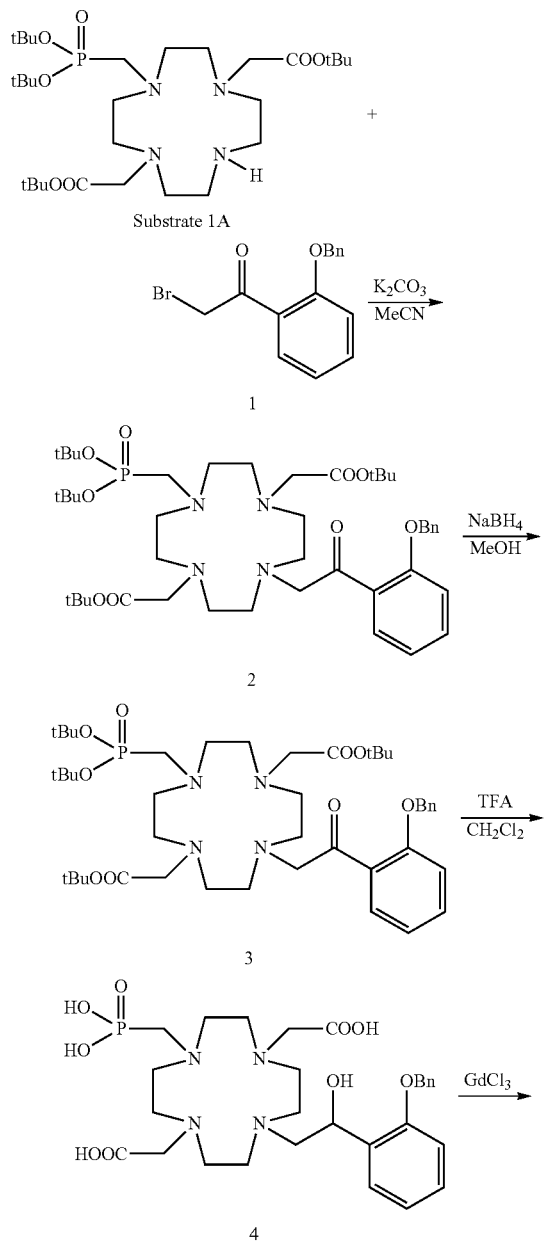

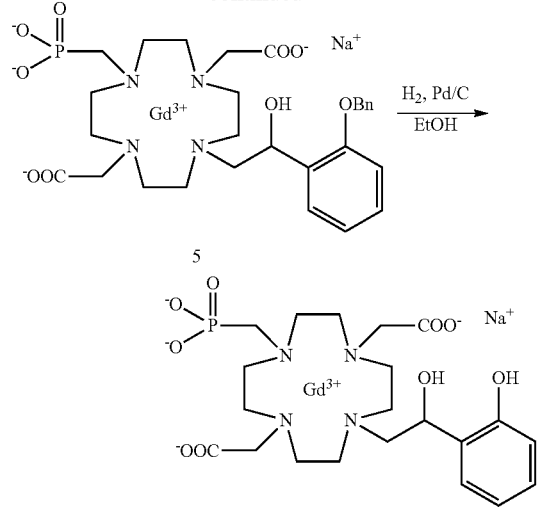

a) Preparation of Compound 2

A solution of 1-[2-(benzyloxy)phenyl]-2-bromoethanone (obtained as reported in *Bioorg. Med. Chem. Lett.* 2004, 14, 4013-4017) (13.6 g; 45 mmol) in acetonitrile (50 mL) was added to a mixture of Substrate 1A (obtained as reported in Example 1) (23.7 g; 39 mmol) and $K_2CO_3$ (8 g; 58 mmol) in acetonitrile (200 mL). The mixture was stirred at room temperature for 24 h. The mixture was filtered and evaporated to a residue which was dissolved in $CH_2Cl_2$ (200 mL), washed with brine (4×200 mL), dried ($Na_2SO_4$) and evaporated to residue. The crude was purified by flash chromatography on silica gel (eluent: gradient of $CH_2Cl_2$/MeOH) to give compound 2 (32.4 g). Yield: 89%.

1H-NMR, 13C-NMR, 31P-NMR and mass spectrum were consistent with the expected structure.

b) Preparation of Compound 3

Sodium borohydride (6.8 g; 180 mmol) was added in portions to a solution of compound 2 (30 g; 36 mmol) in dried MeOH (300 mL) kept at 0° C. The solution was stirred at room temperature for 6 h then was evaporated and the residue was taken up in $CH_2Cl_2$ (300 mL) and the organic phase was washed with saturated aq. $NH_4Cl$ (2×250 mL), brine (2×250 mL), dried ($Na_2SO_4$) and evaporated to residue. The crude was purified by flash chromatography on silica gel (eluent: gradient of $CH_2Cl_2$/MeOH) to give compound 3 (17.7 g). Yield: 59%.

1H-NMR, 13C-NMR, 31P-NMR and mass spectrum were consistent with the expected structure.

c) Deprotection

Trifluoroacetic acid (20 mL) was added to a solution of compound 3 (15 g; 18 mmol) in dichloromethane (100 mL) at 0° C. After 4 h the solution was evaporated and the residue dissolved in trifluoroacetic acid (100 mL) and tris-isopropylsilane (0.2 mL). The mixture was stirred at room temperature for 24 h then was evaporated. The crude product was purified by chromatography on Amberlite XE 750 column (eluent: gradient water/MeCN), to give compound 4 (8.1 g).Yield: 74%.

1H-NMR, 13C-NMR, 31P-NMR and mass spectrum were consistent with the expected structure.

d) Complexation

A solution of gadolinium chloride hexahydrate (4.27 g; 11.5 mmol) in water (75 mL) was added to a solution of compound 4 (7 g; 11.5 mmol) in water (150 mL). The pH was raised to 8 with 2N NaOH and the stirred solution was heated to 50° C. then neutralized to pH 7 with 1N HCl and finally purified by chromatography on Amberchrome CG 161M column (eluent: water/MeCN =9:1) to give the gadolinium complex 5 (8.3 g). Yield: 92%. Mass spectrum and elemental analysis were consistent with the expected structure.

e) Hydrogenation

Palladium 5% on carbon (2 g) was added to a solution of gadolinium complex 5 (7.5 g; 9.6 mmol) in water (150 mL) and EtOH (150 mL). The hydrogenation reaction was carried out for 6 h (room temperature, 1 atm), then the catalyst was filtered and washed with water. The organic solution was concentrated to remove the organic solvent, filtered on Millipore HA 0.45 m and lyophilized to give the complex compound 6 as a solid (6.27 g). Yield 94%.

Mass spectrum and elemental analysis were consistent with the expected structure.

Example 14: Preparation of the Chelate Complex 15

The preparation of the starting compound was obtained by using the following synthetic Scheme 19.

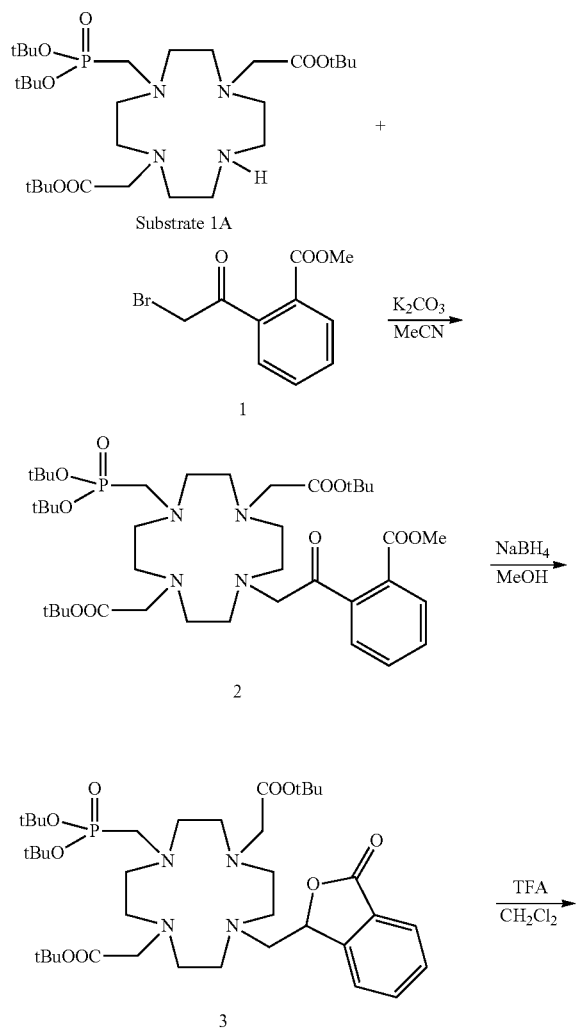

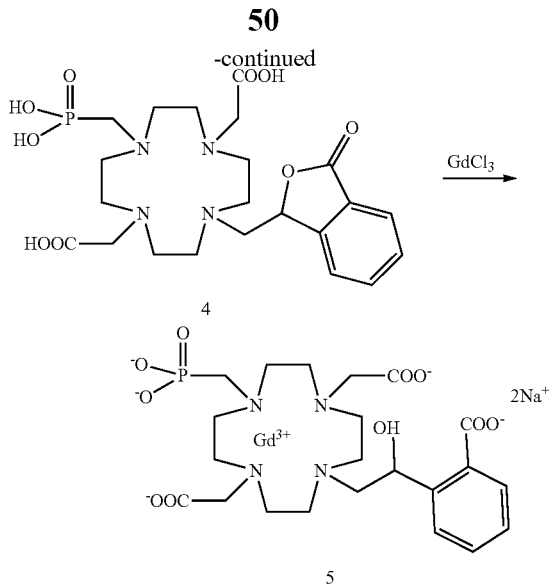

a) Preparation of Compound 2

A solution of 2-bromoacetyl-benzoic acid methyl ester (obtained as reported in *Molecules* 2006, 11, 574-582) (21 g; 82 mmol) in acetonitrile (100 mL) was added to a mixture of Substrate 1A (obtained as reported in Example 1) (50 g; 82 mmol) and $K_2CO_3$ (13.8 g; 100 mmol) in acetonitrile (200 mL). The mixture was stirred at room temperature for 24 h. The mixture was filtered and evaporated to a residue which was dissolved in $CH_2Cl_2$ (200 mL), washed with brine (4×200 mL), dried ($Na_2SO_4$) and evaporated to residue. The crude was purified by flash chromatography on silica gel (eluent: gradient of $CH_2Cl_2$/MeOH) to give compound 2 (55.9 g). Yield: 87%.

1H-NMR, 13C-NMR, 31P-NMR and mass spectrum were consistent with the expected structure.

b) Preparation of Compound 3

Sodium borohydride (12.1 g; 320 mmol) was added in portions to a solution of compound 2 (50 g; 64 mmol) in dried MeOH (400 mL) kept at 0° C. The solution was stirred at room temperature for 8 h then was evaporated and the residue was taken up in $CH_2Cl_2$ (400 mL) and the organic phase was washed with saturated aq. $NH_4Cl$ (2×250 mL), brine (2×250 mL), dried ($Na_2SO_4$) and evaporated to residue. The crude was purified by flash chromatography on silica gel (eluent: gradient of $CH_2Cl_2$/MeOH) to give compound 3 (31.3 g). Yield: 65%.

1H-NMR, 13C-NMR, 31P-NMR and mass spectrum were consistent with the expected structure.

c) Deprotection

Trifluoroacetic acid (50 mL) was added to a solution of compound 3 (30 g; 40 mmol) in dichloromethane (200 mL) at 0° C. After 6 h the solution was evaporated and the residue dissolved in trifluoroacetic acid (150 mL) and tris-isopropylsilane (0.2 mL). The mixture was stirred at room temperature for 24 h then was evaporated. The crude product was purified by chromatography on Amberlite XAD 1600 column (eluent: gradient water/MeCN), to give compound 4 (16.7 g).Yield: 79%.

1H-NMR, 13C-NMR, 31P-NMR and mass spectrum were consistent with the expected structure.

d) Complexation

2M NaOH was added to a solution of compound 4 (15 g; 28.4 mmol) in water (250 mL) until pH 12 and the mixture was stirred for 24 h. A solution of gadolinium chloride hexahydrate (10.55 g; 28.4 mmol) in water (75 mL) was added and the pH was adjusted to 8 with 2N NaOH. The solution was heated to 50° C. and stirred for 8 h then neutralized to pH 7 with 1N HCl and finally purified by chromatography on Amberchrome CG 161M column (eluent: water/MeCN =9:1) to give the gadolinium complex 5 (18.6 g). Yield: 88%.

Mass spectrum and elemental analysis were consistent with the expected structure.

Example 15: Preparation of the Chelate Complex 16

The preparation of the starting compound was obtained by using the following synthetic Scheme 20.

a) Preparation of Compound 3

A solution of benzene-1,3-disulfonyl chloride (commercially available) (8.25 g; 30 mmol) in dichloromethane (50 mL) was slowly added to a solution of Substrate 1D (obtained as described in Example 4) (40.8 g; 60 mmol) and diisopropylethylamine (12 mL) in $CH_2Cl_2$ (300 mL) at room temperature. The mixture was stirred for 24 h then washed wth water (2×200 mL), brine (2×200 mL), dried ($Na_2SO_4$) and evaporated. The crude was purified by flash chromatography on silica gel (eluent: gradient of $CH_2Cl_2/MeOH$) to give compound 3 (32.8 g). Yield: 70%.

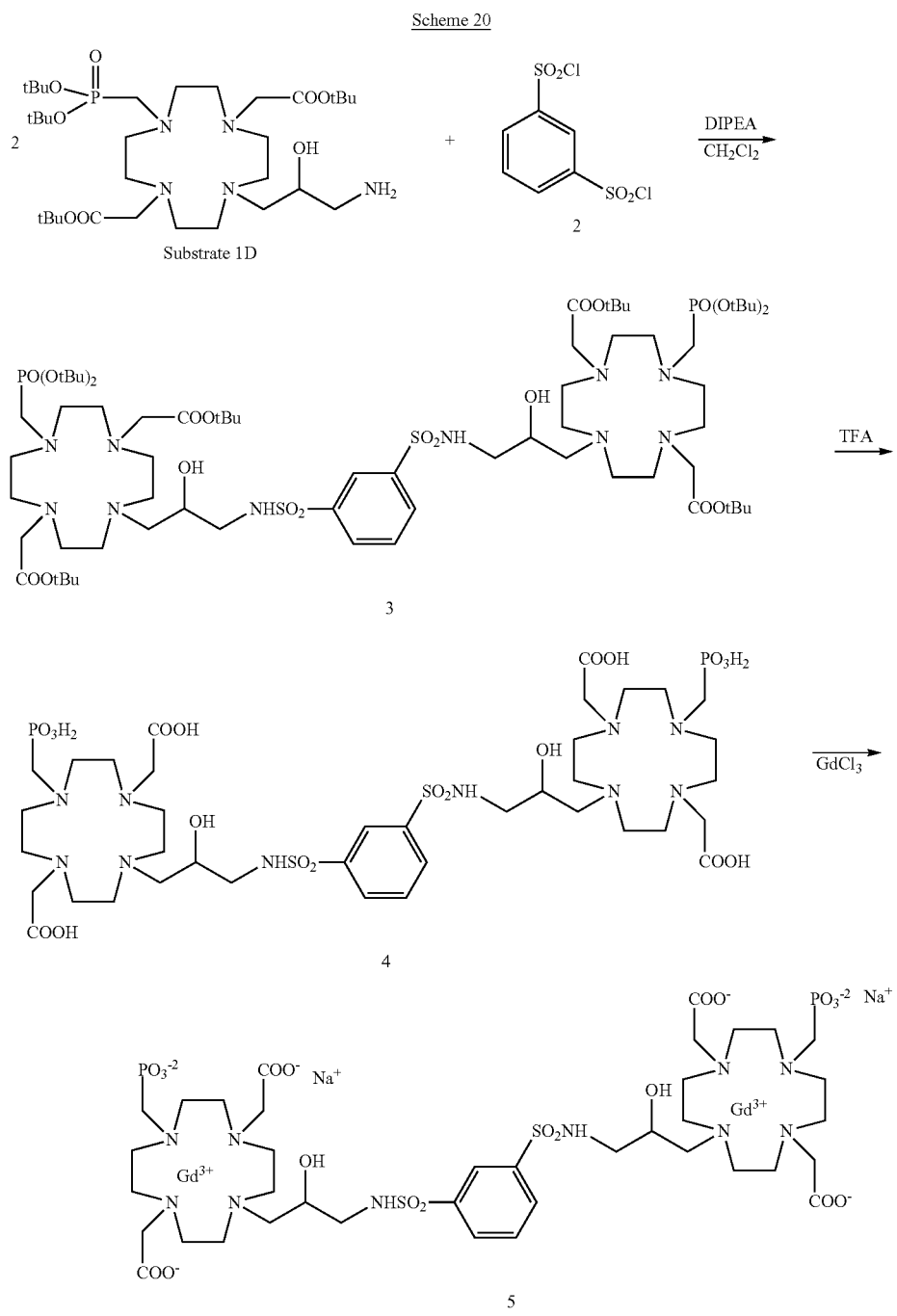

Scheme 20

1H-NMR, 13C-NMR, 31P-NMR and mass spectrum were consistent with the expected structure.

b) Deprotection

Trifluoroacetic acid (100 mL) was added to a solution of compound 3 (30 g; 19 mmol) in dichloromethane (300 mL) at 0° C. After 8 h the solution was evaporated and the residue dissolved in trifluoroacetic acid (200 mL) and tris-isopropylsilane (0.4 mL). The mixture was stirred at room temperature for 24 h then was evaporated. The crude product was purified by chromatography on Amberlite XE 750 column (eluent: gradient water/MeCN), to give compound 4 (14.6 g).Yield: 69%.

1H-NMR, 13C-NMR, 31P-NMR and mass spectrum were consistent with the expected structure.

c) Complexation

A solution of gadolinium chloride hexahydrate (8.03 g; 21.6 mmol) in water (100 mL) was added to a solution of compound 4 (12 g; 10.8 mmol) in water (250 mL). The pH was raised to 8 with 2N NaOH and the stirred solution was heated to 50° C. then neutralized to pH 7 with 1N HCl and finally purified by chromatography on Amberlite XE 750 column (eluent: gradient water/MeCN) to give the gadolinium complex 5 (13.4 g). Yield: 85%. Mass spectrum and elemental analysis were consistent with the expected structure.

Example 16: Preparation of the Chelate Complex 18

The preparation of the starting compound was obtained by using the following synthetic Scheme 21.

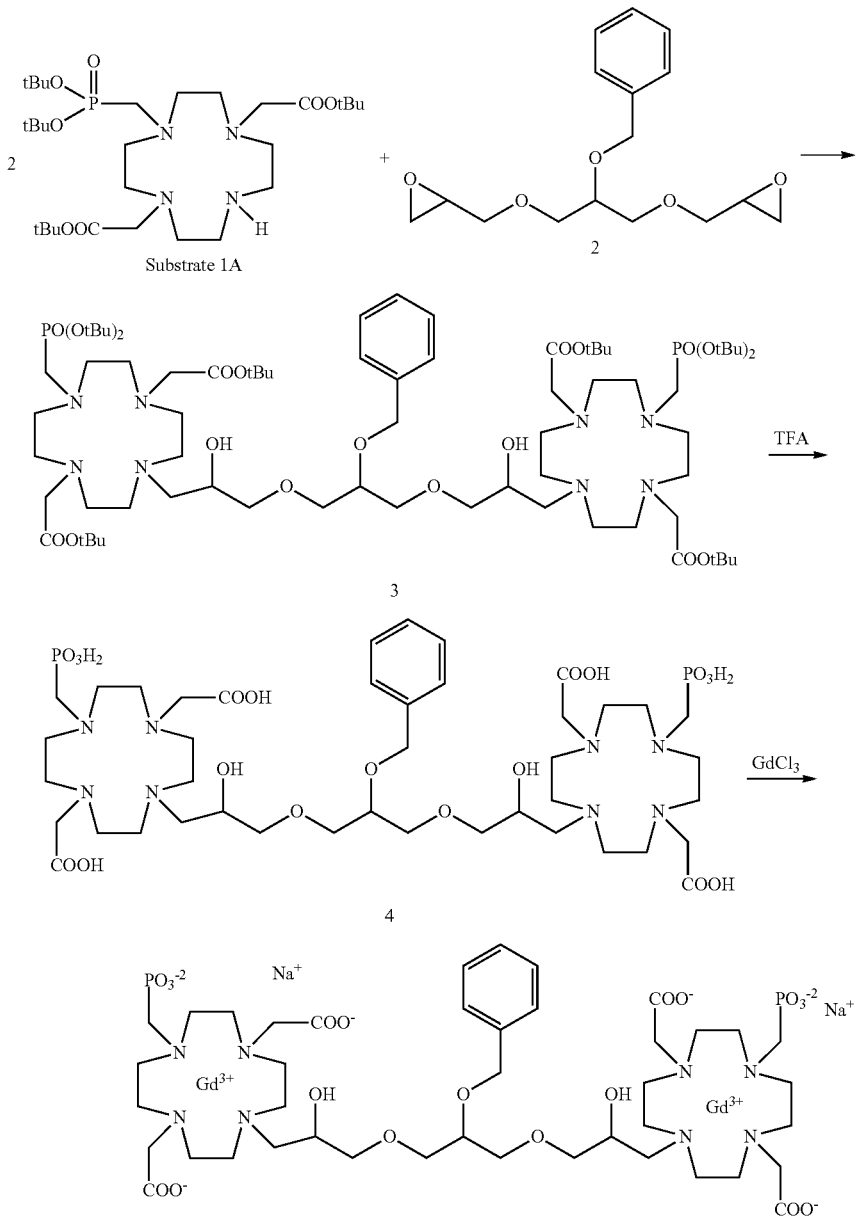

Scheme 21 a) Preparation of Compound 3

A solution of Substrate 1A (24.7 g; 40.7 mmol) and compound 2 (obtained as reported in *Eur. J. Org. Chem.* 2001, 875-896) (6 g; 20.3 mmol) in dichloromethane (300 mL) was stirred at room temperature for 48 h. The mixture was evaporated and the residue purified by flash chromatography on silica gel (eluent: gradient of $CH_2Cl_2$/MeOH) to give compound 3 (18 g). Yield: 59%.

1H-NMR, 13C-NMR, 31P-NMR and mass spectrum were consistent with the expected structure.

b) Deprotection

Trifluoroacetic acid (40 mL) was added to a solution of compound 3 (15.1 g; 10 mmol) in dichloromethane (150 mL) at 0° C. After 8 h the solution was evaporated and the residue dissolved in trifluoroacetic acid (100 mL) and tris-isopropylsilane (0.2 mL). The mixture was stirred at room temperature for 24 h then was evaporated. The crude product was purified by chromatography on Amberlite XE 750 column (eluent: gradient water/MeCN), to give compound 4 (6.6 g).Yield: 62%.

1H-NMR, 13C-NMR, 31P-NMR and mass spectrum were consistent with the expected structure.

c) Complexation

A solution of gadolinium chloride hexahydrate (4.09 g; 11 mmol) in water (50 mL) was added to a solution of compound 4 (5.8 g; 5.5 mmol) in water (100 mL). The pH was raised to 8 with 2N NaOH and the stirred solution was heated to 50° C. then neutralized to pH 7 with 1N HCl and finally purified by chromatography on Amberlite XE 750 column column (eluent: gradient water/MeCN) to give the gadolinium complex 5 (6.6 g). Yield: 85%.

Mass spectrum and elemental analysis were consistent with the expected structure.

Example 17: Preparation of the Chelate Complex 19

The preparation of the starting compound was obtained by using the following synthetic Scheme 22.

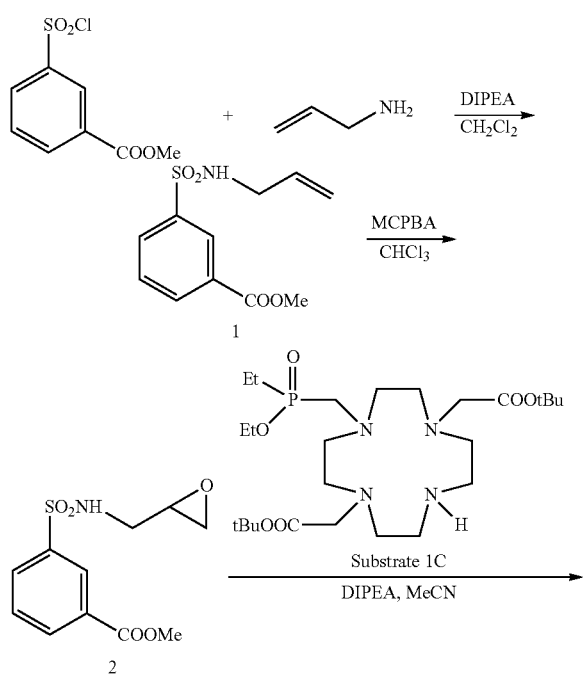

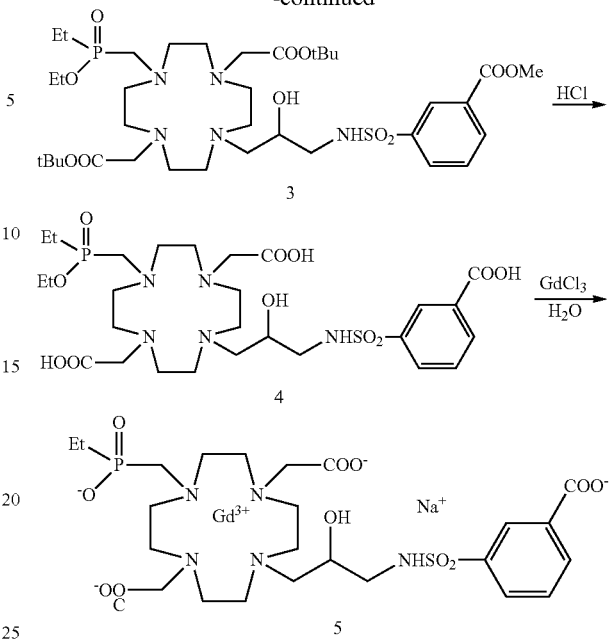

a) Preparation of Compound 1

A solution of methyl 3-(chlorosulphonyl)benzoate (obtained as reported in *J. Med. Chem.* 2007, 50, 442-454) (35.2 g; 0.15 mol) in dichloromethane (100 mL) was slowly added to a stirred solution of allylamine (9.1 g; 0.16 mol) and DIPEA (23.3 g; 0.18 mol) in dichloromethane (250 mL). The solution was stirred at 20° C. for 8 h then washed with water (2×100 mL), 1N HCl until acidic pH, water (2×100 mL) and brine (2×100 mL). The solution was evaporated to give compound 1 (36.4 g). Yield: 95%.

1H-NMR, 13C-NMR, and mass spectrum were consistent with the expected structure.

b) Preparation of Compound 2

A solution of 3-chloroperbenzoic acid (29.5 g; 0.120 mol) in chloroform (150 mL) was added dropwise to a solution of compound 1 (25.5 g; 0.10 mol) in chloroform (150 mL) and the mixture was stirred for 24 h. Then the solution was washed with 5% aq. $NaHCO_3$ until basic pH, with water (2×100 mL), with brine (2×100 mL), dried ($Na_2SO_4$) and evaporated. The crude product was purified by chromatography on silica gel (eluent: gradient n-heptane/EtOAc) to give compound 2 (24.7 g). Yield: 91%.

1H-NMR, 13C-NMR, and mass spectrum were consistent with the expected structure.

c) Preparation of Compound 3

A mixture of Substrate 1C, obtained as described in Example 3, (20 g; 37.4 mmol), compound 2 (11.1 g; 40.9 mmol) and N,N-diisopropylethylamine (DIPEA) (20 mL) in MeCN (200 mL) was stirred at 60° C. for 72 h. The solution was concentrated to a residue which was dissolved in EtOAc (250 mL). The solution was washed with water (2×100 mL), brine (2×100 mL) and evaporated to a residue which was purified by flash-chromatography on silica gel (eluent: gradient $CH_2Cl_2$/MeOH) to give compound 3 (21.8 g). Yield: 70%.

1H-NMR, 13C-NMR, 31P-NMR and mass spectrum were consistent with the expected structure.

d) Deprotection

A mixture of compound 3 (20 g; 24 mmol) in 6 M HCl (250 mL) was heated to reflux for 16 h. The solution was evaporated and the residue was purified by chromatography on Amberchrome CG 161M column (eluent: gradient water/MeCN) to give compound 4 (13 g). Yield: 80%.

1H-NMR, 13C-NMR, 31P-NMR and mass spectrum were consistent with the expected structure.

e) Complexation

A solution of gadolinium chloride hexahydrate (5.46 g; 14.7 mmol) in water (80 mL) was added to a solution of compound 4 (10 g; 14.7 mmol) in water (200 mL). The pH was raised to 8 with 2N NaOH and the stirred solution was heated to 50° C. then neutralized to pH 7 with 1N HCl and finally purified by chromatography on Amberchrome CG 161M column (eluent: gradient water/MeCN) to give the gadolinium complex 5 (10.7 g). Yield: 88%. Mass spectrum and elemental analysis were consistent with the expected structure.

Example 18: Preparation of the Chelate Complex 20

The preparation of the starting compound was obtained by using the following synthetic Scheme 23.

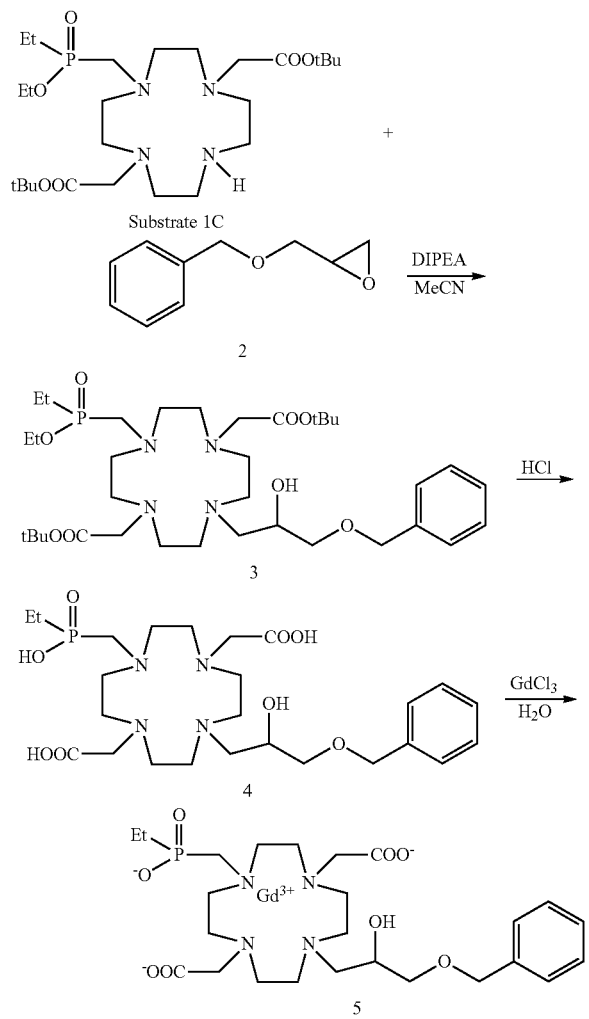

a) Preparation of Compound 3

A mixture of Substrate 1C, obtained as described in Example 3, (20 g; 37.4 mmol), benzyl glycidyl ether 2 (commercially available) (6.9 g; 42 mmol) and N,N-diisopropylethylamine (DIPEA) (20 mL) in MeCN (200 mL) was stirred at 60° C. for 72 h. The solution was concentrated to a residue which was dissolved in EtOAc (250 mL). The solution was washed with water (2×100 mL), brine (2×100 mL) and evaporated to a residue which was purified by flash-chromatography on silica gel (eluent: gradient $CH_2Cl_2$/MeOH) to give compound 3 (20.4 g). Yield: 78%.

1H-NMR, 13C-NMR, 31P-NMR and mass spectrum were consistent with the expected structure.

b) Deprotection

A mixture of compound 3 (18 g; 25.8 mmol) in 6 M HCl (250 mL) was heated to reflux for 16 h. The solution was evaporated and the residue was purified by chromatography on Amberlite XAD 1600 column (eluent: gradient water/MeCN) to give compound 4 (11.8 g). Yield: 82%.

1H-NMR, 13C-NMR, 31P-NMR and mass spectrum were consistent with the expected structure.

c) Complexation

A solution of gadolinium chloride hexahydrate (5.57 g; 15 mmol) in water (50 mL) was added to a solution of compound 4 (8.4 g; 15 mmol) in water (200 mL). The pH was raised to 8 with 2N NaOH and the stirred solution was heated to 50° C. then neutralized to pH 7 with 1N HCl and finally purified by chromatography on Amberlite XAD 1600 column (eluent: gradient water/MeCN) to give the gadolinium complex 5 (10.3 g). Yield: 96%.

Mass spectrum and elemental analysis were consistent with the expected structure.

Example 19: Preparation of the Chelate Complex 21

The preparation was carried out by following the synthetic procedure of Scheme 24

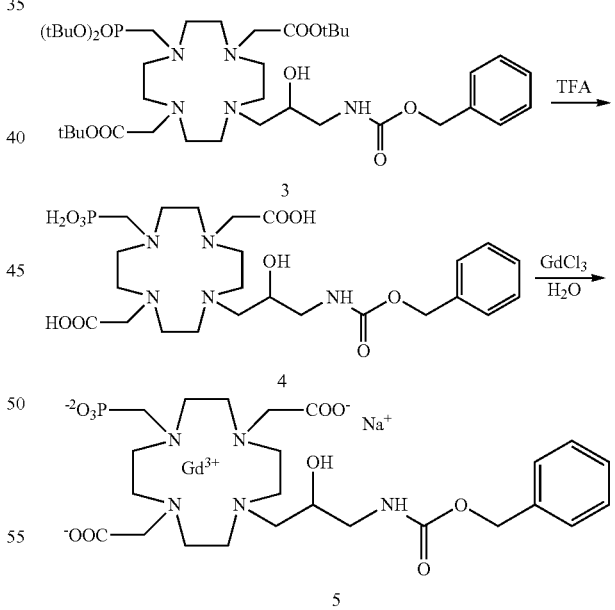

a) Deprotection

Trifluoroacetic acid (40 mL) was added to a solution of the intermediate 3, obtained as described in Example 4, (40.5 g; 0.05 mol) in dichloromethane (150 mL) at 0° C. The solution was then evaporated and the residue dissolved in trifluoroacetic acid (180 mL) and tris-isopropylsilane (0.2 mL). The mixture was stirred at room temperature for 24 h then was diluted with ethyl ether (900 mL) to give a solid that was filtered, washed with ethyl ether and dried. The crude product was then purified by chromatography on Amberchrome CG161M column (eluent: gradient water/MeCN), to give the desired compound 4 (15.6 g).Yield: 53%.
HPLC purity: 99%.
1H-NMR, 13C-NMR, 31P-NMR and mass spectrum were consistent with the expected structure.
b) Complexation
A solution of gadolinium chloride hexahydrate (1.97 g; 5.3 mmol) in water (50 mL) was added to a solution of compound 4 (3.3 g; 5.3 mmol) in water (50 mL). The pH was raised to 8 with 2N NaOH and the stirred solution was heated to 50° C. then neutralized to pH 7 with 1N HCl and finally purified by chromatography on Amberchrome CG 161M column (eluent: water/MeCN =9:1) to give the gadolinium complex 5 (3.86 g). Yield: 95%. HPLC purity: 100%. Mass spectrum and elemental analysis were consistent with the expected structure.

Example 20: Preparation of the Chelate Complex 22

The preparation was carried out by following the synthetic procedure of Scheme 25 a) Preparation of Compound 3
2-Benzyloxyethyl chloroformate (commercially available) (7 g; 33 mmol) was added to a solution of Substrate 1D (obtained as reported in Example 4) (20.4 g; 30 mmol) and triethylamine (3.5 g; 3.5 mmol) in dichlorometane (200 mL) and the mixture was stirred at room temperature for 16 h. The mixture was washed with water (3×100 mL), brine (3×100 mL) and evaporated to residue. The crude was purified by flash chromatography on silica gel (eluent: gradient of $CH_2Cl_2$/MeOH) to give compound 3 (23.7 g). Yield: 92%.
1H-NMR, 13C-NMR, 31P-NMR and mass spectrum were consistent with the expected structure.
b) Deprotection
Trifluoroacetic acid (30 mL) was added to a solution of the intermediate 3 (21.5 g; 25 mmol) in dichloromethane (100 mL) at 0° C. The solution was then evaporated and the residue dissolved in trifluoroacetic acid (100 mL) and tris-isopropylsilane (0.2 mL). The mixture was stirred at room temperature for 24 h then was evaporated. The crude product was then purified by chromatography on Amberchrome Scheme 25

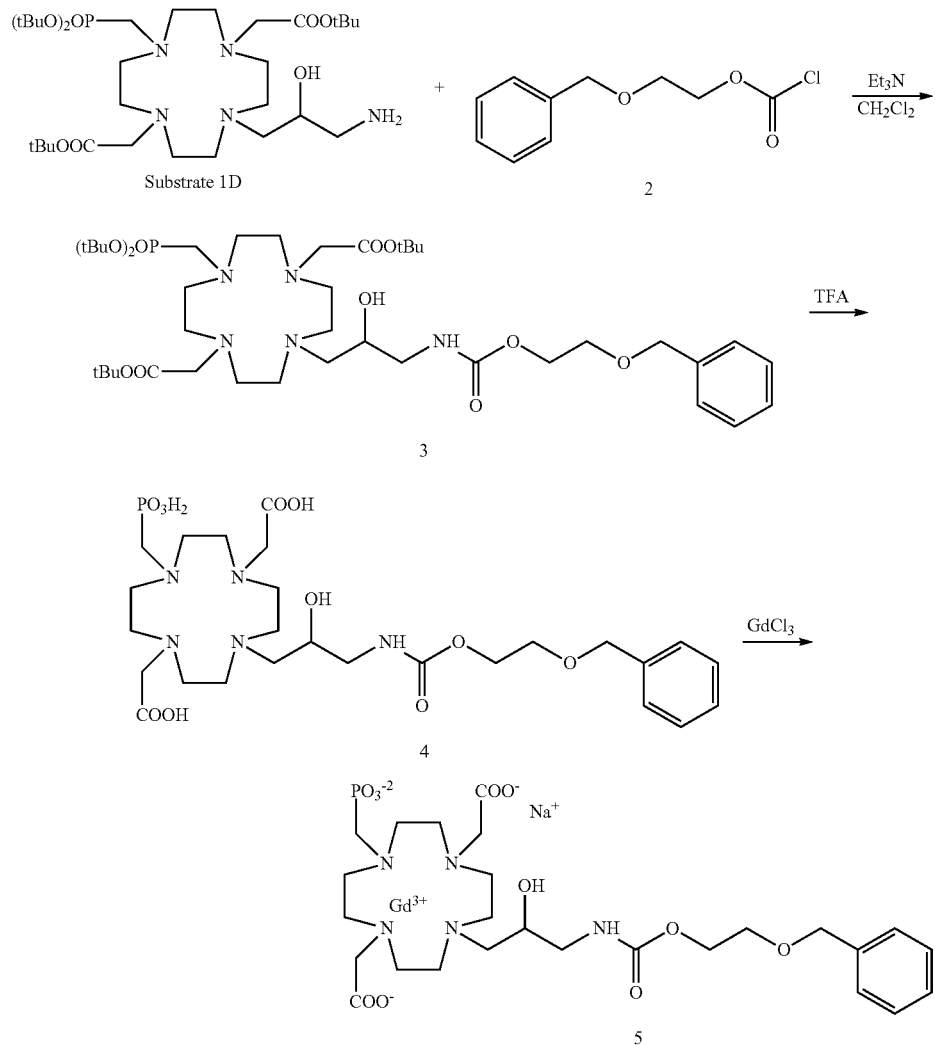

CG161M column (eluent: gradient water/MeCN), to give the desired compound 4 (10.6 g). Yield: 67%. HPLC purity: 98%.

1H-NMR, 13C-NMR, 31P-NMR and mass spectrum were consistent with the expected structure.

c) Complexation

A solution of gadolinium chloride hexahydrate (3.7 g; 10 mmol) in water (100 mL) was added to a solution of compound 4 (6.3 g; 10 mmol) in water (100 mL). The pH was raised to 8 with 2N NaOH and the stirred solution was heated to 50° C. then neutralized to pH 7 with 1N HCl and finally purified by chromatography on Amberchrome CG 161M column (eluent: water/MeCN =9:1) to give the gadolinium complex 5 (7.3 g). Yield: 90%.

HPLC purity: 99%.

Mass spectrum and elemental analysis were consistent with the expected structure.

The Chelate Complex 23 was analogously prepared following the same synthetic strategy and employing 2-methoxyethyl chloroformate (commercially available).

The Chelate Complex 24 was analogously prepared following the same synthetic strategy and employing cyclohexyl chloroformate (commercially available).

Example 21: Preparation of the Chelate Complex 25

The preparation was carried out by following the synthetic procedure of scheme 26

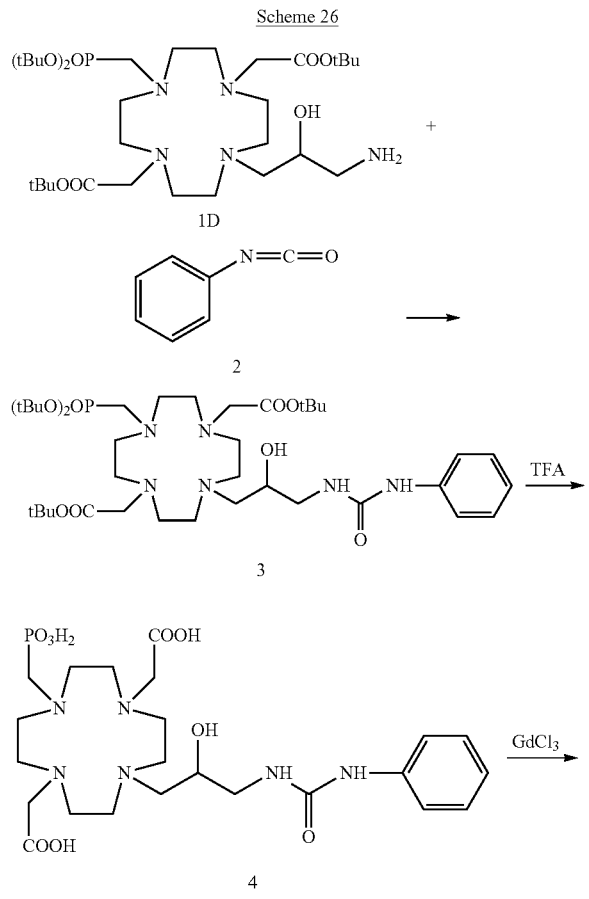

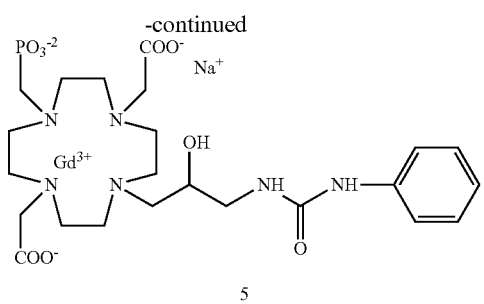

a) Preparation of Compound 3

A solution of phenyl isocyanate 2 (commercially available) (3.6 g; 30 mmol) in CH$_2$Cl$_2$ (25 mL) was slowly added to a solution of Substrate 1D (obtained as described in Example 4) (20.4 g; 30 mmol) in CH$_2$Cl$_2$ (200 mL) at 0° C. At the end of the addition the temperature was raised to 20° C. and the mixture was stirred for 24 h. The solution was washed with water (3×100 mL), brine (3×100 mL) then the organic phase was dried (Na$_2$SO$_4$) and evaporated to residue. The crude was purified by flash chromatography on silica gel (eluent: gradient of CH$_2$Cl$_2$/MeOH) to give compound 3 (21.3 g). Yield: 89%.

1H-NMR, 13C-NMR, 31P-NMR and mass spectrum were consistent with the expected structure.

b) Deprotection

Trifluoroacetic acid (15 mL) was added to a solution of the intermediate 3 (20 g; 25 mmol) in dichloromethane (100 mL) at 0° C. The solution was then evaporated and the residue dissolved in trifluoroacetic acid (100 mL) and tris-isopropylsilane (0.2 mL). The mixture was stirred at room temperature for 24 h then was evaporated. The residue was then purified by chromatography on Amberlite XE 750 column (eluent: gradient water/MeCN), to give compound 4 (9.6 g). Yield: 67%.

1H-NMR, 13C-NMR, 31P-NMR and mass spectrum were consistent with the expected structure.

c) Complexation

A solution of gadolinium chloride hexahydrate (5.5 g; 14.8 mmol) in water (50 mL) was added to a solution of compound 4 (8.5 g; 14.8 mmol) in water (150 mL). The pH was raised to 8 with 2N NaOH and the stirred solution was heated to 50° C. then neutralized to pH 7 with 1N HCl and finally purified by chromatography on Amberlite XE 750 column (eluent: gradient water/MeCN) to give the gadolinium complex 5 (9.44 g). Yield: 85%. Mass spectrum and elemental analysis were consistent with the expected structure.

Example 22: Preparation of the Chelate Complex 27

The preparation was carried out by following the synthetic procedure of scheme 27

Scheme 27

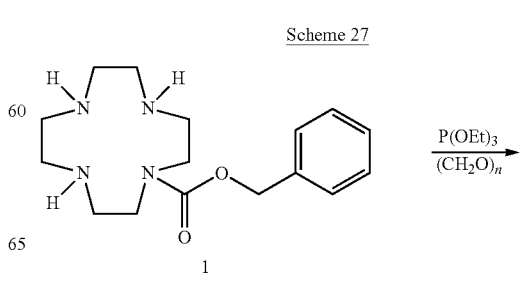

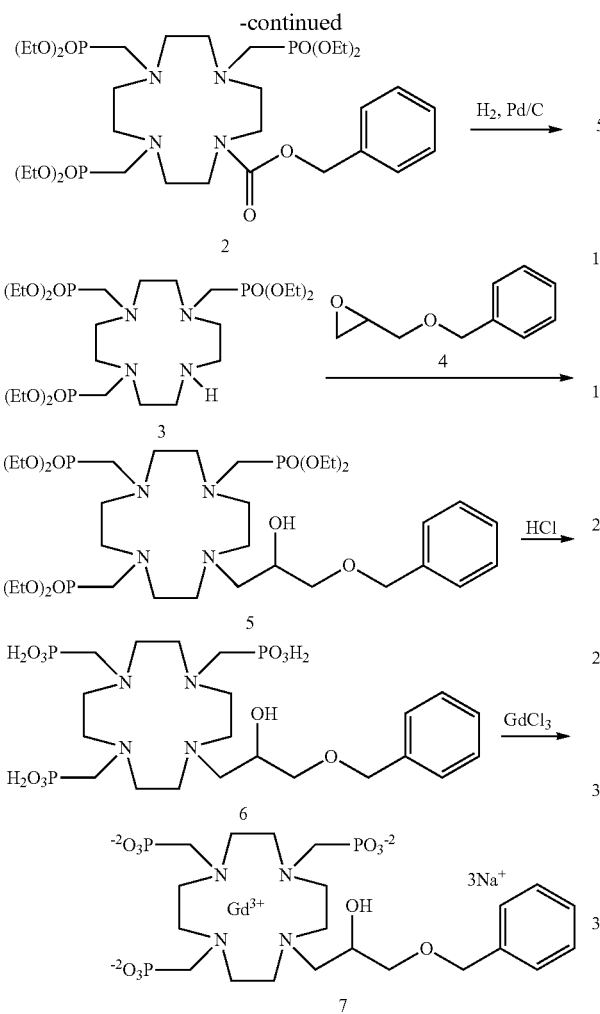

for 48 h, then evaporated. The residue was dissolved in EtOAc (200 mL) and the solution was washed with brine (3×100 ml), then evaporated. The crude was purified by flash-chromatography on silica gel (eluent: gradient $CH_2Cl_2$/MeOH) to give intermediate 5 (9.8 g). Yield: 83%.

1H-NMR, 13C-NMR and mass spectrum were consistent with the expected structure.

c) Deprotection

A mixture of compound 5 (8.7 g; 11 mmol) in 6 M HCl (200 mL) was stirred at room temperature for 16 h then heated to reflux for 36 h. The solution was evaporated and the residue was purified by chromatography on Amberlite XAD 1600 column (eluent: gradient water/MeCN) to give compound 5 (4.4 g). Yield: 65%.

1H-NMR, 13C-NMR, 31P-NMR and mass spectrum were consistent with the expected structure.

c) Complexation

A solution of gadolinium chloride hexahydrate (2.42 g; 6.5 mmol) in water (25 mL) was added to a solution of compound 5 (4 g; 6.5 mmol) in water (100 mL). The pH was raised to 8 with 2N NaOH and the stirred solution was heated to 50° C. then neutralized to pH 7 with 1N HCl and finally purified by chromatography on Amberlite XAD 1600 column (eluent: gradient water/MeCN) to give the gadolinium complex 6 (5 g). Yield: 93%.

Mass spectrum and elemental analysis were consistent with the expected structure.

Example 23: Preparation of the Chelate Complex 28

The preparation was carried out by following the synthetic procedure of scheme 28

Scheme 28

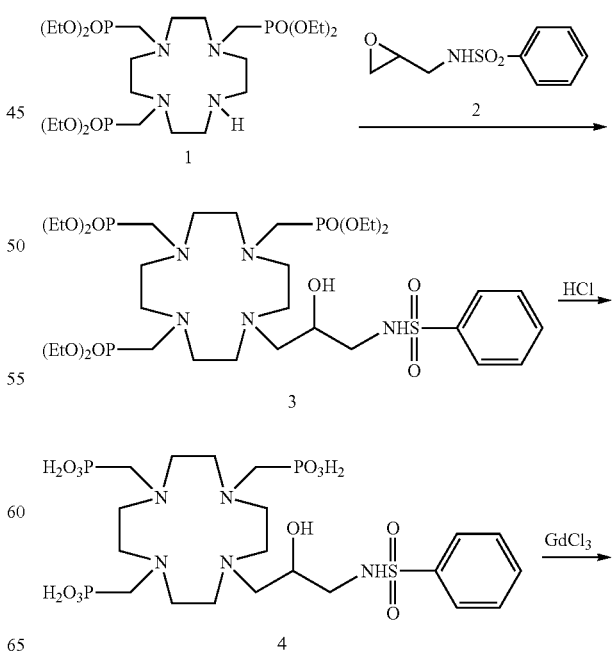

a) Preparation of Compound 2
A mixture of compound 1 (obtained as reported in Tetrahedron Lett. 2008, 49, 6308-6310) (12.3 g; 0.040 mol), triethyl phosphite (26.6 g; 0.160 mol) and paraformaldehyde (4.8 g; 0.160 mol) was stirred at room temperature for 96 h. The volatiles were evaporated under vacuum and the residue purified flash chromatography on silica gel (eluent: gradient of $CH_2Cl_2$/MeOH) to give compound 2 (19.4 g). Yield: 64%.

1H-NMR, 13C-NMR, 31P-NMR and mass spectrum were consistent with the expected structure.

b) Preparation of Compound 3
Palladium 5% on carbon (4 g) was added to a solution of compound 2 (15.1 g; 20 mmol) in EtOH (200 mL). The hydrogenation reaction was carried out for 8 h (room temperature, 1 atm), then the catalyst was filtered. The organic solution was filtered again on Millipore HA 0.45 μm then evaporated to give compound 3 (12.1 g). Yield 97%.

1H-NMR, 13C-NMR, 31P-NMR and mass spectrum were consistent with the expected structure.

c) Preparation of Compound 5
Commercially available benzyl glycidyl ether 4 (3 g; 18 mmol) was added to a solution of compound 3 (9.34 g; 15 mmol) in MeCN (150 mL). The mixture was heated at reflux -continued

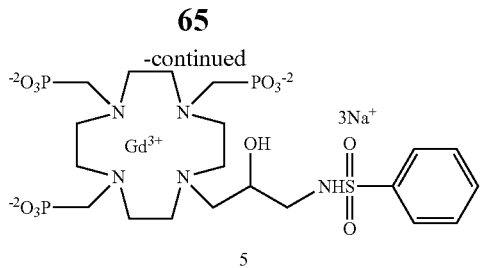

5 a) Preparation of Compound 3

A solution of compound 1 (obtained as reported in Example 24) (18.7 g; 30 mmol) and compound 2 (obtained as reported in Example 11) (7 g; 33 mmol) in MeCN (250 mL). The mixture was heated at reflux for 48 h, then evaporated. The residue was dissolved in EtOAc (200 mL) and the solution was washed with brine (3×100 ml), then evaporated. The crude was purified by flash-chromatography on silica gel (eluent: gradient $CH_2Cl_2$/MeOH) to give intermediate 3 (18.8 g). Yield: 75%.

1H-NMR, 13C-NMR, 31P-NMR and mass spectrum were consistent with the expected structure.

b) Deprotection

A mixture of compound 3 (16.7 g; 20 mmol) in 6 M HCl (300 mL) was stirred at room temperature for 16 h then heated to reflux for 36 h. The solution was evaporated and the residue was purified by chromatography on Amberlite XAD 1600 column (eluent: gradient water/MeCN) to give compound 4 (9 g). Yield: 67%.

1H-NMR, 13C-NMR, 31P-NMR and mass spectrum were consistent with the expected structure.

c) Complexation

A solution of gadolinium chloride hexahydrate (4.46 g; 12 mmol) in water (50 mL) was added to a solution of compound 4 (8 g; 12 mmol) in water (200 mL). The pH was raised to 8 with 2N NaOH and the stirred solution was heated to 50° C. then neutralized to pH 7 with 1N HCl and finally purified by chromatography on Amberlite XAD 1600 column (eluent: gradient water/MeCN) to give the gadolinium complex 5 (10.1 g). Yield: 95%.

Mass spectrum and elemental analysis were consistent with the expected structure.

Example 24: Relaxometric Properties

The relaxometric properties of some representative complex compounds according to the invention have been determined at different magnetic field strengths, e.g. including 0.47 and 1.41 T, at 37° C. and in different media (physiologic solution and human plasma) and compared with relaxivity values measured, at the same conditions, for some Gd-Complex of the market having an analogous cyclic coordination cage.

Materials

Apparatus

The longitudinal water proton relaxation rate ($R_1=1/T_1$) was measured at 0.47 T with a Minispec MQ-20 spectrometer (Bruker Biospin, Germany) operating at a proton Larmor frequency of 20 MHz; MR experiments at 1.41 T were performed using a Minispec MQ-60 spectrometer (Bruker Biospin, Germany) operating at a proton Larmor frequency of 60 MHz.

Methods

Sample Preparation

All test articles were used as supplied and diluted in the selected medium (physiologic solution or human plasma) by weighting the required amount of paramagnetic chelated complex to get a 5 or 10 mM starting solution.

Relaxivity Measurements

Five different concentration samples (0.1, 0.25, 0.5, 0.75 and 1 mM) for each medium have been prepared by further dilution of the starting 5 or 10 mM solution.

Relaxation Measurement

Relaxivity measurements were performed at 0.47 T and 1.41 T at a preset temperature sample of 37° C., kept constant by means of a thermostatic bath connected to the sample holder of the spectrometer. The five sample solutions have been preliminary pre-heated at 37° C. in an external thermostatic bath and then left 10 minutes inside the internal bath to assure the stabilization of the temperature. Longitudinal relaxation time $T_1$ was measured by means of a standard inversion recovery sequence, where the inversion time (TI) was varied from 10 ms to at least 5 times $T_1$ in 15 steps. Statistical analysis (mono-exponential fitting for $T_1$ measurement, linear fitting for the evaluation of longitudinal relaxivity) was performed by Mathematica® (Wolfram, USA). Errors on the estimated parameters were evaluated by the fitting procedure.

Results

The relaxivity values $r_{1p}$ obtained from some representative compounds according to the invention, both in physiologic solution and in human plasma, at 37° C., are summarized in the following Table A, together with the structure of tested compounds and the strength of the applied magnetic field (in T), and compared with corresponding values measured for some commercial contrast agents in clinical practice.

TABLE A

| | $r_{1p}$ [mM$^{-1}$s$^{-1}$] in human plasma | |
|---|---|---|
| Complex | 0.47 T 37° C., | 1.41 T 37° C. |
| Dotarem® | 4.5 | 3.6 |

TABLE A-continued

| Complex | $r_{1p}$ [mM$^{-1}$s$^{-1}$] in human plasma | |
|---|---|---|
|  | 0.47 T 37° C., | 1.41 T 37° C. |
| ProHance® | 4.9 | 4.15 |
| Comparative 1 | 5.2 | 4.5 |
| Chelate Complex 1 | 8.2 | 6.7 |
| Chelate Complex 7 | 10.2 | 8.2 |
| Chelate Complex 11 | 8.45 | 7.3 |

TABLE A-continued r₁ₚ [mM⁻¹s⁻¹] in human plasma

| Complex | 0.47 T 37° C., | 1.41 T 37° C. |
|---|---|---|
| Chelate Complex 12 | 8.3 | 7.1 |
| Chelate Complex 21 | 11.45 | 8.8 |
| Chelate Complex 16 | 9.6 | 8.6 |
| Chelate Complex 18 | 7.41 | 6.8 |

Conclusions

The relaxivity of the investigated contrast agents (in human plasma) ranges between 5.2 (for the unsubstituted Comparative 1) and 11.45 (for the Chelate Complex 21) mM$^{-1}$s$^{-1}$ at 0.47 T. Such values decrease, as expected, increasing the magnetic field strength. These results confirm that the particular selection represented by the paramagnetic complexes and, especially, the Gd$^{3+}$ complexes of the compounds of formula (I) of the invention show an increased relaxivity r$_{1p}$, which is at least about 1.5 up to 2 times the relaxivity shown, at the same conditions in human plasma, at 37° C., by the contrast agents currently in use in the daily diagnostic practice, such as Dotarem® and ProHance®.

The invention claimed is:

1. A compound of formula (I),

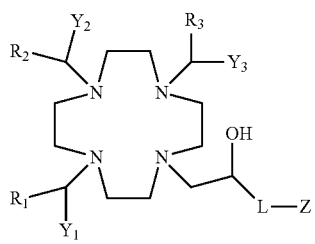

(I)

where:

R$_1$, R$_2$ and R$_3$ independently of one another are H or a C$_1$-C$_3$ alkyl optionally substituted by a C$_1$-C$_3$ alkoxy or C$_1$-C$_3$ hydroxyalkoxy group, or by a phenyl ring;

Y$_1$, Y$_2$ and Y$_3$ independently of one another are a group of formula —PO(OR')$_2$, —PO(R$_4$)(OR'), or —COOR', with the proviso that at least one of them is —PO(OR')$_2$ or —PO(R$_4$)(OR');

in which:

R' independently of one another is H or C$_1$-C$_5$ alkyl;

R$_4$ is an aryl or a cycloalkyl ring, or a C$_1$-C$_5$ alkyl which is optionally substituted by an aryl or cycloalkyl ring;

L is a direct bond; and

Z is selected from the group consisting of: a substituted phenyl and a C$_1$-C$_6$ alkyl comprising a substituent group selected from the groups of formula —NHSO$_2$R$_5$, —NHC(O)NHR$_6$, —NHC(O)OR$_7$ and —NR$_8$R$_9$ where:

R$_5$ is a phenyl or cycloalkyl ring;

R$_6$ is C$_1$-C$_5$ alkyl, optionally substituted with a phenyl or a cycloalkyl ring; or a phenyl or cycloalkyl ring;

R$_7$ is C$_1$-C$_5$ alkyl interrupted by one or more oxygen atoms and optionally substituted by a phenyl or a cycloalkyl ring; or a phenyl or cycloalkyl ring;

R$_8$ is a phenyl or cycloalkyl ring; or a C$_1$-C$_5$ alkyl substituted by a phenyl or cycloalkyl ring;

R$_9$ is H, or a group of formula —(CH$_2$)$_n$PO(OR')$_2$ or —(CH$_2$)$_n$PO(R$_4$)(OR'); or individual diastereoisomers, their racemic mixtures, geometric isomers, or solved enantiomers of the same, or a physiologically acceptable salt thereof.

2. A compound according to claim 1 in which Z is a substituted phenyl, having the formula (III)

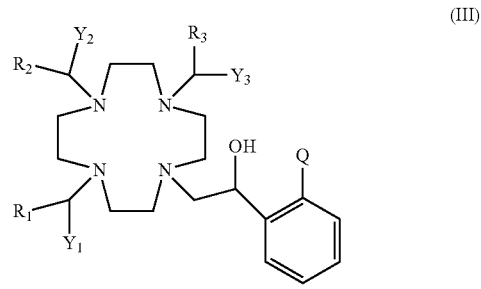

(III)

in which Q is a substituent group selected from the group consisting of: hydroxyl, —NH$_2$, C$_1$-C$_3$ alkoxy, C$_1$-C$_3$ hydroxyalkyl, and carboxyl.

3. A compound according to claim 1 in which Z is a C$_1$-C$_6$ alkyl comprising a substituent group selected from the groups of formula —NHSO$_2$R$_5$, —NHC(O)NHR$_6$, —NHC(O)OR$_7$ and —NR$_8$R$_9$.

4. A compound according to claim 3 having the formula (V)

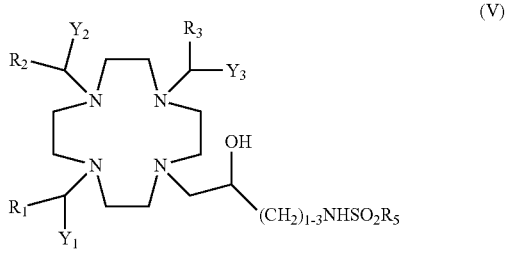

(V)

in which R$_5$ is as defined in claim 1;

or the formula (VI)

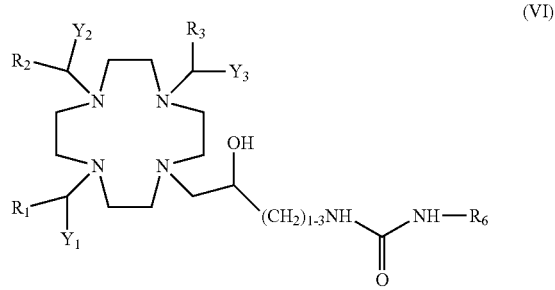

(VI)

in which $R_6$ is a $C_1$-$C_3$ alkyl optionally substituted by a phenyl or a cyclohexyl ring, or is a phenyl or cyclohexylalkyl ring;

or the formula (VII)

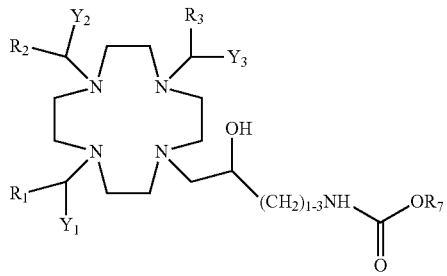

(VII)

in which $R_7$ is a $C_1$-$C_5$ alkyl interrupted by one or more oxygen atom(s) and optionally substituted by a phenyl or a cyclohexyl ring, or is a phenyl or cyclohexylalkyl ring;

or the formula (VIII)

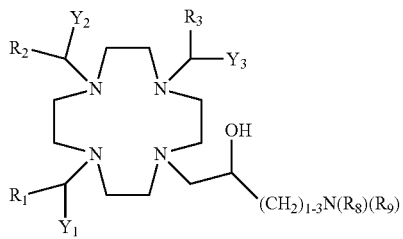

(VIII)

in which:
- $R_8$ is a phenyl or cycloalkyl ring; or is a $C_1$-$C_3$ alkyl substituted by a phenyl or cyclohexyl ring;
- $R_9$ is a hydrogen atom, or a group selected from the groups of formula —$(CH_2)_n PO(OR')_2$ and —$(CH_2)_n PO(R_4)(OR')$ in which n, R' and $R_4$ are as defined in claim 1.

5. A compound according to claim 1 in which in the formula (I) one of $Y_1$, $Y_2$ and $Y_3$ is a carboxyl of formula —COOR' and the other two, independently from one another, are selected from —PO(OR')$_2$ and —PO($R_4$)(OR').

6. A compound according to claim 1 in which in the formula (I) one of $Y_1$, $Y_2$ and $Y_3$ is selected from —PO(OR')$_2$ and —PO($R_4$) (OR') and the remaining two are carboxyls of formula —COOR'.

7. A compound according to claim 1 in which in the formula (I) R' is H.

8. A compound of formula (I) according to claim 1 selected from the group consisting of:

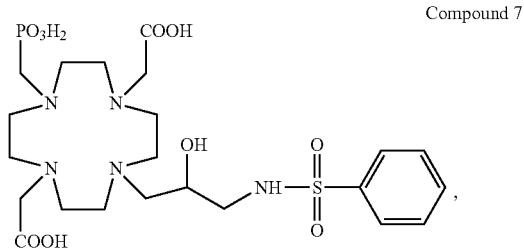

Compound 7

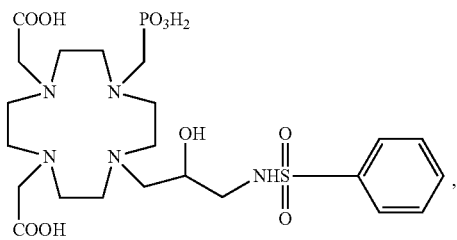

Compound 8

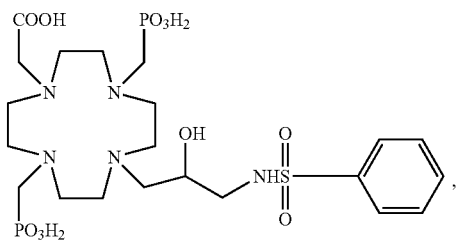

Compound 9

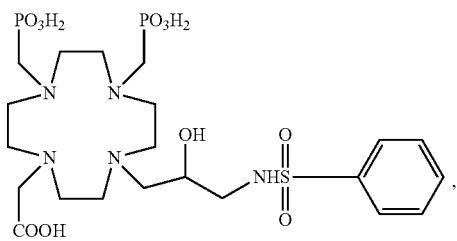

Compound 10

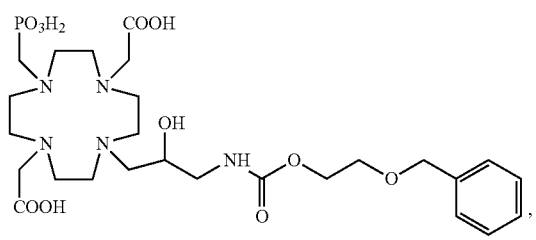

Compound 22

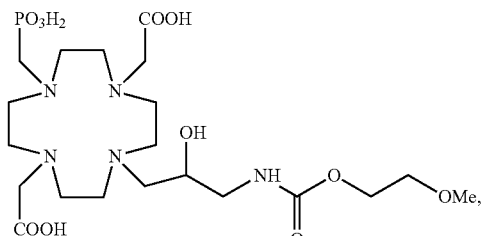

Compound 23

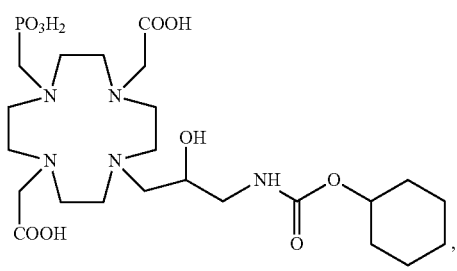

Compound 24

-continued

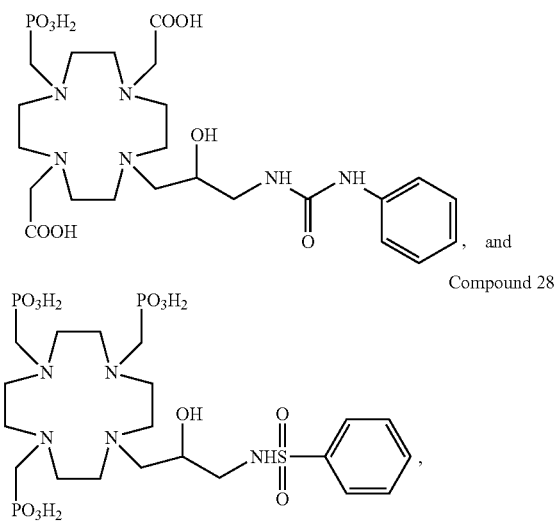

Compound 25

Compound 28 or a physiologically acceptable salt thereof.

9. A paramagnetic complex of the compound of formula (I) according to claim 1 with a paramagnetic metal ion selected from the group consisting of Fe(2+), Fe(3+), Cu(2+), Cr(3+), Gd(3+), Eu(3+), Dy(3+), La(3+), Yb(3+) and Mn(2+), or a physiologically acceptable salt thereof.

10. A compound of formula (I) according to claim 1, wherein the physiologically acceptable salt is with a cation of (i) an inorganic base selected from an alkali metal and alkaline-earth metal selected from potassium, sodium, calcium and magnesium, or of (ii) an organic base selected from ethanolamine, diethanolamine, morpholine, glucamine, N-methylglucamine, and N,N-dimethylglucamine or of (iii) an amino acid selected from lysine, arginine and ornithine or with (iv) an anion of a halo acid, as well as of (v) other suitable ions selected from acetate, succinate, citrate, fumarate, maleate and oxalate.

11. A pharmaceutical composition comprising the paramagnetic complex, or a pharmaceutical salt thereof, as defined in claim 9 in combination with a pharmaceutically acceptable carrier, diluent, excipient, or combination thereof.

12. A process for the preparation of a compound of formula (I) as defined in claim 1 comprising the following main steps:
   a) Obtaining a macrocyclic substrate 1 in a protected form;
   b) Obtaining an alkylating molecule 2, in which any optional functional group(s) not involved with the coupling reaction with the substrate 1 is protected;
   c) Coupling the protected substrate 1 with the alkylating molecule 2, to give the desired compound of formula (I) in a protected form or, alternatively, an intermediate thereof 3;
   d) Optionally converting the intermediate obtained at the step c) of the process in the protected compound of formula (I);
   e) Removing any protecting group and isolating the chelating ligand of formula (I); and
   f) Complexing the obtained ligand with a paramagnetic metal ion and isolating the chelate complex, or the salt thereof.

13. A method for the in vivo imaging a human or animal body organ or tissue by use of the MRI technique that comprises the steps of:
   a) administering the pharmaceutical composition according to claim 11 to a human or animal, positioning the human or animal in a MRI imaging system,
   b) submitting the human or animal to a radiation frequency selected to excite the non-zero proton spin nuclei of the active paramagnetic substrate; and
   c) recording a MR signal from said excited nuclei.

14. A method for the in vitro (ex vivo) imaging of a biological sample from a patient, by use of the MRI technique, that comprises contacting an effective amount of the paramagnetic complex or a physiologically acceptable salt thereof as defined in claim 9 with the biological sample and then obtaining MRI signals from said sample by use of the MRI.

15. A compound according to claim 1 in which in the formula (I) $R_1$, $R_2$ and $R_3$ are H.

* * * * *